(12) United States Patent
Sullivan et al.

(10) Patent No.: US 11,697,667 B2
(45) Date of Patent: Jul. 11, 2023

(54) SALTS AND POLYMORPHS OF CETHROMYCIN FOR THE TREATMENT OF DISEASE

(71) Applicant: AliquantumRx, Inc., Baltimore, MD (US)

(72) Inventors: David Sullivan, Baltimore, MD (US); Amanda Hill, Cambridge (GB); Kate Wittering, Cambridge (GB); Amy Tapper, Boston, MA (US); Nikola Kaludov, Deale, MD (US)

(73) Assignee: AliquantumRx, Inc., Baltimore, MD (US)

( * ) Notice: Subject to any disclaimer, the term of this patent is extended or adjusted under 35 U.S.C. 154(b) by 253 days.

(21) Appl. No.: 17/109,970

(22) Filed: Dec. 2, 2020

(65) Prior Publication Data
US 2021/0163522 A1 Jun. 3, 2021

Related U.S. Application Data

(60) Provisional application No. 62/942,508, filed on Dec. 2, 2019.

(51) Int. Cl.
*C07H 17/08* (2006.01)
*A61P 33/06* (2006.01)
*A61K 31/706* (2006.01)

(52) U.S. Cl.
CPC ........... *C07H 17/08* (2013.01); *A61K 31/706* (2013.01); *A61P 33/06* (2018.01); *C07B 2200/13* (2013.01)

(58) Field of Classification Search
CPC .... C07H 17/08; A61K 31/706; C07B 2200/13
See application file for complete search history.

(56) References Cited

U.S. PATENT DOCUMENTS 5,866,549 A * 2/1999 Or .......................... A61P 31/00
536/7.2

FOREIGN PATENT DOCUMENTS

| WO | WO-2016033023 A2 * | 3/2016 | ........... A61K 31/122 |
| WO | 2021113357 | 6/2021 | |

OTHER PUBLICATIONS

Morisette et al., "High-throughput crystallization: polymorphs, salts, co-crystals and solvates of pharmaceutical solids" Advanced Drug Delivery Reviews vol. 56 pp. 275-300 doi:10.1016/j.addr.2003.10.020 (Year: 2004).*

(Continued)

*Primary Examiner* — Eric Olson
(74) *Attorney, Agent, or Firm* — Cynthia Hathaway; Brock Levin

(57) ABSTRACT

Disclosed herein are new salts and polymorphs of cethromycin for the treatment of diseases due to infection by bacteria and certain protozoans, including, for example, malaria, Babesosis, Toxoplasmosis, diarrheal disease, respiratory disease, sexually transmitted bacterial infections, and some bioterror bacteria, including, for example, plague, tularemia and post-inhalation anthrax. Also disclosed herein are new salts and polymorphs of cethromycin for the treatment of inflammatory diseases, including, for example, pelvic inflammatory disease, and peptic ulcer disease.

21 Claims, 27 Drawing Sheets

(56) References Cited

OTHER PUBLICATIONS

Oganov et al., "Crystal structure prediction: reflections on present status and challenges" Faraday Discussions vol. 211 pp. 643-660 DOI: 10.1039/c8fd90033g (Year: 2018).*

Cruz-Cabeza, A.. "Crystal structure prediction: are we there yet?" Acta Cryst B72 pp. 437-438 http://dx.doi.org/10.1107/S2052520616011367 (Year: 2016).*

* cited by examiner

SALTS AND POLYMORPHS OF CETHROMYCIN FOR THE TREATMENT OF DISEASE

This application claims the benefit of priority of U.S. Provisional Application No. 62/942,508, filed Dec. 2, 2019, the disclosure of which is incorporated by reference as if written herein in its entirety.

Disclosed herein are new substituted cethromycin salts and polymorphs and compositions and their application as pharmaceuticals for the treatment of disease. Methods of treatment diseases due to infection by bacteria and certain protozoans, including, for example, malaria, Babesosis, Toxoplasmosis, diarrheal disease, respiratory disease, sexually transmitted bacterial infections, and some bioterror bacteria, including, for example, plague, tularemia and post-inhalation anthrax, are also provided. Also disclosed herein are new salts and polymorphs of cethromycin for the treatment of inflammatory diseases, including, for example, pelvic inflammatory disease, and peptic ulcer disease.

Novel compounds and pharmaceutical compositions, certain of which have been found to inhibit protein synthesis in bacterias, mycobacterias and certain protozoans, together with methods of synthesizing and using the compounds including methods for the treatment of infectious diseases in a patient by administering the compounds.

DETAILED DESCRIPTION

Figure 1:
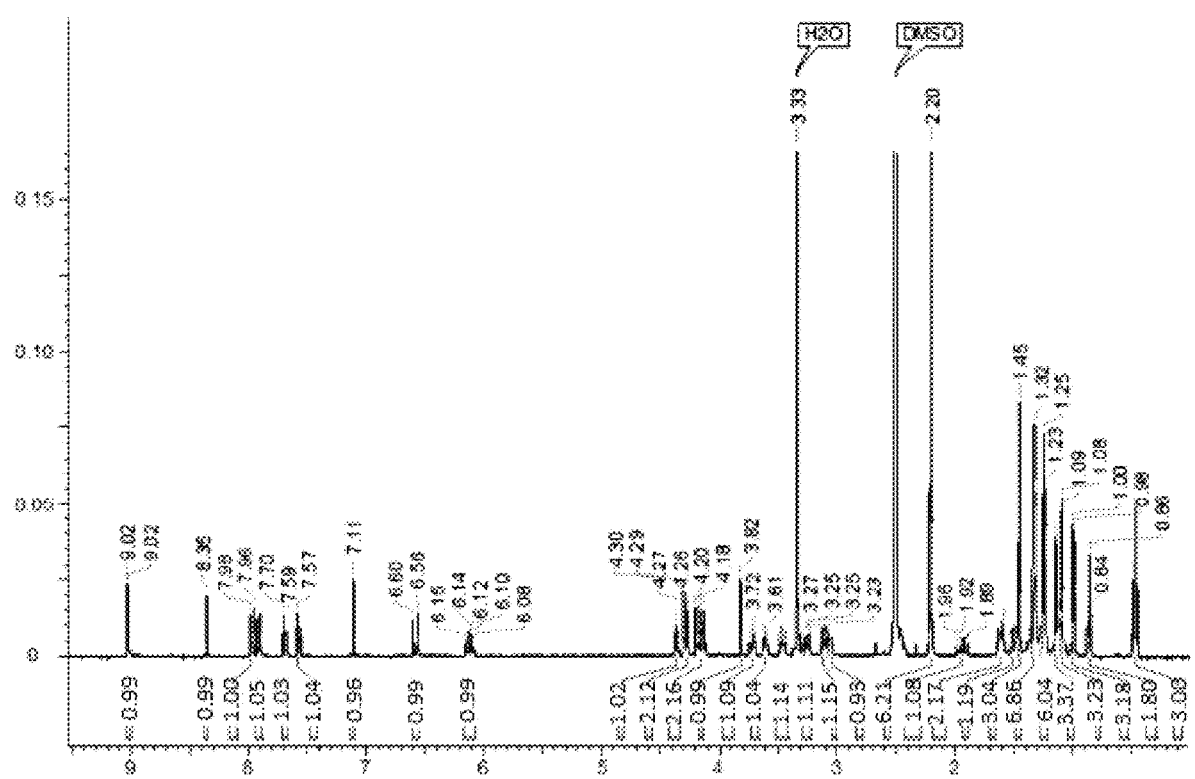
FIG. 1 shows the $^1$H NMR spectrum of the Example 1 compound (DMSO-$d_6$).

Provided herein is Embodiment 1: a compound have structural Formula I:

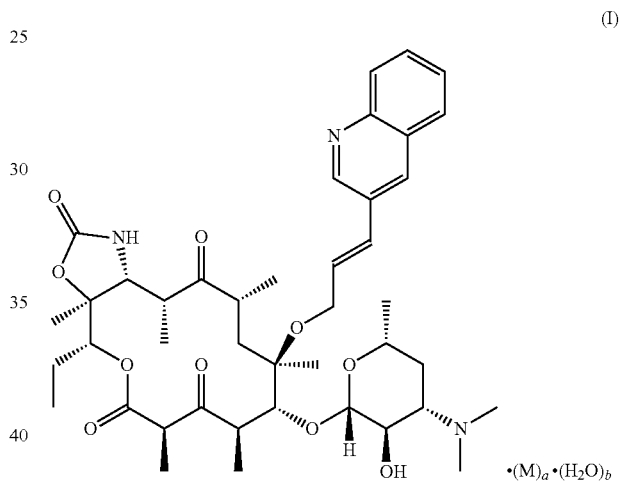

(I)

or a polymorph thereof, wherein:

a is a fractional or whole number between about 0.5 and 3.5, inclusive;

b is a fractional or whole number between about 0 and 10, inclusive; and M is selected from hydrochloric acid, phosphoric acid, and acetic acid.

Certain compounds disclosed herein possess useful activity for inhibition of bacterial protein synthesis, and may be used in the treatment or prophylaxis of a disease in which bacterial protein synthesis plays an active role. Certain embodiments provide methods for inhibiting bacterial protein synthesis. Other embodiments provide methods for treating a disease caused by a bacterial infection, in a patient in need of such treatment, comprising administering to said patient a therapeutically effective amount of a compound or composition as disclosed herein. Also provided is the use of certain compounds disclosed herein for use in the manufacture of a medicament for the treatment of a disease ameliorated by the inhibition of bacterial protein synthesis.

In some embodiments, the bacterium is chosen from *Bacteroides*, including, for example, *B. tectum*; *Corynebacterium*; *Chlamydia*, including, for example, *C. pneumoniae* and *C. trachomatis*; *Eikenella*, including, for example, *E. corrodens*; *Enterobacteriaceae*; *Fusobacterium*, including, for example, *F. nucleatum*; *Haemophilus*, including, for example, *H. influenzae*; *Leigonella*, including, for example, *L. pneumophila*; *Moraxella*, including, for example, *M. catarrhalis*; *Mycobacterium*, including, for example, *M. avium, M. intracellulare, M. chimaera, M. kansasii, M. malmoense, M. xenopi, M. abscessus, M. fortuitum* complex, and *M. chelonae*; *Mycoplasma*, including, for example, *M. hominis, M. genitalium*, and *M. pneumoniae*; *Neisseria*, including, for example, *N. gonorrhoeae*; *Pasteurella*, including, for example, *P. septica and P. multocida*; *Peptostreptococcus*, including, for example, *P. magnus* and *P. micros*; *Prevotella*, including, for example, *P. melaninogenica* and *P. heparinolytica*; *Porphyromonas*; *Propionibacterium*; *Staphylococcus*, including, for example, *S. aureus*; *Streptococcus*, including, for example, *S. pneumoniae*; *Ureaplasma*, including, for example, *U. urealyticum* and *U. parvum*; and *Veillonella*.

Certain compounds disclosed herein possess useful activity for inhibition of protozoan protein synthesis, and may be used in the treatment or prophylaxis of a disease in which bacterial protein synthesis plays an active role. Certain embodiments provide methods for inhibiting protozoan protein synthesis. Other embodiments provide methods for treating an disease caused by a protozoan infection, in a patient in need of such treatment, comprising administering to said patient a therapeutically effective amount of a compound or composition as disclosed herein. Also provided is the use of certain compounds disclosed herein for use in the manufacture of a medicament for the treatment of a disease ameliorated by the inhibition of protozoan protein synthesis.

In some embodiments, the protozoan is chosen from *Cryptosporidium*; *Coccidia*; *Plasmodium*; *Toxoplasma*; including, for example, *T. gondii*; *Babesia*; and *Neospora*. In some embodiments, the protozoan is *Toxoplasma gondii*. In some embodiments, the protozoan is a *Plasmodium* species. In some embodiments, the *Plasmodium* is chosen from *P. falciparum, P. vivax, P. ovale, P. malariae*, and *P. knowlesi*. In some embodiments, the *Plasmodium* is *P. falciparum*.

Also provided are pharmaceutical compositions comprising one or more compounds disclosed herein together with a pharmaceutically acceptable carrier, as well as methods of making and using the compounds and compositions.

The disclosure provides the further embodiments:

Embodiment 2: The compound of Embodiment 1, wherein M is acetic acid.

Embodiment 3: The compound of Embodiment 1, wherein M is phosphoric acid.

Embodiment 4: The compound of Embodiment 1, wherein M is hydrochloric acid.

Embodiment 5: The compound of any one of Embodiment 1-4 wherein the compound is in a solid form.

Embodiment 6: The compound of any one of Embodiment 1-5 wherein the compound is in a crystalline form.

Embodiment 7: The compound of Embodiment 1, wherein a is a fractional or whole number between about 0.5 and 3.0, inclusive.

Embodiment 8: The compound of Embodiment 7, wherein a is a fractional or whole number between about 0.5 and 2.0, inclusive.

Embodiment 9: The compound of Embodiment 8, wherein a is a fractional or whole number between about 0.5 and 1.5, inclusive.

Embodiment 10: The compound of Embodiment 9, wherein a is a fractional or whole number between about 0.5 and 1.0, inclusive.

Embodiment 11: The compound of Embodiment 10, wherein a is about 1.0.

Embodiment 12: The compound of Embodiment 11, wherein a is 1.0.

Embodiment 13: The compound of Embodiment 12, wherein M is acetic acid.

Embodiment 14: The compound of Embodiment 13, characterized by the presence of four or more peaks with d-spacings of about 14.6, 10.6, 9.4, 8.0, 7.4, 6.6, 5.1, 4.3, 4.0 and 3.9 Å.

Embodiment 15: The compound of Embodiment 14, characterized by the presence of five or more peaks with d-spacings of about 14.6, 10.6, 9.4, 8.0, 7.4, 6.6, 5.1, 4.3, 4.0 and 3.9 Å.

Embodiment 16: The compound of Embodiment 15, characterized by the presence of six or more peaks with d-spacings of about 14.6, 10.6, 9.4, 8.0, 7.4, 6.6, 5.1, 4.3, 4.0 and 3.9 Å.

Embodiment 17: The compound of Embodiment 16, characterized by the presence of seven or more peaks with d-spacings of about 14.6, 10.6, 9.4, 8.0, 7.4, 6.6, 5.1, 4.3, 4.0 and 3.9 Å.

Embodiment 18: The compound of Embodiment 17, characterized by the presence of eight or more peaks with d-spacings of about 14.6, 10.6, 9.4, 8.0, 7.4, 6.6, 5.1, 4.3, 4.0 and 3.9 Å.

Embodiment 19: The compound of Embodiment 13, characterized by the presence of four or more peaks with 2-theta values, using CuKα radiation, of about 6.0, 8.3, 9.4, 11.0, 12.0, 13.4, 17.3, 20.9, 22.2, and 22.6 degrees.

Embodiment 20: The compound of Embodiment 19, characterized by the presence of five or more peaks with 2-theta values, using CuKα radiation, of about 6.0, 8.3, 9.4, 11.0, 12.0, 13.4, 17.3, 20.9, 22.2, and 22.6 degrees.

Embodiment 21: The compound of Embodiment 20, characterized by the presence of six or more peaks with 2-theta values, using CuKα radiation, of about 6.0, 8.3, 9.4, 11.0, 12.0, 13.4, 17.3, 20.9, 22.2, and 22.6 degrees.

Embodiment 22: The compound of Embodiment 21, characterized by the presence of seven or more peaks with 2-theta values, using CuKα radiation, of about 6.0, 8.3, 9.4, 11.0, 12.0, 13.4, 17.3, 20.9, 22.2, and 22.6 degrees.

Embodiment 23: The compound of Embodiment 22, characterized by the presence of eight or more peaks with 2-theta values, using CuKα radiation, of about 6.0, 8.3, 9.4, 11.0, 12.0, 13.4, 17.3, 20.9, 22.2, and 22.6 degrees.

Embodiment 24: The compound of Embodiment 12, wherein M is hydrochloric acid.

Embodiment 25: The compound of Embodiment 24, characterized by the presence of four or more peaks with d-spacings of about 14.1, 12.9, 10.1, 8.8, 8.5, 6.5, 5.5, 5.1, 4.8, and 4.4 Å.

Embodiment 26: The compound of Embodiment 25, characterized by the presence of five or more peaks with d-spacings of about 14.1, 12.9, 10.1, 8.8, 8.5, 6.5, 5.5, 5.1, 4.8, and 4.4 Å.

Embodiment 27: The compound of Embodiment 26, characterized by the presence of six or more peaks with d-spacings of about 14.1, 12.9, 10.1, 8.8, 8.5, 6.5, 5.5, 5.1, 4.8, and 4.4 Å.

Embodiment 28: The compound of Embodiment 27, characterized by the presence of seven or more peaks with d-spacings of about 14.1, 12.9, 10.1, 8.8, 8.5, 6.5, 5.5, 5.1, 4.8, and 4.4 Å.

Embodiment 29: The compound of Embodiment 28, characterized by the presence of eight or more peaks with d-spacings of about 14.1, 12.9, 10.1, 8.8, 8.5, 6.5, 5.5, 5.1, 4.8, and 4.4 Å.

Embodiment 30: The compound of Embodiment 24, characterized by the presence of four or more peaks with 2-theta values, using CuKα radiation, of about 6.3, 6.9, 8.7, 10.0, 10.5, 13.7, 16.0, 17.5, 18.6, and 20.2 degrees.

Embodiment 31: The compound of Embodiment 30, characterized by the presence of five or more peaks with 2-theta values, using CuKα radiation, of about 6.3, 6.9, 8.7, 10.0, 10.5, 13.7, 16.0, 17.5, 18.6, and 20.2 degrees.

Embodiment 32: The compound of Embodiment 31, characterized by the presence of six or more peaks with 2-theta values, using CuKα radiation, of about 6.3, 6.9, 8.7, 10.0, 10.5, 13.7, 16.0, 17.5, 18.6, and 20.2 degrees.

Embodiment 33: The compound of Embodiment 32, characterized by the presence of seven or more peaks with 2-theta values, using CuKα radiation, of about 6.3, 6.9, 8.7, 10.0, 10.5, 13.7, 16.0, 17.5, 18.6, and 20.2 degrees.

Embodiment 34: The compound of Embodiment 33, characterized by the presence of eight or more peaks with 2-theta values, using CuKα radiation, of about 6.3, 6.9, 8.7, 10.0, 10.5, 13.7, 16.0, 17.5, 18.6, and 20.2 degrees.

Embodiment 35: The compound of any one of Embodiments 24-34, characterized by a mass loss, upon heating to 100° C., of about 5.3% or less.

Embodiment 36: The compound of any one of Embodiments 24-34, characterized by water content, as measured by Karl Fischer titration, of about 3.3 equivalents of water or less.

Embodiment 37: The compound of any one of Embodiments 24-34, characterized by a kinetic solubility, at 2 hr, in simulated gastric fluid (SGF), of about 27 mg/mL or more.

Embodiment 38: The compound of any one of Embodiments 24-34, characterized by a thermodynamic solubility, at 24 hr, in phosphate buffered saline (PBS), of about 27 mg/mL or more.

Embodiment 39: The compound of Embodiment 24, characterized by the presence of four or more peaks with d-spacings of about 16.5, 14.5, 10.5, 9.1, 8.3, 7.8, 7.6, 5.2, 4.7, and 4.1 Å.

Embodiment 40: The compound of Embodiment 39, characterized by the presence of five or more peaks with d-spacings of about 16.5, 14.5, 10.5, 9.1, 8.3, 7.8, 7.6, 5.2, 4.7, and 4.1 Å.

Embodiment 41: The compound of Embodiment 40, characterized by the presence of six or more peaks with d-spacings of about 16.5, 14.5, 10.5, 9.1, 8.3, 7.8, 7.6, 5.2, 4.7, and 4.1 Å.

Embodiment 42: The compound of Embodiment 41, characterized by the presence of seven or more peaks with d-spacings of about 16.5, 14.5, 10.5, 9.1, 8.3, 7.8, 7.6, 5.2, 4.7, and 4.1 Å.

Embodiment 43: The compound of Embodiment 42, characterized by the presence of eight or more peaks with d-spacings of about 16.5, 14.5, 10.5, 9.1, 8.3, 7.8, 7.6, 5.2, 4.7, and 4.1 Å.

Embodiment 44: The compound of Embodiment 24, characterized by the presence of four or more peaks with 2-theta values, using CuKα radiation, of about 5.3, 6.1, 8.4, 9.8, 10.7, 11.4, 11.6, 17.0, 18.8, and 21.4 degrees.

Embodiment 45: The compound of Embodiment 44, characterized by the presence of five or more peaks with 2-theta values, using CuKα radiation, of about 5.3, 6.1, 8.4, 9.8, 10.7, 11.4, 11.6, 17.0, 18.8, and 21.4 degrees.

Embodiment 46: The compound of Embodiment 45, characterized by the presence of six or more peaks with 2-theta values, using CuKα radiation, of about 5.3, 6.1, 8.4, 9.8, 10.7, 11.4, 11.6, 17.0, 18.8, and 21.4 degrees.

Embodiment 47: The compound of Embodiment 46, characterized by the presence of seven or more peaks with 2-theta values, using CuKα radiation, of about 5.3, 6.1, 8.4, 9.8, 10.7, 11.4, 11.6, 17.0, 18.8, and 21.4 degrees.

Embodiment 48: The compound of Embodiment 47, characterized by the presence of eight or more peaks with 2-theta values, using CuKα radiation, of about 5.3, 6.1, 8.4, 9.8, 10.7, 11.4, 11.6, 17.0, 18.8, and 21.4 degrees.

Embodiment 49: The compound of any one of Embodiments 24-48, characterized by a mass loss, upon heating to 100° C., of about 5.1% or less.

Embodiment 50: A compound as recited in any of Embodiments 1-48 for use as a medicament.

Embodiment 51: A compound as recited in any of Embodiments 1-48 for use in the treatment of a disease.

Embodiment 52: A compound as recited in any of Embodiments 1-48 for use in the manufacture of a medicament for the prevention or treatment of a disease.

Embodiment 53: A pharmaceutical composition comprising a compound as recited in any of Embodiments 1-48 together with a pharmaceutically acceptable carrier.

Embodiment 54: A method of inhibition of microbial protein synthesis comprising contacting bacteria with a compound as recited in any of Embodiments 1-48.

Embodiment 55: The method as recited in Embodiment 54, wherein the microbe is a bacterium.

Embodiment 56: The method as recited in Embodiment 54, wherein the microbe is a protozoan.

Embodiment 57: A method of treatment of an infectious disease comprising the administration of a therapeutically effective amount of a compound as recited in any of Embodiments 1-48 to a patient in need thereof.

Embodiment 58: A method of treatment of an infectious disease comprising the administration of:
a therapeutically effective amount of a compound as recited in any of Embodiments 1-48; and
another therapeutic agent.

Embodiment 59: The method as recited in either one of Embodiments 57 and 58 wherein said infectious disease is anthrax.

Embodiment 60: The method as recited in either one of Embodiments 57 and 58 wherein said infectious disease is malaria.

Embodiment 61: The method as recited in either one of Embodiments 57 and 58 wherein said infectious disease is caused by a bacterium.

Embodiment 62: The method as recited in either one of Embodiments 57 and 58 wherein said infectious disease is caused by a protozoan.

Embodiment 63: A method for achieving an effect in a patient comprising the administration of a therapeutically effective amount of the compound as recited in any of Embodiments 1-48 to a patient, wherein the effect is chosen from:
reducing microbial level(s);
increasing the rate of microbial killing;
decreasing the minimal dose for cure (e.g., reduction of the level of microbia to an undetectable level); and
decreasing the duration of time required for cure (e.g., reduction of the level of microbia to an undetectable level).

Embodiment 64: The method as recited in Embodiment 63, wherein the microbe is a bacterium.

Embodiment 65: The method as recited in Embodiment 63, wherein the microbe is a protozoan.

Embodiment 66: The method as recited in any of Embodiments 55, 61, and 64, wherein the bacterium is chosen from

*Bacteroides*, including, for example, *B. tectum; Corynebacterium; Chlamydia*, including, for example, *C. pneumoniae* and *C. trachomatis;* Eikenella, including, for example, *E. corrodens; Enterobacteriaceae; Fusobacterium*, including, for example, *F. nucleatum; Haemophilus*, including, for example, *H. influenzae; Leigonella*, including, for example, *L. pneumophila; Moraxella*, including, for example, *M. catarrhalis; Mycobacterium*, including, for example, *M. avium, M. intracellulare, M. chimaera, M. kansasii, M. malmoense, M. xenopi, M. abscessus, M. fortuitum* complex, and *M. chelonae; Mycoplasma*, including, for example, *M. hominis, M. genitalium*, and *M. pneumoniae; Neisseria*, including, for example, *N. gonorrhoeae; Pasteurella*, including, for example, *P. septica and P. multocida; Peptostreptococcus*, including, for example, *P. magnus* and *P. micros; Prevotella*, including, for example, *P. melaninogenica* and *P. heparinolytica; Porphyromonas; Propionibacterium; Staphylococcus*, including, for example, *S. aureus; Streptococcus*, including, for example, *S. pneumoniae; Ureaplasma*, including, for example, *U. urealyticum* and *U. parvum;* and *Veillonella*.

Embodiment 67: The method as recited in as recited in either one of Embodiments 56, 62, and 65, wherein the protozoan is chosen from *Cryptosporidium; Coccidia; Plasmodium; Toxoplasma; Babesia;* and *Neospora*.

Embodiment 68: The method as recited in Embodiment 67, wherein the protozoan is *Toxoplasma gondii*.

Embodiment 69: The method as recited in Embodiment 67, wherein the protozoan is a *Plasmodium* species.

Embodiment 70: The method as recited in Embodiment 69, wherein the *Plasmodium* is chosen from *P. falciparum, P. vivax, P. ovale, P. malariae*, and *P. knowlesi*.

Embodiment 71: The method as recited in Embodiment 70, wherein the *Plasmodium* is *P. falciparum*.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein a salt is specified to be the chloride (hydrochloric acid) salt is mutually exclusive with an embodiment in which the salt is specified to be the acetate (acetic acid) salt.

In certain embodiments, b is 0 (i.e., is absent). In certain embodiments, b is about 1.0. In certain embodiments, b is about 2.0.

The present disclosure also relates to a method of inhibiting protein synthesis in microbia such as bacteria and certain protozoans comprising the step of contacting bacteria with a compound as described herein. The cell phenotype, cell proliferation, protein synthesis activity, change in biochemical output related to protein synthesis, or binding of ribosomes with a compound disclosed herein, or binding of ribosomes with a biomolecule may be monitored. Such methods may be modes of treatment of disease, biological assays, cellular assays, biochemical assays, or the like.

Also provided herein is a method of treatment of an infectious disease comprising the administration of a therapeutically effective amount of a compound as disclosed herein, or a polymorph thereof, to a patient in need thereof.

Also provided herein is a compound as disclosed herein for use as a medicament.

Also provided herein is a compound as disclosed herein for use as a medicament for the treatment of an infectious disease.

Also provided is the use of a compound as disclosed herein as a medicament.

Also provided is the use of a compound as disclosed herein as a medicament for the treatment of an infectious disease.

Also provided is a compound as disclosed herein for use in the manufacture of a medicament for the treatment of an infectious disease.

Also provided is the use of a compound as disclosed herein for the treatment of an infectious disease.

In certain embodiments, the infectious disease is pneumonia.

In certain embodiments, the infectious disease is malaria.

In certain embodiments, the infectious disease is Babesiosis.

In certain embodiments, the infectious disease is Toxoplasmosis.

In certain embodiments, the infectious disease is diarrheal disease.

In certain embodiments, the infectious disease is a respiratory disease.

In certain embodiments, the infectious disease is a sexually transmitted bacterial infection.

In certain embodiments, the infectious disease is plague.

In certain embodiments, the infectious disease is tularemia.

In certain embodiments, the infectious disease is brucellosis.

In certain embodiments, the infectious disease is anthrax, including, for example, post-inhalation anthrax.

Also provided is a method for the treatment of an inflammatory disease. In certain embodiments, the inflammatory disease is pelvic inflammatory disease.

Also provided is a method for the treatment of a sexually transmitted disease. In certain embodiments, the sexually transmitted disease is caused by *N. gonorrhoeae*. In certain embodiments, the sexually transmitted disease is caused by *C. trachomatis*. In certain embodiments, the sexually transmitted disease is caused by *M. genitalium*. In certain embodiments, the sexually transmitted disease is lymphogranuloma venereum ("LGV").

Also provided is a method for the treatment of peptic ulcer disease. In certain embodiments, the treatment is provided to patients without risk factors for macrolide resistance.

Also provided herein is a method of inhibition of protein synthesis comprising contacting bacteria or protozoans with a compound as disclosed herein, or a polymorph thereof.

Also provided herein is a method for achieving an effect in a patient comprising the administration of a therapeutically effective amount of a compound as disclosed herein, or a polymorph thereof, to a patient, wherein the effect is wherein the effect is chosen from: reducing microbial level(s); increasing the rate of microbial killing; decreasing the minimal dose for cure (e.g., reduction of the level of microbia to an undetectable level); decreasing the duration of time required for cure (e.g., reduction of the level of microbia to an undetectable level); and decreased protein synthesis in bacteria and/or protozoans.

Also provided is a pharmaceutical composition comprising a compound as disclosed herein, together with a pharmaceutically acceptable carrier.

In certain embodiments, the pharmaceutical composition is formulated for oral administration.

In certain embodiments, the pharmaceutical composition is formulated for parenteral administration.

In certain embodiments, the oral pharmaceutical composition is chosen from a tablet and a capsule.

The disclosure of an embodiment without presenting a corresponding claim to that embodiment is not intended to signify disclaimer of the embodiment.

Abbreviations and Definitions

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The terms "benzo" and "benz," as used herein, alone or in combination, refer to the divalent radical $C_6H_4$=derived from benzene. Examples include benzothiophene and benzimidazole.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "halo," or "halogen," as used herein, alone or in combination, refers to fluorine, chlorine, bromine, or iodine.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —$CH_2$—NH—$OCH_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzindolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently chosen from nitrogen, oxygen, and sulfur. In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydroxy," as used herein, alone or in combination, refers to —OH.

The terms "sulfonate," "sulfonic acid," and "sulfonic," as used herein, alone or in combination, refer the —SO$_3$H group and its anion as the sulfonic acid is used in salt formation.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R'' where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N (R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and 1-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "salt" and its plural "salts" as used herein refer to an ionic compound comprising an ion of a compound (e.g., the drug cethromycin) and a counterion. Salts may be referred to herein interchangeably by the acid or base used to form them, e.g., the "hydrochloric acid" salt or "hydrochloride" salt, or as the "chloride" salt, as is often done in the art. Salts (and compounds in general) may exist as one or more different polymorphs.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including, for example, humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Pharmaceutical Compositions

While it may be possible for the compounds of the subject disclosure to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, polymorphs, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including, for example, subcutaneous, intradermal, intramuscular, intravenous, intraarticular, and intramedullary), intraperitoneal, transmucosal, transdermal, rectal and topical (including, for example, dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Administration and Treatment

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including, for example, the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

Oral Administration

The compounds of the present disclosure may be administered orally, including, for example, swallowing, so the compound enters the gastrointestinal tract, or is absorbed into the blood stream directly from the mouth, including, for example, sublingual or buccal administration.

Suitable compositions for oral administration include solid formulations such as tablets, pills, cachets, lozenges and hard or soft capsules, which can contain liquids, gels, powders, or granules, solutions or suspensions in an aqueous liquid or a non-aqueous liquid, or as an oil-in-water liquid emulsion or a water-in-oil liquid emulsion. The active ingredient may also be presented as a bolus, electuary or paste.

In a tablet or capsule dosage form the amount of drug present may be from about 0.05% to about 95% by weight, more typically from about 2% to about 50% by weight of the dosage form.

In addition, tablets or capsules may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet or capsule, may be present in amounts from about 0.1% to about 3% by weight, and include polysorbate 80, sodium dodecyl sulfate, talc and silicon dioxide.

Suitable lubricants, for use in a tablet or capsule, may be present in amounts from about 0.1% to about 5% by weight, and include calcium, zinc or magnesium stearate, sodium stearyl fumarate and the like.

Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with a liquid diluent. Dyes or pigments may be added to tablets for identification or to characterize different combinations of active compound doses.

Liquid formulations can include emulsions, solutions, syrups, elixirs and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as immediate or modified release, including, for example, delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Parenteral Administration

Compounds of the present disclosure may be administered directly into the blood stream, muscle, or internal organs by injection, e.g., by bolus injection or continuous infusion. Suitable means for parenteral administration include intravenous, intra-muscular, subcutaneous intraarterial, intraperitoneal, intrathecal, intracranial, and the like. Suitable devices for parenteral administration include injectors (including, for example, needle and needle-free injectors) and infusion methods. The formulations may be presented in unit-dose or multi-dose containers, for example sealed ampoules and vials.

Most parenteral formulations are aqueous solutions containing excipients, including, for example, salts, buffering, suspending, stabilizing and/or dispersing agents, antioxidants, bacteriostats, preservatives, and solutes which render the formulation isotonic with the blood of the intended recipient, and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions. Compositions for parenteral administration may be formulated as immediate or modified release, including, for example, delayed or sustained release. Compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Topical Administration

Compounds of the present disclosure may be administered topically (for example to the skin, mucous membranes, ear, nose, or eye) or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Typically, the active ingredient for topical administration may comprise from 0.001% to 10% w/w (by weight) of the formulation. In certain embodiments, the active ingredient may comprise as much as 10% w/w; less than 5% w/w; from 2% w/w to 5% w/w; or from 0.1% to 1% w/w of the formulation.

Compositions for topical administration may be formulated as immediate or modified release, including, for example, delayed or sustained release.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Rectal, Buccal, and Sublingual Administration

Suppositories for rectal administration of the compounds of the present disclosure can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Administration by Inhalation

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Other carrier materials and modes of administration known in the pharmaceutical art may also be used. Pharmaceutical compositions of the disclosure may be prepared by any of the well-known techniques of pharmacy, such as effective formulation and administration procedures. Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Combinations and Combination Therapy

In certain instances, it may be appropriate to administer at least one of the compounds described herein (or a pharmaceutically acceptable salt thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds of the disclosure with: donepezil, rivastigmine, galantamine, and memantine. Further examples include anti-amyloid antibodies and vaccines, anti-Ab antibodies and vaccines, anti-tau antibodies and vaccines, β-secretase inhibitors, 5-HT4 agonists, 5-HT6 antagonists, 5-HT1a antagonists, α7 nicotinic receptor agonists, 5-HT3 receptor antagonists, PDE4 inhibitors, O-GlcNAcase inhibitors, and other medicines approved for the treatment of Alzheimer's disease. Further examples include metformin, minocycline, tissue plasminogen activator, and other therapies that improve neuronal survival.

Further examples include the use of certain compounds of the disclosure with a rifamycin. In certain embodiments, the combination therapy is effective against macrolide susceptible nontuberculous mycobacteria, including, for example, *M. avium, M. intracellulare, M. chimaera, M. kansasii, M. malmoense, M. xenopi, M. abscessus, M. fortuitum* complex, and *M. chelonae*.

Further examples include the use of certain compounds of the disclosure with ethambutol. In certain embodiments, the combination therapy is effective against macrolide susceptible nontuberculous mycobacteria, including, for example, *M. avium, M. intracellulare, M. chimaera, M. kansasii, M. malmoense, M. xenopi, M. abscessus, M. fortuitum* complex, and *M. chelonae*.

Further examples include the use of certain compounds of the disclosure with a fluoroquinoline. In certain embodiments, the combination therapy is effective against plague, anthrax tularemia, and brucellosis.

Further examples include the use of certain compounds of the disclosure with an aminoglycoside. In certain embodiments, the combination therapy is effective against plague, anthrax tularemia, and brucellosis.

Further examples include the use of certain compounds of the disclosure with doxycycline. In certain embodiments, the combination therapy is effective against plague, anthrax tularemia, and brucellosis.

Further examples include the use of certain compounds of the disclosure with an influenza antiviral, including, for example, Oseltamivir. In certain embodiments, the combination therapy is effective against inflammation.

Further examples include the use of certain compounds of the disclosure in combination for the treatment of disease caused by *M. abscessus*, including, for example, macrolide sensitive *M. abscessus*. Certain compounds that may be useful in combination with compounds of this disclosure include one or more of the following: an aminoglycoside, a beta lactam, doxycycline, fluoroquinolone, and trimethoprim-sulfamethoxazole.

Further examples include the use of certain compounds of the disclosure in combination for the treatment of disease caused by *Babesia*. In certain embodiments, the disease is Babesosis. Certain compounds that may be useful in combination with compounds of this disclosure include one or more of the following: atovaquone, atovaquone-proguanil, tafenoquine, quinine, and pyrimethamine.

Further examples include the use of certain compounds of the disclosure in combination for the treatment of disease caused by *Toxoplasma*. In certain embodiments, the disease is toxoplasmosis. Certain compounds that may be useful in combination with compounds of this disclosure include one or more of the following: atovaquone, pyrimethamine, and trimethoprim-sulfamethoxazole.

Further examples include the use of certain compounds of the disclosure in combination for the treatment of disease caused by *Plasmodium*. Certain compounds that may be useful in combination with compounds of this disclosure include one or more of the following: a quinoline compound, including, for example, 8-aminoquinolines, 4-aminoquinolines, 4-quinoline alcohols, primaquine, tafenoquine, chloroquine, mefloquine, pyronaridine, lumefantrine, amodiaquine, quinine and quinidine; atovaquone; pyrimethamine; and an artemisinin.

Further examples include the use of certain compounds of the disclosure in combination for the treatment of a respiratory disease. Certain compounds that may be useful in combination with compounds of this disclosure include one or more of the following: a beta-lactam, a carbapenem, and a fluoroquinoline.

Further examples include the use of certain compounds of the disclosure in combination for the treatment of peptic ulcer disease. In certain embodiments, the treatment is provided to patients without risk factors for macrolide resistance. Certain compounds that may be useful in combination with compounds of this disclosure include one or more of the following: a proton pump inhibitor, including, for example, omeprazole, lansoprazole, dexlansoprazole, esomeprazole, pantoprazole, and rabeprazole; amoxicillin; and metronidazole.

Further examples include the use of certain compounds of the disclosure in combination for the treatment of a sexually transmitted disease. In certain embodiments, the sexually transmitted disease is caused by *N. gonorrhoeae*. In certain embodiments, the sexually transmitted disease is caused by *C. trachomatis*. In certain embodiments, the sexually transmitted disease is caused by *M. genitalium*. In certain embodiments, the sexually transmitted disease is lymphogranuloma venereum ("LGV"). Certain compounds that may be useful in combination with compounds of this disclosure include one or more of the following: a beta-lactam, including, for example, ceftriaxone; doxycycline; and fluoroquinoline.

Further examples include the use of certain compounds of the disclosure in combination for the treatment of an inflammatory disease. In certain embodiments, the inflammatory disease is a pelvic inflammatory disease. Certain compounds that may be useful in combination with compounds of this disclosure include metronidazole and metronidazole benzoate.

Further examples include the use of certain compounds of the disclosure in combination for the treatment of typhoid. Certain compounds that may be useful in combination with compounds of this disclosure include ceftriaxone and a beta lactam.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating infectious disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein, in combination with one or more additional agents for the treatment of infectious disorders.

In certain embodiments, the compounds, compositions, and methods disclosed herein may be coadministered with another therapeutic agent.

Besides being useful for human treatment, certain compounds and formulations disclosed herein may also be useful for veterinary treatment of companion animals, exotic animals and farm animals, including, for example, mammals, rodents, and the like. More preferred animals include horses, dogs, and cats.

LIST OF ABBREVIATIONS $^1$H NMR=Proton Nuclear Magnetic Resonance; ACN=MeCN=acetonitrile; Ac$_2$O=acetic anhydride; AcCl=acetyl chloride; AcOH=acetic acid; API=Active Pharmaceutical Ingredient; ASR=Analytical Service Report; AUC=Area under curve; ca.=Approximately; CD$_3$OD=deuterated methanol; CDCl$_3$=deuterated chloroform; cHex=cyclohexane; DCM=dichloromethane; DCM=Dichloromethane; DIEA=DIPEA; DMAP=4-dimethylamino-pyridine; DMF=N,N-dimethylformamide; DMSO=dimethyl sulfoxide; DMSO=Dimethyl sulfoxide; DMSO-d$_6$=deuterated dimethyl sulfoxide; DSC=Differential Scanning calorimetry; DVS=Dynamic Vapour Sorption; eq=Equivalents; Et$_2$O=diethyl ether; EtOAc=ethyl acetate; EtOAc=Ethyl acetate; EtOH=ethanol; EtOH=Ethanol; GVS=Gravimetric Vapour Sorption; h=hour; H$_2$O=Water; Hept=n-heptane; HPLC=High Performance Liquid Chromatography; HR=high resolution; IC=Ion Chromatography; ID=Identity; IP=Intellectual Property; IPA=2-Propanol; iPrOH=isopropanol; iPrOAc=isopropyl acetate; ISA=Ionic Strength Adjusted; KF=Karl Fischer; MDSC=Modulated Differential Scanning calorimetry; MeCN=Acetonitrile; MEK=Methyl ethyl ketone; MeOH=methanol; MeOH=Methanol; MIBK=Methyl isobutyl ketone; min=minute; MTBE=methyl tertiary butyl ether; N/A=Not Applicable; NMR=Nuclear Magnetic Resonance; No.=Number; PLM=Polarised Light Microscopy; PBS=phosphate buffered saline; PXRD=PXRD=X-Ray Powder Diffraction; Pyr=pyridine; RH=Relative Humidity; RT=room temperature; RT=Room Temperature; sat.=saturated; SEM=Scanning Electron Microscope; SGF=simulated gastric fluid; ss=saturated solution; TBME=tert-Butyl methyl ether; t-BuOH=tert-butanol; TEA=Et$_3$N; TFA=trifluoroacetic acid; TFAA=trifluoroacetic anhydride; TGA=Thermal Gravimetric Analysis; THF=Tetrahydrofuran; Tot=toluene; USP=United States Pharmacopeia; UV=Ultraviolet; vol=Volumes; VT-PXRD=Variable Temperature X-Ray Powder Diffraction.

Example 1: Cethromycin

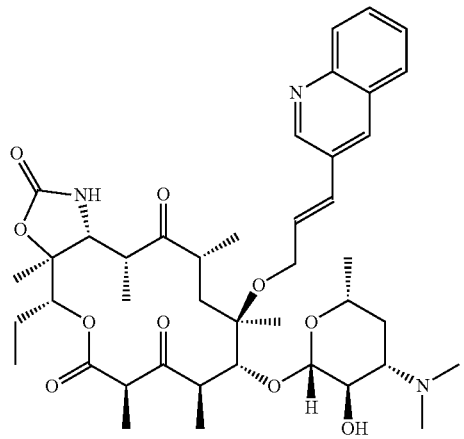 [SMILES: CC[C@H]1OC(=O)[C@H](C)C(=O)[C@H](C)[C@@H](O[C@@H]2O[C@H](C)C[C@H](N(C)C)[C@H]2O)[C@](C)(OC/C=C/c2cnc3ccccc3c2)C[C@@H](C)C(=O)[C@H](C)[C@H]2NC(=O)O[C@@]21C]

Cethromycin has chemical name (3aS,4R,7R,9R,10R,11R,13R,15R,15aR)-10-(((2S,3R,4S,6R)-4-(dimethylamino)-3-hydroxy-6-methyltetrahydro-2H-pyran-2-yl)oxy)-4-ethyl-3a,7,9,11,13,15-hexamethyl-11-(((E)-3-(quinolin-3-yl)allyl)oxy)octahydro-2H-[1]oxa-cyclotetradecino[4,3-d]oxazole-2,6,8,14(1H,7H,9H)-tetraone, formula C$_{42}$H$_{59}$N$_3$O$_{10}$, molar mass 765.95 g/mol and is commercially available. PXRD (not shown) gave no evidence of crystallinity. The $^1$H NMR in DMSO-d$_6$ solution for the compound as supplied is shown in FIG. 1.

Figure 2:
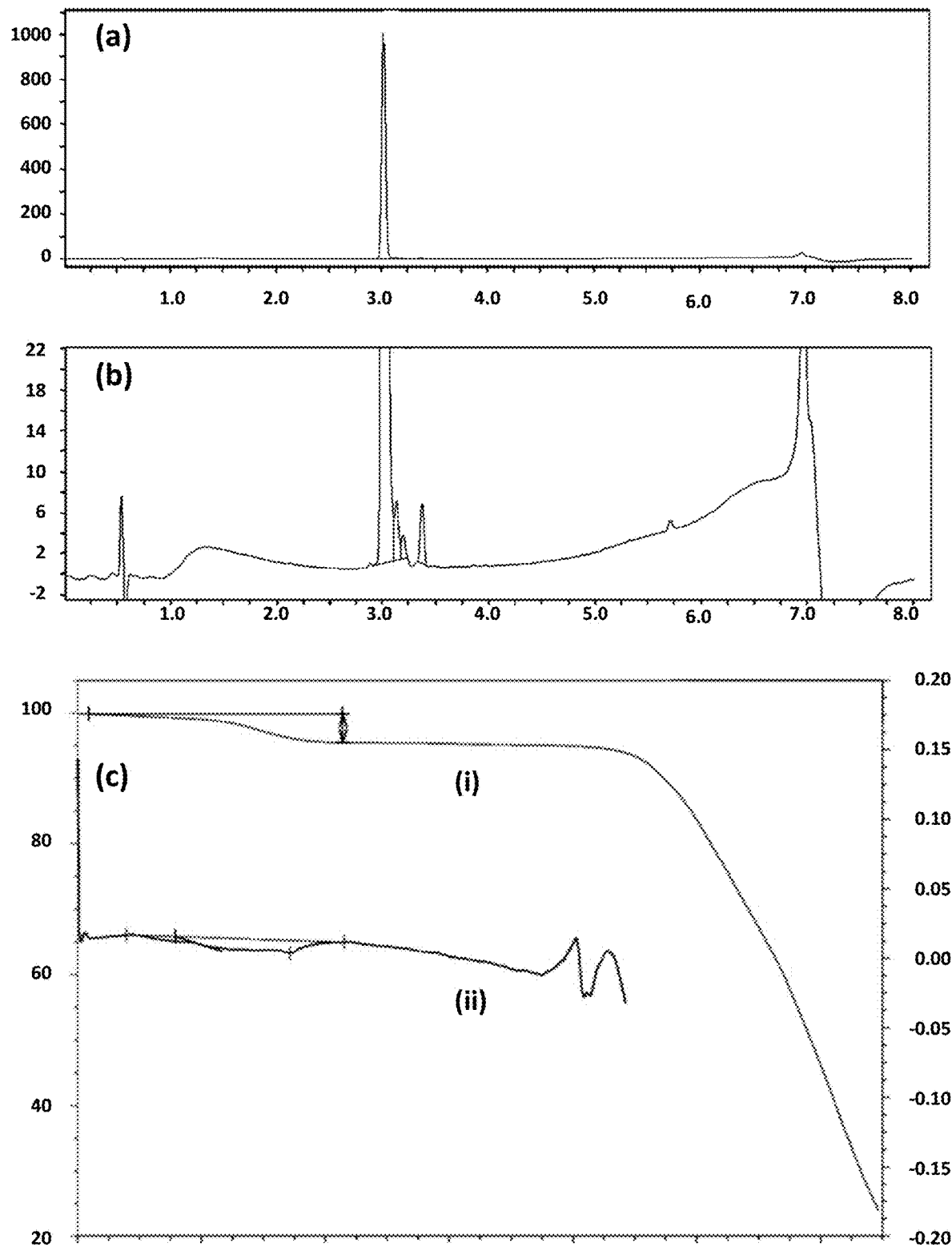
FIG. 2 shows HPLC and thermal analysis of cethromycin as supplied. (a) Full scale and (b) expanded HPLC. (c) Thermal analysis: (i) 4.5% weight loss; (ii) heat flow (right scale, W/g).

FIG. 2 shows HPLC and thermal analysis of cethromycin: (a) full scale and (b) expanded HPLC. From the HPLC analysis, cethromycin as supplied was >98% pure. (c) Thermal analysis: left axis and (i): weight during heating (% of original weight); right axis and (ii) heat flow (right scale, W/g). The weight loss from 25° C. to about 125° C. represents loss of about 4.5% of original weight.

Figure 3:
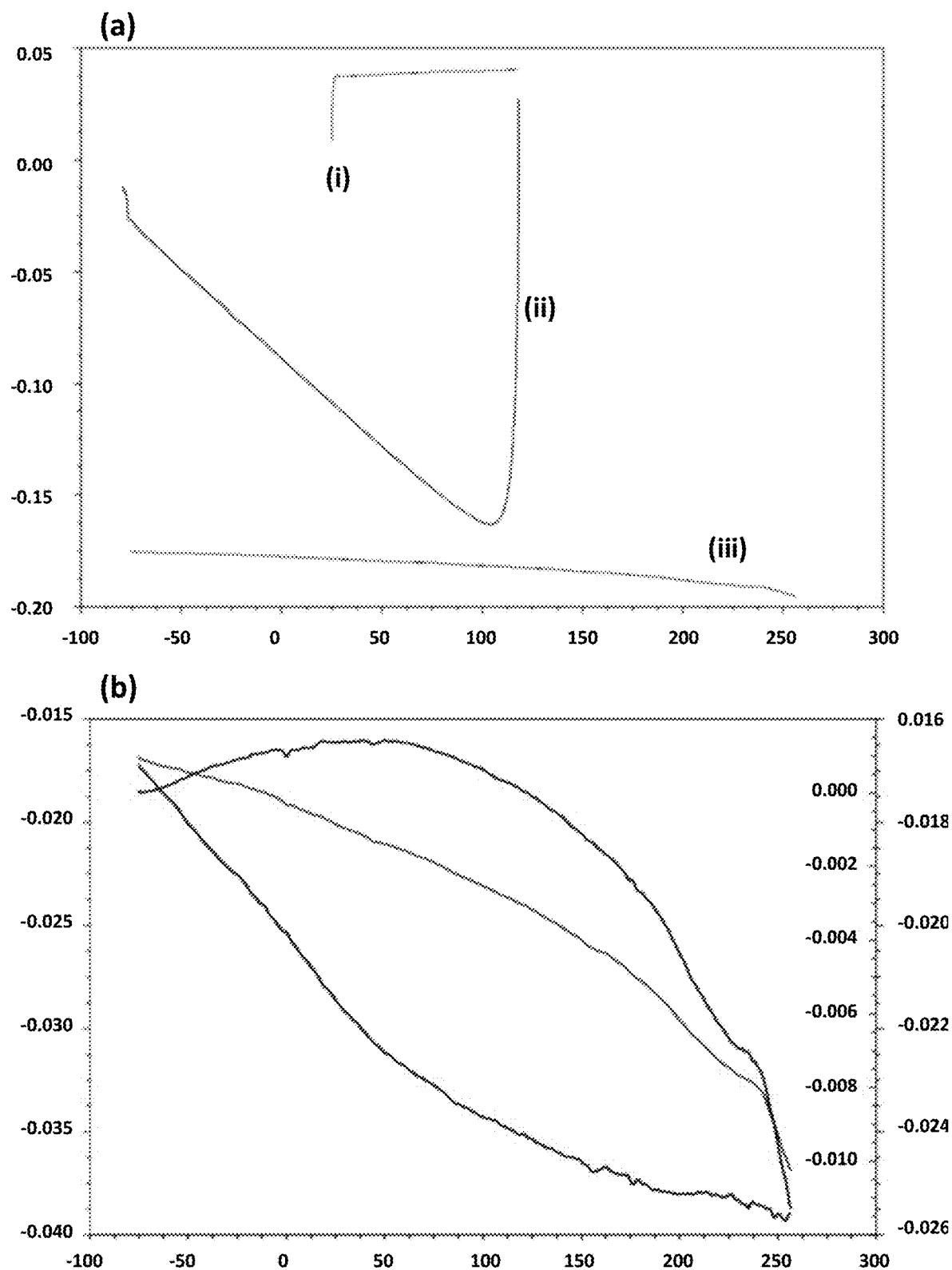
FIG. 3 shows modulated DSC of cethromycin as supplied.

FIG. 3 shows modulated DSC of cethromycin: (a) (i) heat from RT to 120° C.; cool to −80° C.; (iii) modulated heat to 260° C.; horizontal axis=temp (° C.); vertical axis=heat flow (W/g).

Figure 4:
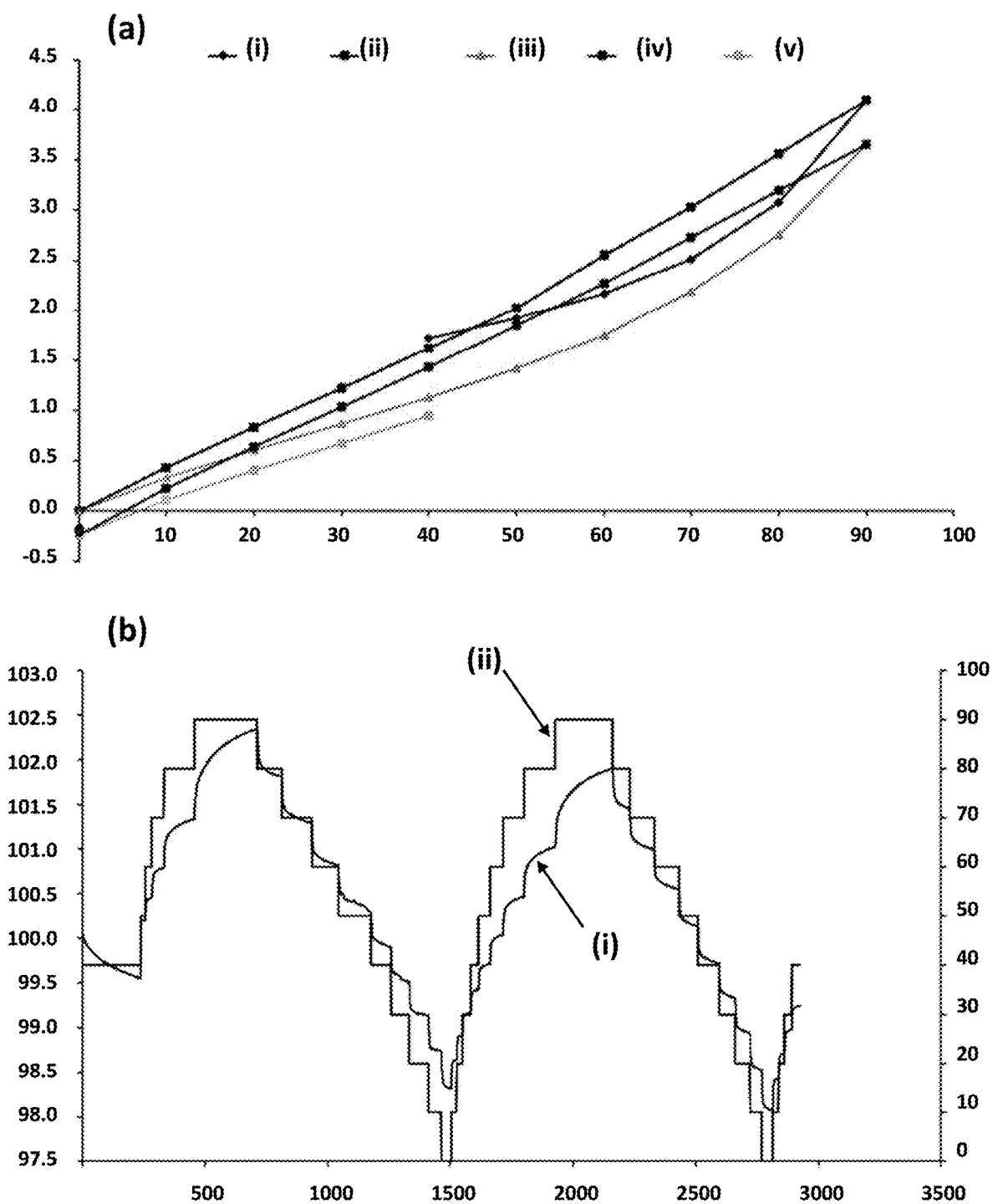
FIG. 4 shows GVS behavior for cethromycin in (a) isotherm and (b) kinetic format.

FIG. 4 shows GVS behavior for cethromycin in (a) isotherm and (b) kinetic format. (a): horizontal axis=target RH (%); vertical axis=change in mass (%); (i) cycle 1 sorp; (ii) cycle 1 desorp; (iii) cycle 2 sorp; (iv) cycle 2 desorp; (v) cycle 3 sorp. (b) horizontal axis=time (min); left axis and (i)=change in mass (%); right axis and (ii)=target RH (%). Powder XRD of the cethromycin sample before and after the DSC experiment displayed no sign of crystallinity (not shown).

Example 2: Methods

Powder X-Ray Diffraction ("PXRD")

Certain XRPD diffractograms were collected on a Bruker AXS C2 GADDS diffractometer using Cu Kα radiation (40 kV, 40 mA), an automated XYZ stage, a laser video microscope for auto-sample positioning and a Vantec-500 2-dimensional area detector. X-ray optics consists of a single Göbel multilayer mirror coupled with a pinhole collimator of 0.3 mm.

The beam divergence, i.e. the effective size of the X-ray beam on the sample, was approximately 4 mm. A θ-θ continuous scan mode was employed with a sample-detector distance of 20 cm which gives an effective 2θ range of 1.5°-32.5°. Typically, the sample was exposed to the X-ray beam for 120 seconds. The software used for data collection and analysis was GADDS for Win7/XP and Diffrac Plus EVA respectively.

For variable temperature (VT-XRPD) experiments samples were mounted on an Anton Paar DHS 900 hot stage at ambient conditions. The sample was then heated to the appropriate temperature at 20° C./min and subsequently held isothermally for 1 minute before data collection. Samples were prepared and analysed on a silicon wafer mounted to the hot stage using a heat-conducting paste.

XRPD diffractograms were collected on a Bruker D8 diffractometer using Cu K☐ radiation (40 kV, 40 mA) and a θ-2θ goniometer fitted with a Ge monochromator. The incident beam passes through a 2.0 mm divergence slit followed by a 0.2 mm anti-scatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively.

Samples were run under ambient conditions as flat plate specimens using powder as received. The sample was prepared on a polished, zero-background (510) silicon wafer by gently pressing onto the flat surface or packed into a cut cavity. The sample was rotated in its own plane.

Certain XRPD diffractograms were collected on a PANalytical Empyrean diffractometer using Cu Kα radiation (45 kV, 40 mA) in transmission geometry. A 0.5° slit, 4 mm mask and 0.04 rad Soller slits with a focusing mirror were used on the incident beam. A PIXcel3D detector, placed on the diffracted beam, was fitted with a receiving slit and 0.04 rad Soller slits. The software used for data collection was X'Pert Data Collector using X'Pert Operator Interface. The data were analysed and presented using Diffrac Plus EVA or HighScore Plus.

Samples were prepared and analysed in either a metal or Millipore 96 well-plate in transmission mode. X-ray transparent film was used between the metal sheets on the metal well-plate and powders (approximately 1-2 mg) were used as received. The Millipore plate was used to isolate and analyse solids from suspensions by adding a small amount of suspension directly to the plate before filtration under a light vacuum. The scan mode for the metal plate used the gonio scan axis, whereas a 2θ scan was utilised for the Millipore plate.

$^1$H NMR $^1$H NMR spectra were collected on a Bruker 400 MHz instrument equipped with an auto-sampler and controlled by a DRX400 console. Samples were prepared in DMSO-d$_6$ solvent, unless otherwise stated. Automated experiments were acquired using ICON-NMR configuration within Topspin software, using standard Bruker-loaded experiments. Off-line analysis was performed using ACD Spectrus Processor.

Differential Scanning Calorimetry ("DSC")

Certain DSC data were collected on a TA Instruments Q2000 equipped with a 50 position auto-sampler. Typically, 0.5-3 mg of each sample, in a pin-holed aluminium pan, was heated at 10° C./min from 25° C. to up to 250° C. A purge of dry nitrogen at 50 ml/min was maintained over the sample.

Modulated temperature DSC was carried out using an underlying heating rate of 2° C./min and temperature modulation parameters of ±0.636° C. (amplitude) every 60 seconds (period). The instrument control software was Advantage for Q Series and Thermal Advantage and the data were analysed using Universal Analysis or TRIOS.

Certain DSC data were collected on a TA Instruments Discovery DSC equipped with a 50 position auto-sampler. Typically, 0.5-3 mg of each sample, in a pin-holed aluminium pan, was heated at 10° C./min from 25° C. to 300° C. A purge of dry nitrogen at 50 ml/min was maintained over the sample. The instrument control software was TRIOS and the data were analysed using TRIOS or Universal Analysis.

Thermogravimetric Analysis ("TGA")

TGA data were collected on a TA Instruments Discovery TGA, equipped with a 25 position auto-sampler. Typically, 5-10 mg of each sample was loaded onto a pre-tared aluminium DSC pan and heated at 10° C./min from ambient temperature to up to 350° C. A nitrogen purge at 25 ml/min was maintained over the sample. The instrument control software was TRIOS and the data were analysed using TRIOS or Universal Analysis.

Gravimetric Vapor Sorption ("GVS")

Sorption isotherms were obtained using a SMS DVS Intrinsic moisture sorption analyser, controlled by DVS Intrinsic Control software. The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change, (mass relaxation) of the sample as a function of % RH was constantly monitored by a microbalance (accuracy±0.005 mg).

Typically, 5-30 mg of sample was placed in a tared mesh stainless steel basket under ambient conditions. The sample was loaded and unloaded at 40% RH and 25° C. (typical room conditions). A moisture sorption isotherm was performed as outlined below (2 scans per complete cycle). The standard isotherm was performed at 25° C. at 10% RH intervals over a 0-90% RH range. Typically, a double cycle (4 scans) was carried out. Data analysis was carried out within Microsoft Excel using the DVS Analysis Suite.

Karl Fischer ("KF") Titration

The water content of each sample was measured on a Metrohm 874 Oven Sample Processor at 150° C. with 851 Titrano Coulometer using Hydranal Coulomat AG oven reagent and nitrogen purge. Weighed solid samples were introduced into a sealed sample vial. Approximately 10 mg of sample was used per titration and duplicate determinations were made. An average of these results is presented unless otherwise stated. Data collection and analysis were performed using Tiamo software.

Ion Chromatography ("IC")

Data were collected on a Metrohm 930 Compact IC Flex with 858 Professional autosampler and 800 Dosino dosage unit monitor, using IC MagicNet software. Accurately weighed samples were prepared as stock solutions in a suitable solvent. Quantification was achieved by comparison with standard solutions of known concentration of the ion being analysed. Analyses were performed in duplicate and an average of the values is given unless otherwise stated. Analytical methods for cations and anions are provided in Tables 1 and 2, respectively.

TABLE 1

IC method for cation chromatography.

| Parameter | Value |
|---|---|
| Type of method | Cation exchange |
| Column | Metrosep C 4-250 (4.0 × 250 mm) |

TABLE 1-continued

IC method for cation chromatography.

| Parameter | Value |
|---|---|
| Column Temperature (° C.) | Ambient |
| Injection (μl) | Various |
| Detection | Conductivity detector |
| Flow Rate (ml/min) | 0.9 |
| Eluent | 1.7 mM HNO$_3$ 0.7 mM dipicolinic acid in a 5% acetone aqueous solution. |

TABLE 2

IC method for anion chromatography.

| Parameter | Value |
|---|---|
| Type of method | Anion exchange |
| Column | Metrosep A Supp 5-150 (4.0 × 150 mm) |
| Column Temperature (° C.) | Ambient |
| Injection (μl) | Various |
| Detection | Conductivity detector |
| Flow Rate (ml/min) | 0.7 |
| Eluent | 3.2 mM Na$_2$CO$_3$ 1.0 mM NaHCO$_3$ in a 5% acetone aqueous solution. |

High Performance Liquid Chromatography ("HPLC")

Purity analysis was performed on an Agilent HP1100/Infinity II 1260 series system equipped with a diode array detector and using OpenLAB software. The full method details are provided in Table 3.

TABLE 3

HPLC parameters.

| Parameter | Value |
|---|---|
| Type of method | Reverse phase with gradient elution |
| Sample Preparation | 0.2-0.5 mg/ml in acetonitrile:water 1:1 |
| Column | Supelco Ascentis Express C18 2.7 μm; 100 × 4.6 mm |
| Column Temperature (° C.) | 25 |
| Injection (μl) | 5 |
| Detection: Wavelength, Bandwidth (nm) | 255, 90 |
| Flow Rate (ml/min) | 2 |
| Phase A | 0.1% TFA in water |
| Phase B | 0.085% TFA in acetonitrile |

| | Time (min) | % Phase A | % Phase B |
|---|---|---|---|
| Timetable | 0 | 95 | 5 |
| | 6 | 5 | 95 |
| | 6.2 | 95 | 5 |
| | 8 | 95 | 5 |

Example 3: Preliminary Solubility Investigation

The following acid solutions were used for the study of salt formation. Where indicated, the acid was added as a solid directly to the reaction mixture.

Amorphous cethromycin (25 mg) in HPLC vials was treated with increasing volumes of solvent until the material fully dissolved or until a maximum of 60 vol (1.5 ml) had been added. After each addition of solvent, the vials were stirred and gently heated to 50° C. before the addition of a new aliquot of solvent. After the assessment was complete, ca. 1 eq. of HCl was added at 50° C. and the samples were slowly cooled to 5° C. at 0.1° C./min. All solids were then isolated by filtration and dried under suction. Antisolvent (n-heptane, 10 or 20 vol) was added to any solutions and the resulting gums were matured in a chamber switching from 25° C. to 50° C. every four hours. All isolated solids were analysed by PXRD.

Cethromycin was readily soluble in in 10 vol of THF:H$_2$O (9:1), 2-propanol, EtOH, EtOAc, acetone, MeCN, THF, TBME and DCM, with n-heptane identified as an antisolvent. Following the preliminary salt formation experiment, no crystalline solids were obtained. Based on the solubility results, EtOAc and acetone were selected as the solvents for the salt formation experiments, as well as methanol.

TABLE 4

Observations from solubility studies.

| Solvent | Volumes of solvent | | | | | | HCl at 50° C. | HCl addition |
|---|---|---|---|---|---|---|---|---|
| | 10 | 20 | 30 | 40 | 50 | 60 | | |
| THF:H$_2$O (9:1) | ✓ | — | — | — | — | — | (a) | (b) |
| 2-Propanol | ✓ | — | — | — | — | — | (a) | (b) |
| EtOH | ✓ | — | — | — | — | — | (a) | (b) |
| EtOAc | ✓ | — | — | — | — | — | (a) | (b) + (c) |
| Acetone | ✓ | — | — | — | — | — | (a) | (b) |
| MeCN | ✓ | — | — | — | — | — | (a) | (b) |
| THF | ✓ | — | — | — | — | — | (a) | (c) |
| Hept | x | x | x | x | x | x | (d) | (d) |
| TBME | ✓ | — | — | — | — | — | (a) | (c) |
| DCM | ✓ | — | — | — | — | — | (a) | (b) |

(✓ = clear solution obtained; x = suspension)

(a) clear colourless solution (b) very pale-yellow solution (c) very pale-yellow gum (d) white suspension Example 4: Preliminary Investigation of Salt Formation Cethromycin was treated with 18 different acids covering a range of pKa values in order to identify if it is possible to prepare cethromycin salts and if any of these salts exhibit favorable properties over the freebase.

TABLE 5

Acid solutions used for salt formation studies.

| Counter-ion/Coformer | Abbrev. | Concentration | Solvent |
|---|---|---|---|
| Hydrochloric acid | HCl | 1M | THF |
| Sulfuric acid | SO$_4$ | 1M | THF |
| Methane sulfonic acid | MSA | 1M | THF |
| p-Toluene sulfonic acid | pTSA | 1M | THF |
| Benzene sulfonic acid | BSA | 1M | THF |
| Oxalic acid | OXA | 1M | THF |
| Maleic acid | MEA | 1M | THF |
| Phosphoric acid | PHOA | 1M | THF |
| 2,5-Dihydroxybenzoic acid | DHBA | (a) | N/A |

TABLE 5-continued

Acid solutions used for salt formation studies.

| Counter-ion/Coformer | Abbrev. | Concentration | Solvent |
|---|---|---|---|
| Tartaric acid | TAR | 1M | THF |
| Fumaric acid | FUA | 0.5M | 1:1 MeOH:THF |
| Mucic acid | MUCA | (a) | N/A |
| Citric acid | CA | 1M | THF |
| Malic acid | MA | 1M | THF |
| Hippuric acid | HPA | (a) | N/A |
| Benzoic acid | BA | (a) | N/A |
| Succinic acid | SUCA | 1M | THF |
| Acetic acid | AcOH | 1M | THF |

(a) added as a solid

Amorphous cethromycin (25 mg) was dissolved in 10 vol (250 μl) of one of three solvents (MeOH, acetone and EtOAc) at 50° C. The solutions were then treated with the selected 18 different counter-ions (Table 5) for a total of 54 samples. The resulting solutions/suspensions/gums were then cooled down to 5° C. at 0.1° C./min and were held at 5° C. for 4 hr. Stirring was maintained throughout. Any remaining solutions were evaporated at ambient conditions by uncapping the vials. Antisolvent, (heptane, 10 vol) was added to any resulting gums/oils, which were then matured in a chamber cycling from 25° C. to 50° C. every 4 hr. Any pastes obtained were dried by spreading on a microscope slide. Any solids obtained were filtered/isolated and initially analysed by PXRD. All solids that displayed new PXRD diffractograms were isolated and characterised further. Any solids that were amorphous or consistent with the starting materials were matured between 25-50° C. for 14 days. Solids were then isolated and analysed by PXRD.

The results of the salt formation experiments on cethromycin are summarised in Tables 6, 7, and 8 (key follows). Three distinct salt forms for cethromycin with phosphoric acid, acetic acid, and hydrochloric acid were observed, named respectively as phosphate pattern 1, acetate pattern 1, and chloride pattern 1.

TABLE 6

Salt formation experiments in methanol.

| Acid | After acid addition | After cooling | After evaporation | After addition of antisolvent | Maturation of gums/oils |
|---|---|---|---|---|---|
| HCl | (b) | (b) | (g) | (g) | (g) |
| SO$_4$ | (b) | (b) | (g) | (g) | (g) |
| MSA | (b) | (b) | (h) | (h) | (h) |
| pTSA | (a) | (a) | (e) | (f) | (e) |
| BSA | (b) | (b) | (f) | (f) | (h) |
| OXA | (a) | (a) | (f) | (f) | (h) |
| MEA | (a) | (a) | (f) | (f) | (f) |
| PHOA | (a) | (a) | (f) | (f) | (f) |
| DHBA | (a) | (a) | (f) | (f) | (i) |
| TAR | (a) | (a) | (f) | (f) | (m) |
| FUA | (a) | (a) | (f) | (f) | (k) |
| MUCA | (a) + (c) | (d) | — | — | — |
| CA | (a) | (a) | (f) | (f) | (k) |
| MA | (a) | (a) | (f) | (f) | (e) |
| HPA | (a) | (a) | (f) | (f) | (e) |
| BA | (a) | (a) | (f) | (f) | (e) |
| SUCA | (a) | (a) | (f) | (f) | (e) |
| AcOH | (a) | (a) | (f) | (f) | (e) |

TABLE 7

Salt formation experiments in acetone.

| Acid | After acid addition | After cooling | Treatment 1 | Outcome | Treatment 2 | Outcome | PXRD |
|---|---|---|---|---|---|---|---|
| HCl | (b) | (b) | (I) | (n) | (n) | (h) + (n) | N/A |
| SO4 | (a) + (n) | (a) + (n) | (II) | (j) | N/A | N/A | amorphous |
| MSA | (b) | (b) | (I) | (n) | (n) | (h) | amorphous |
| pTSA | (b) | (b) | (I) | (k) | (k) | (h) + (l) | amorphous |
| BSA | (b) | (b) | (I) | (n) | (n) | (h) + (l) | amorphous |
| OXA | (a) | (a) | (I) | (k) | (k) | (h) | amorphous |
| MEA | (a) | (a) | (I) | (k) | (k) | (h) + (l) | N/A |
| PHOA | (a) + (n) | (o) | (III) | N/A | N/A | N/A | phosphate pattern 1 |
| DHBA | (a) | (a) | (I) | (n) | (n) | (h) + (n) | N/A |
| TAR | (a) + (h) | (a) + (h) | (II) | (k) | (k) | (h) | amorphous |
| FUA | (a) | (a) | (I) | (k) | (k) | (h) + (m) | N/A |
| MUCA | (p) | (p) | (IV) | N/A | N/A | N/A | N/A |
| CA | (a) | (a) | (I) | (k) | (k) | (l) | N/A |
| MA | (a) | (a) | (I) | (k) | (k) | (l) | N/A |
| HPA | (a) | (a) | (I) | (k) | (k) | (m) | N/A |
| BA | (a) | (a) | (I) | (k) | (k) | (m) | N/A |
| SUCA | (a) | (a) | (I) | (k) | (k) | (m) | N/A |
| AcOH | (a) | (a) | (I) | (k) | (k) | (h) | acetate pattern 1 |

TABLE 8

Salt formation experiments in EtOAc.

| Acid | After acid addition | After cooling | Treatment 1 | Outcome | Treatment 2 | PXRD |
|---|---|---|---|---|---|---|
| HCl | (a) + (n) | (h) + (n) | (IV) | (h) | | chloride pattern 1 |
| SO4 | (a) + (n) | (n) | (V) | (i) + (n) | | amorphous |
| MSA | (a) + (n) | (n) | (V) | (h) + (n) | | amorphous |
| pTSA | (a) + (n) | (a) + (l) | (V) | (h) | | amorphous |
| BSA | (a) + (n) | (b) + (m) | (V) | (h) | | amorphous |
| OXA | (a) + (n) | (a) + (n) | (V) | (h) + (n) | | amorphous |
| MEA | (p) | (a) + (k) | (V) | (h) | | amorphous |
| PHOA | (a) + (n) | (n) + (o) | (VI) | (h) | | phosphate pattern 1 |
| DHBA | (n) | (a) + (n) | (V) | (h) | | amorphous |

TABLE 8-continued

Salt formation experiments in EtOAc.

| Acid | After acid addition | After cooling | Treatment 1 | Outcome | Treatment 2 | PXRD |
|---|---|---|---|---|---|---|
| TAR | (l) | (a) + (n) | (V) | (h) | | amorphous |
| FUA | (a) | (a) | (I) | (q) | | amorphous |
| MUCA | (a) | (p) | N/A | N/A | | N/A |
| CA | (m) | (a) + (n) | (V) | (h) | | amorphous |
| MA | (m) | (a) + (l) | (V) | (h) | | amorphous |
| HPA | (a) | (a) + (k) | (V) | (l) | (V) | N/A |
| BA | (a) | (a) | (I) | (l) | (V) | N/A |
| SUCA | (a) | (a) | (I) | (l) | (V) | N/A |
| AcOH | (a) | (a) | (I) | (l) | (V) | acetate pattern 1 |

(a) clear colorless solution
(b) pale yellow solution
(c) some undissolved acid
(d) amorphous white suspension
(e) clear colorless oil
(f) colorless oil
(g) yellow oil
(h) white solid
(i) off-white solid
(I) evaporated at ambient conditions
(II) mother liquor isolated and evaporated. Gum set aside.
(III) centrifuged
(j) yellow solid
(k) colorless gum
(l) white gum
(m) off-white gum
(n) pale yellow gum
(o) white paste
(p) white suspension
(q) glassy solid
(IV) filtered
(V) matured
(VI) paste isolated and dried on a microscope slide

TABLE 9

Characterisation of solids of interest.

| | | | | |
|---|---|---|---|---|
| Solvent | Acetone | Acetone | EtOAc | EtOAc |
| Counter ion | phosphate | acetate | acetate | chloride |
| PXRD | poorly crystalline, denoted phosphate pattern 1 | crystalline, denoted acetate pattern 1 | matches acetate pattern 1 | crystalline, denoted chloride pattern 1 |
| $^1$H NMR | peak shifts observed for —NMe$_2$; 0.6 eq. residual acetone; 0.7 eq. residual THF, no water peak. | trace amounts of acetone, 1 eq. acetic acid | N/A | Consistent # protons. Some shifting in peaks esp. for —NMe$_2$ indicating salt formation. Trace EtOAc |
| IC | 0.6 eq. phosphate observed | N/A | N/A | 1 eq |
| TGA | Gradual mass loss in TGA from ambient-difficult to define individual event, degradation onset ca. 200° C. | 1.8% mass loss from ambient to 70° C. (matches ca. 1 eq. water); 6.5% mass loss from 70° C. to 130° C. (matches ca. 1 eq. acetic acid) | Sample heated in TGA to obtained freebase pattern 1 (Section 9.1.3) | 5.7% mass loss from ambient to 100° C. (matches ca. 2.6 eq water); degradation onset ca. 210° C. |
| DSC | No events observed until 175° C. (broad endotherm starting, likely degradation) | Broad endotherm onset at 33.3° C. (14 J/g); endotherm onset at 117° C. (45 J/g); broad exotherm onset at 133.4° C. (12 J/g); endotherm at 162.8° C. (4 J/g); endotherm at 221.4° C. (49 J/g) | N/A | N/A |
| HPLC Purity | N/A | N/A | N/A | 98.5% |
| Further analysis | N/A | VT PXRD: amorphous by 130° C., crystallised by 170° C., form remained on cooling back to RT. | N/A | N/A |
| Assignment | Possible solvated hemi-phosphate salt | Possible mono hydrated mono-acetate salt. | Possible mono hydrated mono-acetate salt. | Mono HCl salt, possible hydrate. |

Salt formation experiments on cethromycin using 18 counter-ions in 3 different solvent systems (MeOH, acetone and EtOAc) were carried out. From these experiments four new patterns have been identified: phosphate pattern 1, acetate pattern 1, freebase pattern 1 and chloride pattern 1.

Figure 5:
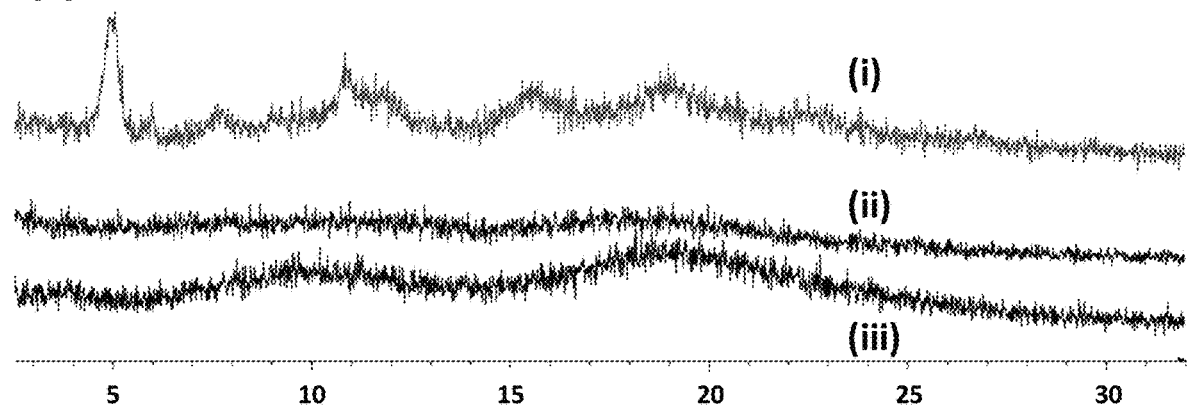
FIG. 5 shows the PXRD for products from salt formation experiments in acetone.
Figure 5:
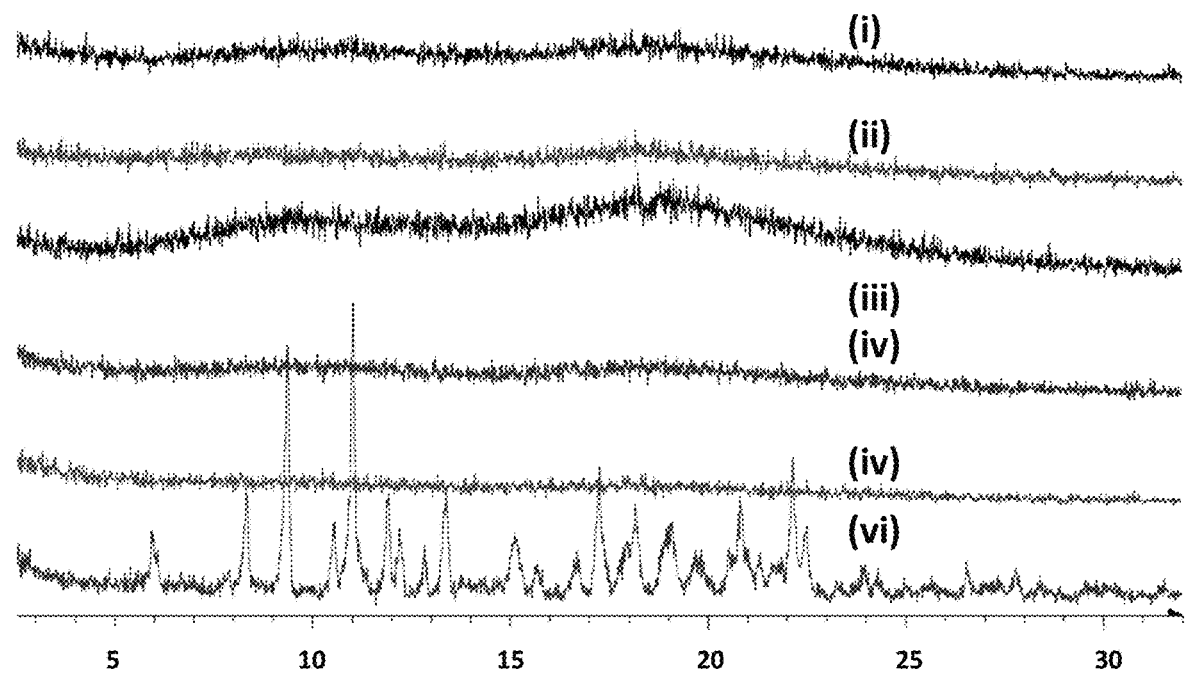

FIG. 5 shows the PXRD for products from salt formation experiments in acetone: (a) (i) cethromycin phosphate pattern 1 and (ii) SO4, and (iii) free base cethromycin; (b) (i) MSA, (ii) pTSA, (iii) BSA, (iv) OXA, (v) TAR, (vi) AcOH pattern 1, after maturing 14 days in n-heptane.

Figure 6:
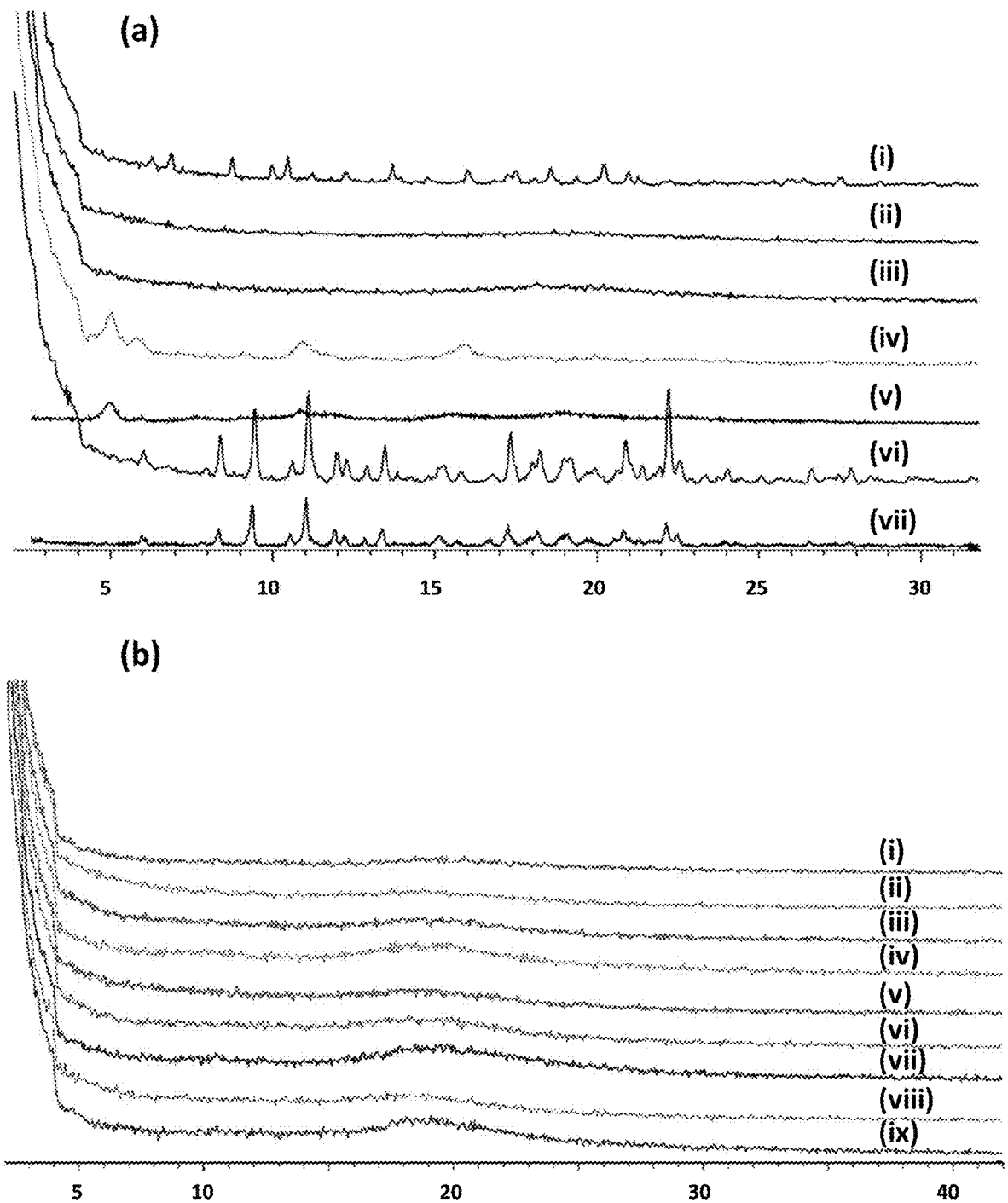
FIG. 6 shows the PXRD for products from salt formation experiments in EtOAc.

FIG. 6 shows the PXRD for products from salt formation experiments in EtOAc. (a) acetate pattern 1 (i) chloride pattern 1, (ii) MSA, (iii) pTSA; PHOA: (iv) experiment, (v) reference; acetate pattern 1: (vi) experiment, (vii) reference. (b) (i) SO4, (ii) BSA, (iii) OXA, (iv) MEA, (v) DHBA, (vi) TAR, (vii) FUA, (viii) CA, and (ix) MA.

Phosphate pattern 1 is a poorly crystalline form isolated from acetone and EtOAc, this was characterised as a potentially solvated hemi-phosphate salt. $^1$H NMR for phosphate pattern 1 (not shown) is substantially the same as that for freebase cethromycin.

Acetate pattern 1 is a crystalline solid isolated from salt formation experiments in both acetone and EtOAc after maturing the gum initially obtained in heptane. It is a mono acetate salt that is potentially monohydrated. $^1$H NMR for acetate pattern 1 (not shown) contains a peak at 81.9 for acetic acid, and is otherwise substantially the same as that for freebase cethromycin.

Chloride pattern 1 is a crystalline solid isolated from the EtOAc salt formation experiment via cooling to 5° C. $^1$H NMR for chloride pattern 1 (not shown) is substantially the same as that for freebase cethromycin. The sample contains only trace EtOAc by NMR but has a significant mass loss from ambient to 100° C. indicating that this form is hydrated.

Phosphate pattern 1, acetate pattern 1 and chloride pattern 1 were carried forward for scale up.

Figure 7:
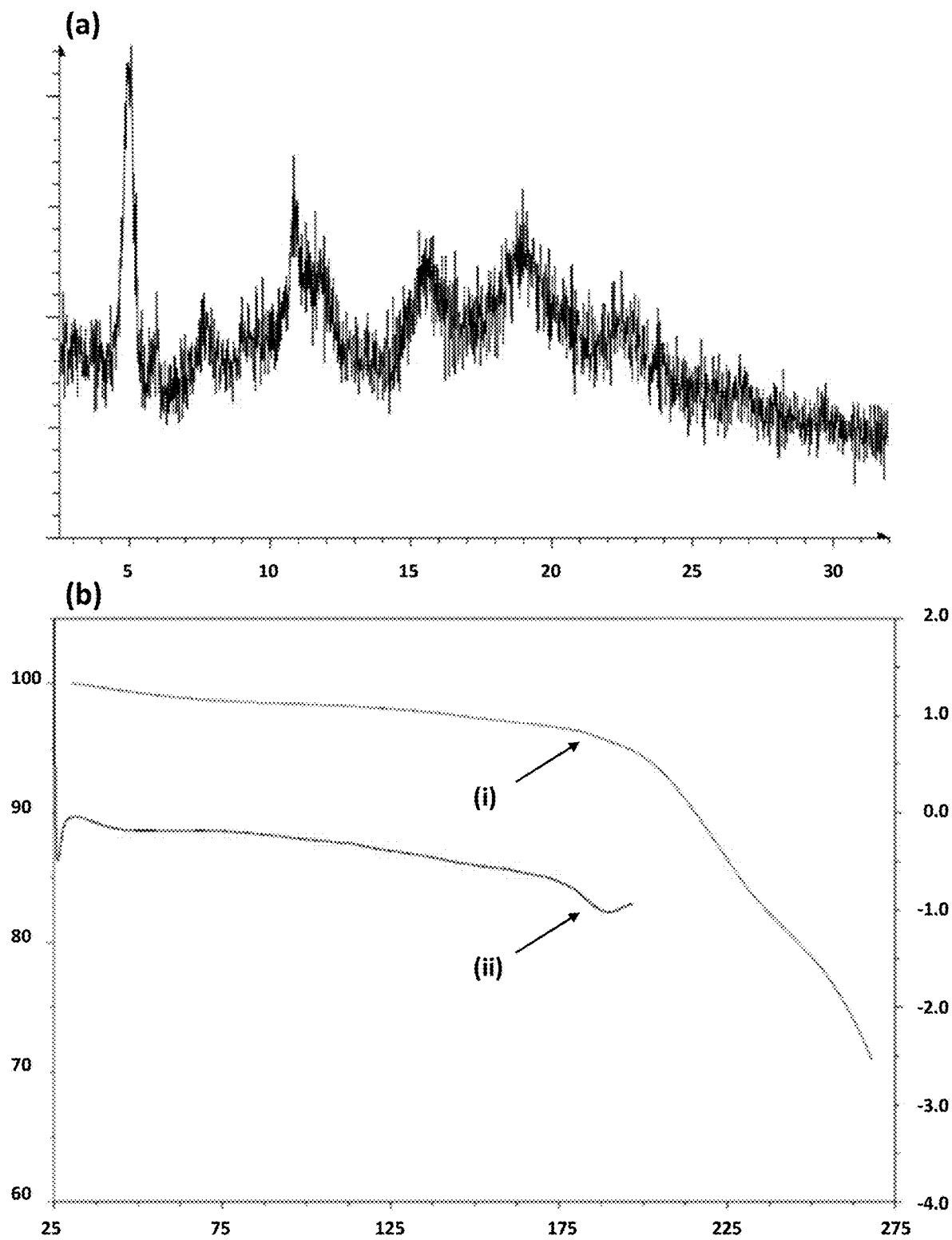
FIG. 7 shows PXRD and TGA characterization of phosphate pattern 1 from the salt formation experiments.

FIG. 7 shows PXRD and TGA characterization of phosphate pattern 1 from the salt formation experiments. (a) PXRD. (b) TGA, horizontal axis=temp (° C.), left axis and (i)=weight (%); right axis and (ii)=heat flow (W/g).

Figure 8:
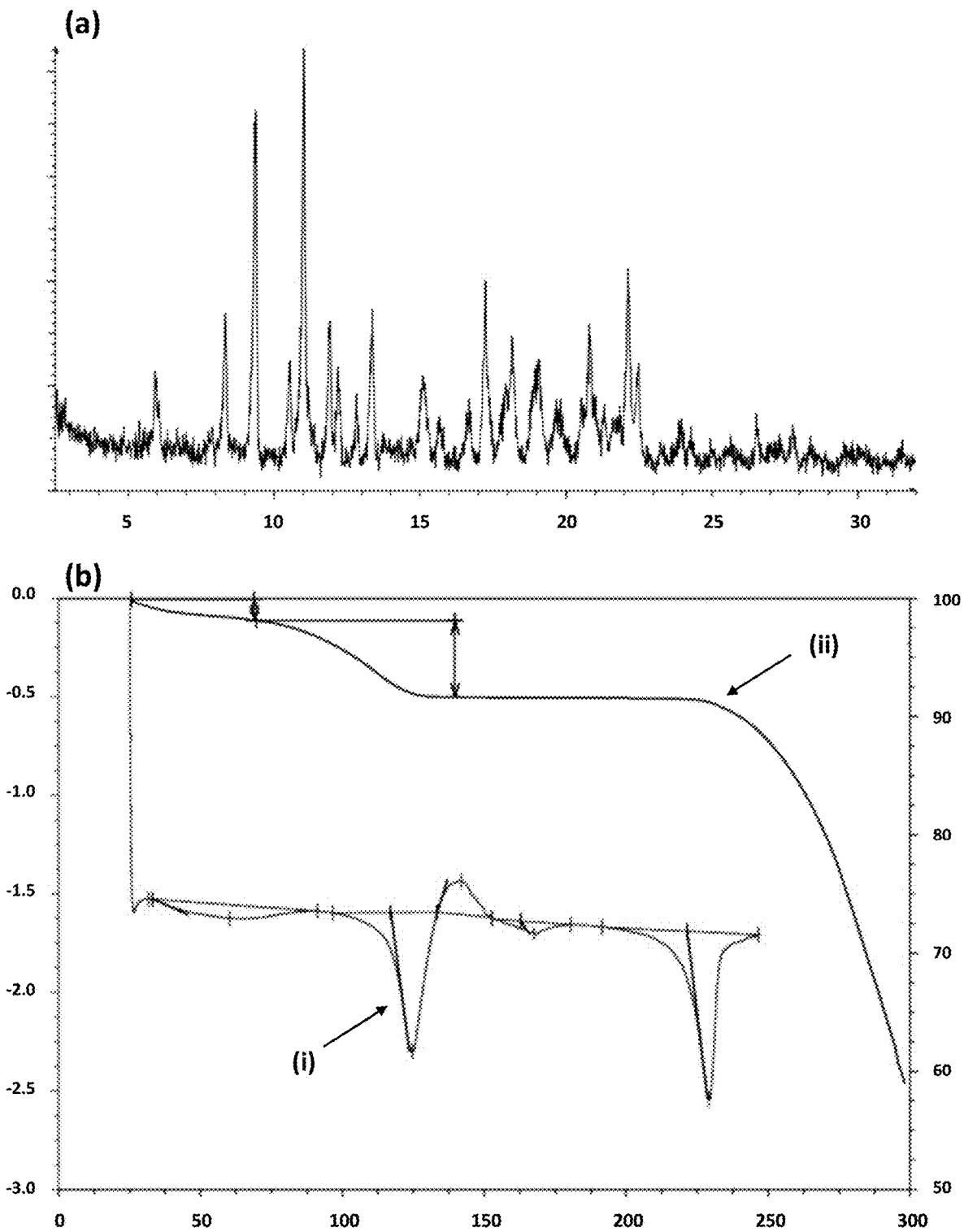
FIG. 8 shows PXRD and TGA characterization of acetate pattern 1 from the salt formation experiments.

FIG. 8 shows PXRD and TGA characterization of acetate pattern 1 from the salt formation experiments (a) PXRD. Peak information, from a related diffractogram, for the 20 most intense peaks is provided in Table 10. (b) TGA, horizontal axis=temp (° C.), left axis and (i)=heat flow (W/g); right axis and (ii)=weight (%); further details provided in Table 9.

TABLE 10

Peaks in the PXRD diffractogram for cethromycin acetate.

| 2θ, ° | d-spacing, Å | Intensity |
|---|---|---|
| 6.0 | 14.6 | 46 |
| 8.3 | 10.6 | 54 |
| 9.4 | 9.4 | 73 |
| 10.6 | 8.3 | 25 |
| 11.0 | 8.0 | 100 |
| 11.2 | 7.9 | 35 |
| 12.0 | 7.4 | 42 |
| 12.3 | 7.2 | 26 |
| 12.9 | 6.9 | 26 |
| 13.4 | 6.6 | 42 |
| 15.3 | 5.8 | 25 |
| 17.3 | 5.1 | 42 |
| 18.0 | 4.9 | 22 |
| 18.2 | 4.9 | 29 |

TABLE 10-continued

Peaks in the PXRD diffractogram for cethromycin acetate.

| 2θ, ° | d-spacing, Å | Intensity |
|---|---|---|
| 19.0 | 4.7 | 23 |
| 19.1 | 4.6 | 24 |
| 20.9 | 4.3 | 36 |
| 21.0 | 4.2 | 23 |
| 22.2 | 4.0 | 75 |
| 22.6 | 3.9 | 42 |

Figure 9:
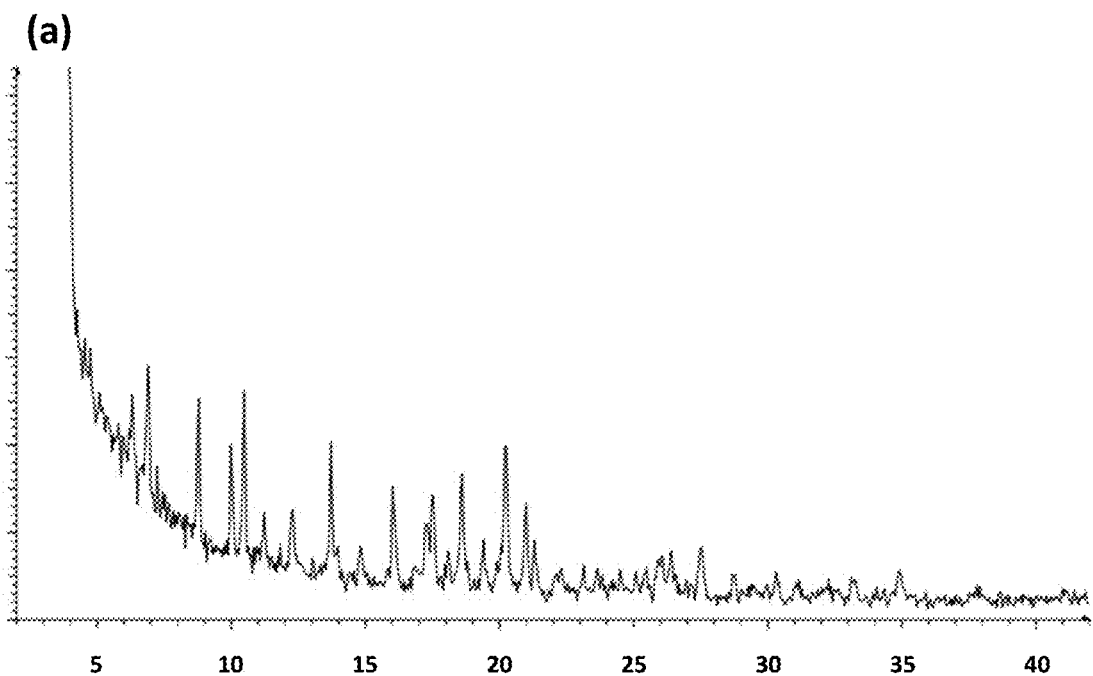
FIG. 9 shows PXRD and TGA characterization of chloride pattern 1 from the salt formation experiments.
Figure 9:
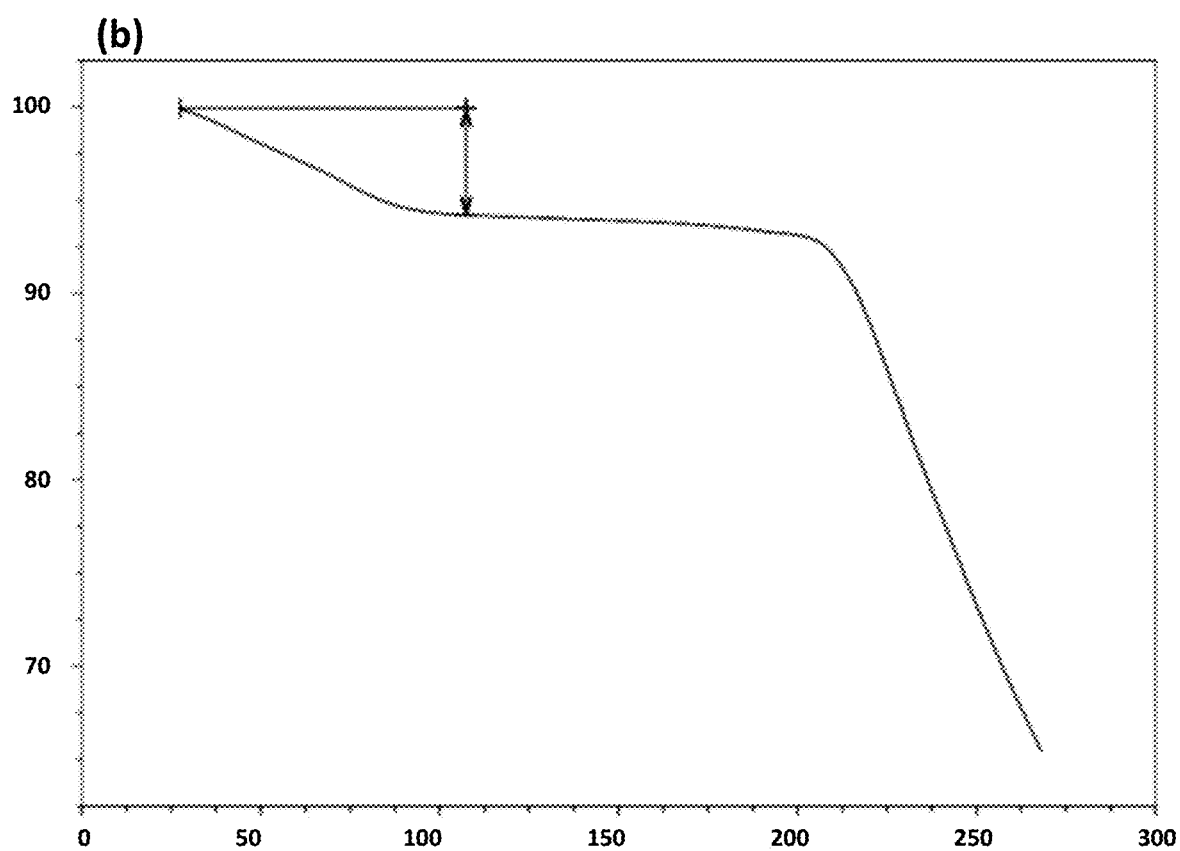

FIG. 9 shows PXRD and TGA characterization of chloride pattern 1 from the salt formation experiments. (a) PXRD. Peak information, from a related diffractogram, for the 20 most intense peaks is provided in Table 11. (b) TGA, horizontal axis=temp (° C.), vertical axis weight (%); 5.7% loss in mass upon heating to about 110° C.

TABLE 11 eaks in the PXRD diffractogram for cethromycin chloride pattern 1.

| 2θ, ° | d-spacing, Å | Intensity |
|---|---|---|
| 6.3 | 14.1 | 64 |
| 6.9 | 12.9 | 83 |
| 8.7 | 10.1 | 77 |
| 10.0 | 8.8 | 76 |
| 10.5 | 8.5 | 100 |
| 11.2 | 7.9 | 35 |
| 12.2 | 7.3 | 43 |
| 13.7 | 6.5 | 72 |
| 14.8 | 6.0 | 31 |
| 16.0 | 5.5 | 66 |
| 17.2 | 5.1 | 51 |
| 17.5 | 5.1 | 57 |
| 18.1 | 4.9 | 32 |
| 18.6 | 4.8 | 67 |
| 19.4 | 4.6 | 33 |
| 20.2 | 4.4 | 91 |
| 20.9 | 4.2 | 54 |
| 26.0 | 3.4 | 30 |
| 26.4 | 3.4 | 34 |
| 27.6 | 3.2 | 30 |

Example 5: Variable-Temperature PXRD

Figure 10:
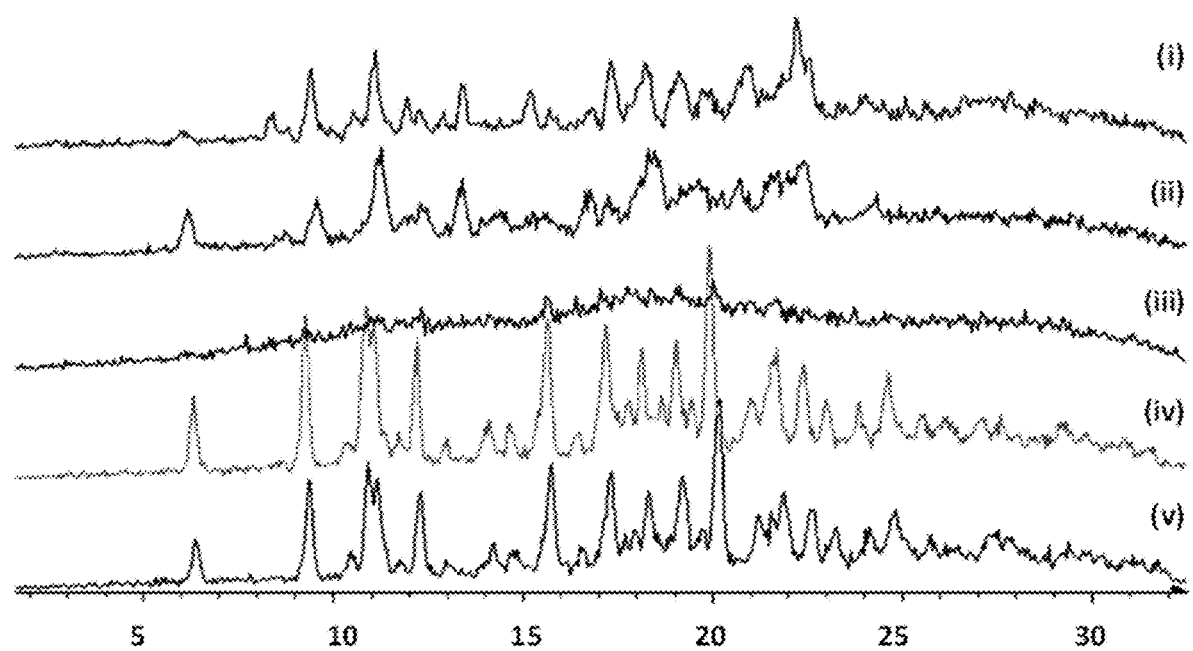
FIG. 10 shows a VT PXRD study for the conversion of acetate pattern 1 to freebase pattern 1.
Figure 11:
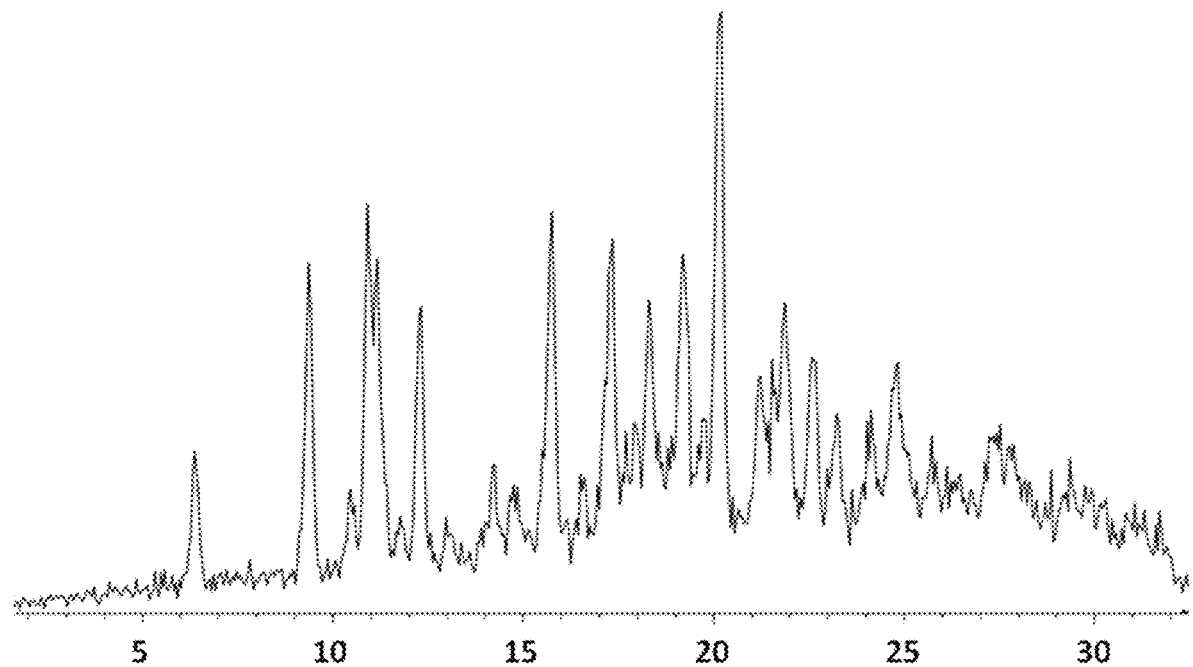
FIG. 11 shows PXRD for freebase pattern 1.

Thermal analysis of acetate pattern 1 showed a complex thermal profile. In order to investigate this further a VT PXRD experiment on this material was carried out. On heating, the original white powder converts first to a translucent solid by 130° C., then to a translucent white solid by 170° C. This conversion is accompanied by loss of the original diffraction pattern is lost and appearance of a new diffraction pattern. FIG. 10 follows the conversion process: (i) acetate pattern 1 at rt, followed by heating to (ii) 90° C., (iii) 130° C., and (iv) 170° C., and finally (v) cooling back to rt. $^1$H NMR analysis revealed that this material contained no acetic acid and thus the new diffraction pattern is ascribed to a freebase form, which is denoted freebase pattern 1. The material is stable at RT. FIG. 11 shows PXRD of freebase pattern 1.

Example 6: Investigation of Salt Formation Scaleup

Phosphate pattern 1 Scaleup Cethromycin (250.5 mg) was treated with 10 vol (2.5 ml) of EtOAc and warmed in a Polar Bear at 50° C. Phosphoric acid (1M THF stock solution (359

µl, 1 eq.) was added. A thick yellow gum was observed that appeared to lose particles with stirring. The sample was kept at 50° C. for 30 min and then slowly cooled at 0.1° C. per min to 5° C., resulting in a white paste with some yellow gum. The white material (120.3 mg) was isolated by filtration on a Büchner funnel. PXRD analysis of the white powder (not shown) revealed that the solid is very weakly crystalline.

Phosphate pattern 1 was weakly crystalline upon scale up, contains ca. 3 eq. of water and is most likely a hemi salt. It is 98.5% pure by HPLC and deliquesces under accelerated storage at 25° C./97% RH. The material is very hygroscopic with a mass uptake of 21.0% between 0% and 90% RH. The material manifests in the form of glassy shards.

Figure 12:
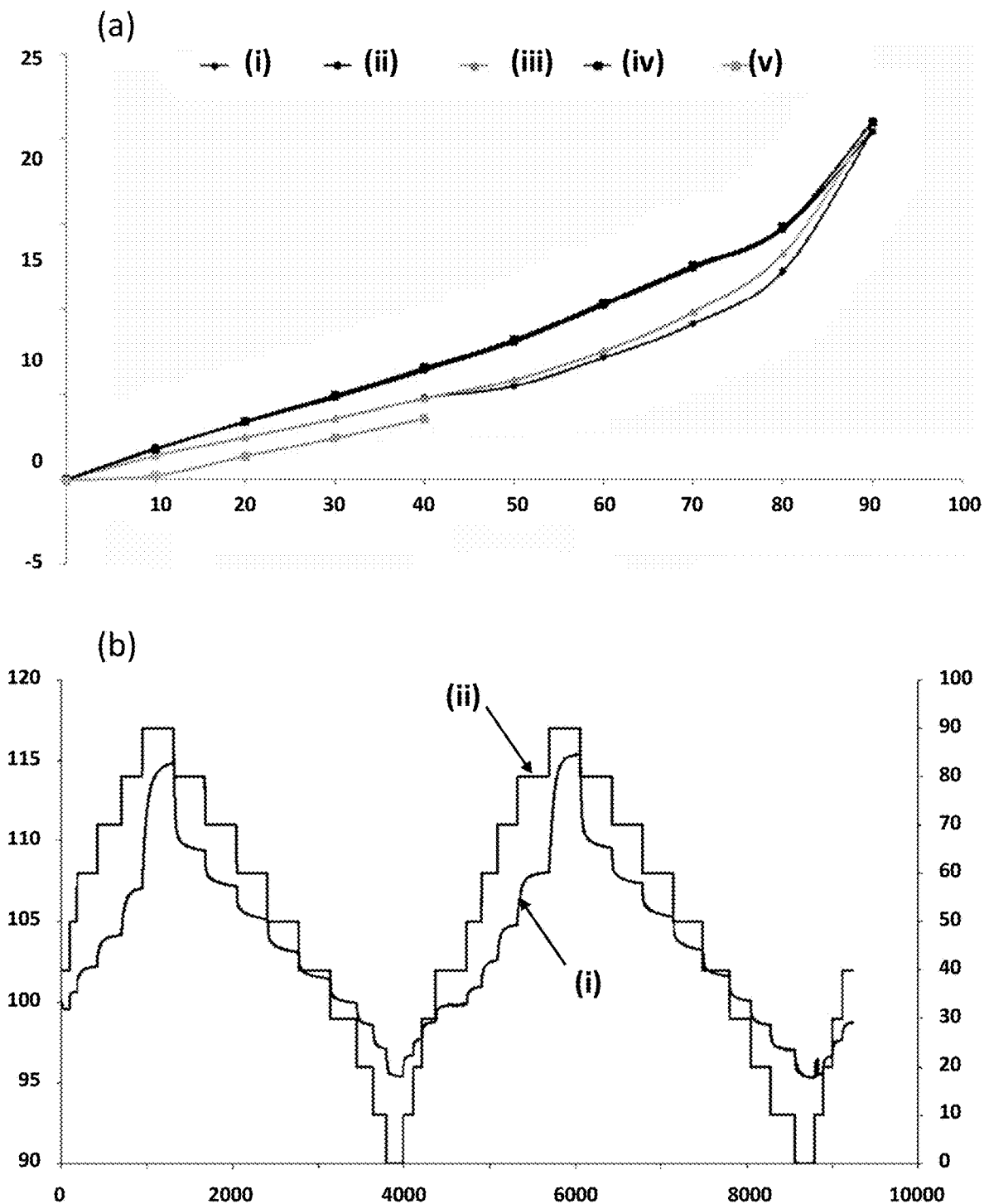
FIG. 12 shows GVS behavior for cethromycin phosphate pattern 1 in (a) isotherm and (b) kinetic format.

FIG. 12 shows GVS behavior for phosphate pattern 1 in (a) isotherm and (b) kinetic format. (a): horizontal axis=target RH (%); vertical axis=change in mass (%); (i) cycle 1 sorp; (ii) cycle 1 desorp; (iii) cycle 2 sorp; (iv) cycle 2 desorp; (v) cycle 3 sorp. (b) horizontal axis=time (min); left axis and (i)=change in mass (%); right axis and (ii)=target RH (%).

Due to its poor crystallinity, this material was not examined further.

Acetate pattern 1 Scaleup Cethromycin (250.0 mg) was treated with 10 vol (2.5 ml) of EtOAc and warmed in a Polar Bear at 50° C. Acetic acid (1M THF, 359 µl, 1 eq.) was added. The sample was kept at 50° C. for 30 mins and then slowly cooled at 0.1° C. per min to 5° C. This resulted in a clear colourless solution which was then evaporated under ambient conditions. This produced a very pale-yellow gum. This material was agitated with a spatula, treated with 10 vol heptane and matured for 2 days cycling from 25° C. to 50° C. every four hours. The resulting white suspension was isolated by filtration on a Büchner funnel yielding a white powder (228.4 mg).

Acetate pattern 1 is a hydrated mono salt and was isolated with 98.5% purity. The material is hygroscopic with a mass uptake of 8.6% between 0% and 90% RH and due to its hygroscopicity the water stoichiometry could not be determined. $^1$H NMR and PXRD for acetate pattern 1 scaleup (not shown) is substantially the same as that for the Example 4 acetate pattern 1 material.

Acetate pattern 1 possesses a complex thermal profile and loses acetic acid from ca. 130° C. and converts to freebase pattern 1. The sample also loses acetic acid at high humidity (accelerated storage conditions and GVS). Acetate pattern 1 was found to convert to convert to a new form, termed acetate pattern 2, by subjection of the material to GVS conditions or storage at 40° C./75% RH. Acetate pattern 2 was proven to have lower acetate content although it remained unchanged at 97% RH. Due to the apparent dissociation to the freebase upon heating, further investigation of the compound's thermal profile was not performed.

Figure 13:
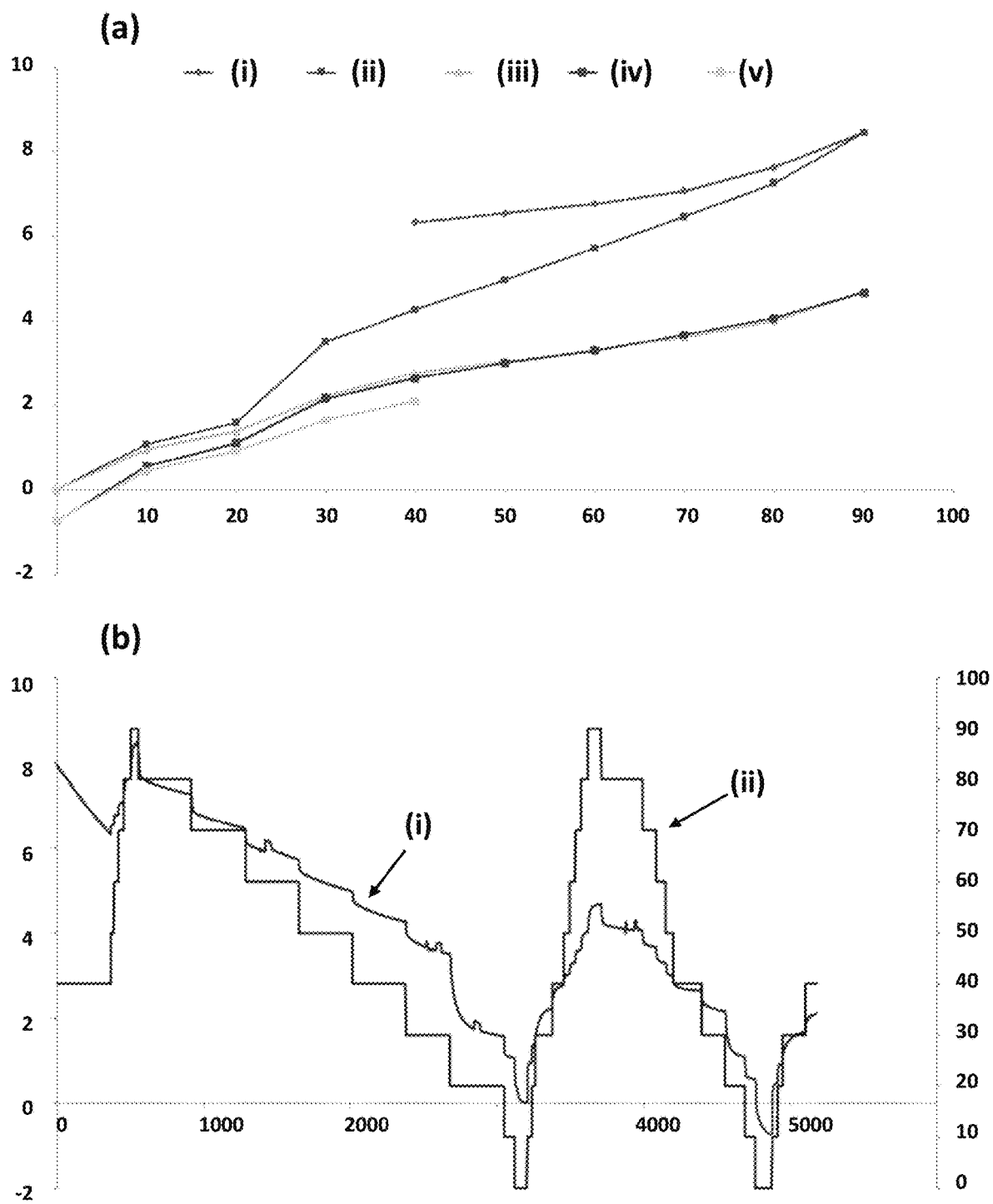
FIG. 13 shows GVS behavior for the acetate pattern 1 scaleup material.

FIG. 13 shows GVS behavior for the acetate pattern 1 scaleup material in (a) isotherm and (b) kinetic format. (a): horizontal axis=target RH (%); vertical axis=change in mass (%); (i) cycle 1 sorp; (ii) cycle 1 desorp; (iii) cycle 2 sorp; (iv) cycle 2 desorp; (v) cycle 3 sorp. (b) horizontal axis=time (min); left axis and (i)=change in mass (%); right axis and (ii)=target RH (%).

Figure 14:
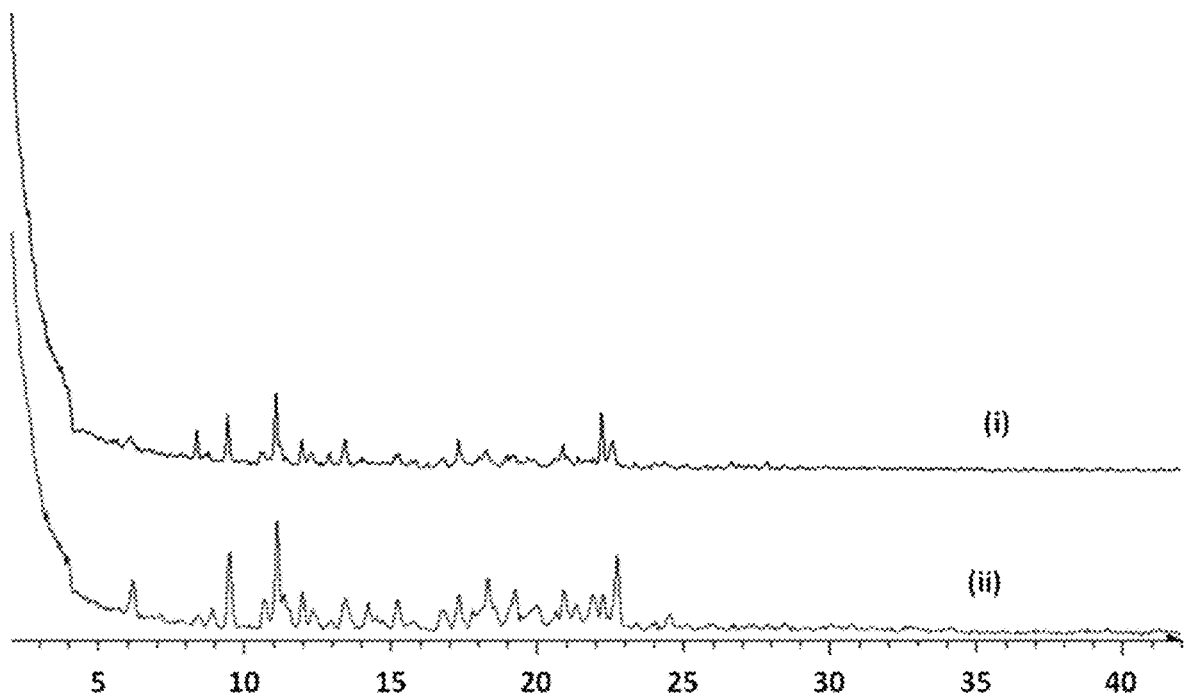
FIG. 14 shows (a) PXRD of Acetate Pattern 1 (a) pre- and (b) post-GVS.

FIG. 14 shows PXRD of Acetate Pattern 1 (i) pre- and (ii) post-GVS.

Chloride pattern 1 Scaleup Cethromycin (249.7 mg) was treated with 10 vol (2.5 ml) of EtOAc and warmed in a Polar Bear at 50° C. HCl (1M THF, 359 µl, 1 eq.) was added. After acid addition a yellow gum was observed. The sample was kept at 50° C. for 30 mins and then slowly cooled at 0.1° C. per min to 5° C. The resulting yellow gum was agitated with a spatula and left to stir overnight at 5° C. This gave a white suspension. The solid was isolated by filtration on a Büchner suction and washed with cold n-heptane. This yielded an off-white powder (168.6 mg). $^1$H NMR, PXRD and TGA for chloride pattern 1 scaleup (not shown) is substantially the same as that for the Example 4 chloride pattern 1 material.

NMR analysis of chloride pattern 1 shows peak shifts consistent with those for salt formation. Chloride pattern 1 was obtained as a microcrystalline agglomerated powder and is a hydrated mono salt. The material is hygroscopic with a mass uptake of 8.6% between 0 and 90% RH. Due to the hygroscopicity it is difficult to quantify the hydrate stoichiometry. The material isolated is 98.6% pure by HPLC and the solid form is stable under accelerated storage conditions.

Solubility of the salt forms was measured and compared to solubility data collected for amorphous cethromycin freebase. Kinetic solubility data collected in SGF media show an increase in solubility of ca. 10 mg/ml, increasing to over 35 mg/ml for phosphate and acetate pattern 1 compared to the amorphous freebase (25 mg/ml). The chloride pattern 1 solubility (27 mg/ml) in SGF is not significantly different to the amorphous freebase. There are no significant differences in thermodynamic solubility in PBS across all salt forms identified and the amorphous freebase. Thermodynamic solubility in DI water was improved for all the salt forms compared to the freebase. Some of this increase may be due to lowing of pH from the presence of the acidic counterions; however, for phosphoric acid at pH 7 there was a significant increase from 0.4 mg/ml for the freebase to over 35 mg/ml for phosphate pattern 1.

Chloride pattern 1 was selected for the polymorphism studies going forward as this salt had the most favourable solid state properties and some improvement in solubility particularly in DI water.

TABLE 12

Summary of salt scaleup.

| | | | |
|---|---|---|---|
| Solvent | EtOAc | EtOAc | EtOAc |
| Acid | PHOA | AcOH | HCl |
| Observations on solvent addition | Clear colorless solution | Clear colorless solution | Clear colorless solution |
| After acid addition | Thick yellow gum, particles coming off with stirring | Clear colorless solution | Yellow gum, clear colorless solution |
| After slow cooling to 5° C. | White paste some yellow gum | Clear colorless solution | Yellow gum, clear colorless solution |

TABLE 12-continued

Summary of salt scaleup.

| | | | |
|---|---|---|---|
| Treatment 1 | Filtered on a Buchner funnel and washed with cold heptane | Evaporated under ambient conditions | Agitated with a spatula, and left to stir over night at 5° C. |
| Outcome 1 | White powder, some yellow material left in first vial | Very pale yellow transparent gum | White suspension |
| Treatment 2 | N/A | Agitated with a spatula, treated with 10 vol heptane and matured for 2 days. | Filtered under Buchner suction, washed with cold heptane. |
| Outcome 2 | N/A | White powder in suspension filtered under Buchner suction. | Off-white powder |
| PXRD | phosphate pattern 1 (weakly crystalline) | acetate pattern 1 | chloride pattern 1 |

Further characterisation was performed on the three salts and is detailed in Table 13 below.

TABLE 13

Characterization of scaleup products.

| Counterion | phosphate | acetate | chloride |
|---|---|---|---|
| Solvent | EtOAc | EtOAc | EtOAc |
| HR PXRD | Very weakly crystalline phosphate pattern 1 | acetate pattern 1 | chloride pattern 1 |
| $^1$H NMR | Consistent with previous analysis of phosphate salt. Peaks from dimethylamine shifted from 2.2 to 2.3 ppm. 0.2 eq EtOAc | Consistent with previous analysis of acetate salt. ca. 1 eq of acetic acid. Trace EtOAc | Consistent with previous analysis of chloride salt. Peaks shifted indicating salt formation. Trace EtOAc |
| IC | 0.7 eq. phosphate | N/A | 1.01 eq. chloride |
| TGA | 1.1 % mass loss between ambient and 100° C. (ca. 0.5 eq. water); 0.9% mass loss between 30 and 190° C.; degradation onset ca. 200° C. | 1.7% mass loss from ambient to 65° C.; 4.7% mass loss between 65° C. and 130° C.; 0.9% mass loss between 130° C. and 190° C.; degradation onset ca. 225° C. Total mass loss of 7.2%, ca. 1.1 eq. acetic acid or 3.5 eq. water, likely a combination of both. | 5.3% mass loss between ambient and 100° C. (ca. 2.5 eq. water); degradation onset ca. 212° C. |
| DSC | Broad endotherm, onset from ambient (89 J/g); endotherm onset 183.6° C. (5 J/g) | Broad endotherm, onset from ambient (61 J/g); endotherm onset 112.2° C. (55 J/g); broad exotherm onset 134.3° C. (12 J/g); broad endotherm onset 168.1° C. (7 J/g); endotherm at 218° C. (44 J/g). | Broad endotherm, onset from ambient (124 J/g); endotherm, onset 177° C. (15 J/g); noisy event above 200° C. likely due to degradation. |
| Karl-Fischer | 6%, 3.1 eq. water | 4.7%, 2.3 eq. water | 6.9%, 3.3 eq. water |
| HPLC Purity | 98.50% | 98.50% | 98.60% |
| Storage 40° C./75% RH | PXRD: Remains poorly crystalline; HPLC: 98.3% | PXRD: Some peak shifts and some new peaks (Denoted acetate pattern 2); HPLC: 98.5% NMR: Peaks consistent with those previously observed, reduction in acetic acid, 0.66 eq. | PXRD: chloride pattern 1 (more crystalline); HPLC: 98.6% |
| Storage 25° C./97% RH | Sample deliquesced; no analysis run | PXRD: Unchanged; HPLC: 98.0% | PXRD: chloride pattern 1 (more crystalline); HPLC: 98.5% |
| GVS | 21.0 % uptake between 0 and 90% RH. Material is hygroscopic. | 8.6% uptake between 0 and 90% RH. Material is very hygroscopic Variation between cycle 1 and cycle 2 indicating change to material, likely loss of acetic acid. | 8.6% mass uptake between 0 and 90% RH (no hysteresis). Material is hygroscopic |

TABLE 13-continued

Characterization of scaleup products.

| PXRD Post GVS | amorphous | Some shifts and new peaks similar to acetate pattern 2 from storage at 40° C./75% RH; NMR: Consistent with previous analysis of acetate pattern 2, 0.63 eq. acetic acid. | Unchanged post GVS |
|---|---|---|---|
| Kinetic solubility (2 hours) in SGF media | >35 mg/ml (pH 2.1) | >35 mg/ml (pH 4.8) | 27 mg/ml (pH 3.3) |
| Thermodynamic solubility (24 hours) in PBS media | 1.4 mg/ml (pH 7.0) | 2.4 mg/ml (pH 6.8) | 1.2 mg/ml (pH 7.0) |
| Thermodynamic solubility (24 hours) in DI water | >35 mg/ml (pH 2.4) | >35 mg/ml (pH 7.0) | 25 mg/ml (pH 4.7) |
| PLM | Glassy shards | Agglomerates of microcrystals | Agglomerates of microcrystals |
| SEM | N/A | Agglomerates of irregularly shaped crystals ranging from 10 μm and 400 μm | Agglomerates of irregularly shaped crystals ranging from 10 μm-300 μm. |

Example 7: Polymorphs of Freebase Cethromycin

The acetate pattern 1 material was converted to freebase pattern 1 by the following procedure. Acetate pattern 1 (ca. 10 mg, Example 4) was transferred to a TGA pan. The material was then heated using a TGA instrument to 150° C. at 10° C. per min, held isothermally at 150° C. for 20 min and then cooled at 10° C. per min back to RT. The sample was removed from the TGA pan and analysed by PXRD. PXRD for freebase pattern 1 scaleup (not shown) is substantially the same as that for the Example 5 freebase pattern 1 material from VT PXRD. This and other batches of freebase pattern 1 were then used to characterise this form.

An alternative polymorph of cethromycin, termed freebase pattern 2, can be obtained. Cethromycin (100 mg) was suspended in 25 vol (2.5 ml) of deionised water, and in PBS. The resulting suspensions were slurried for 24 hrs at 25° C. The samples were filtered on Büchner funnels, then analysed by PXRD. $^1$H NMR for freebase pattern 2 (not shown) is substantially the same as that for freebase cethromycin.

Figure 15:
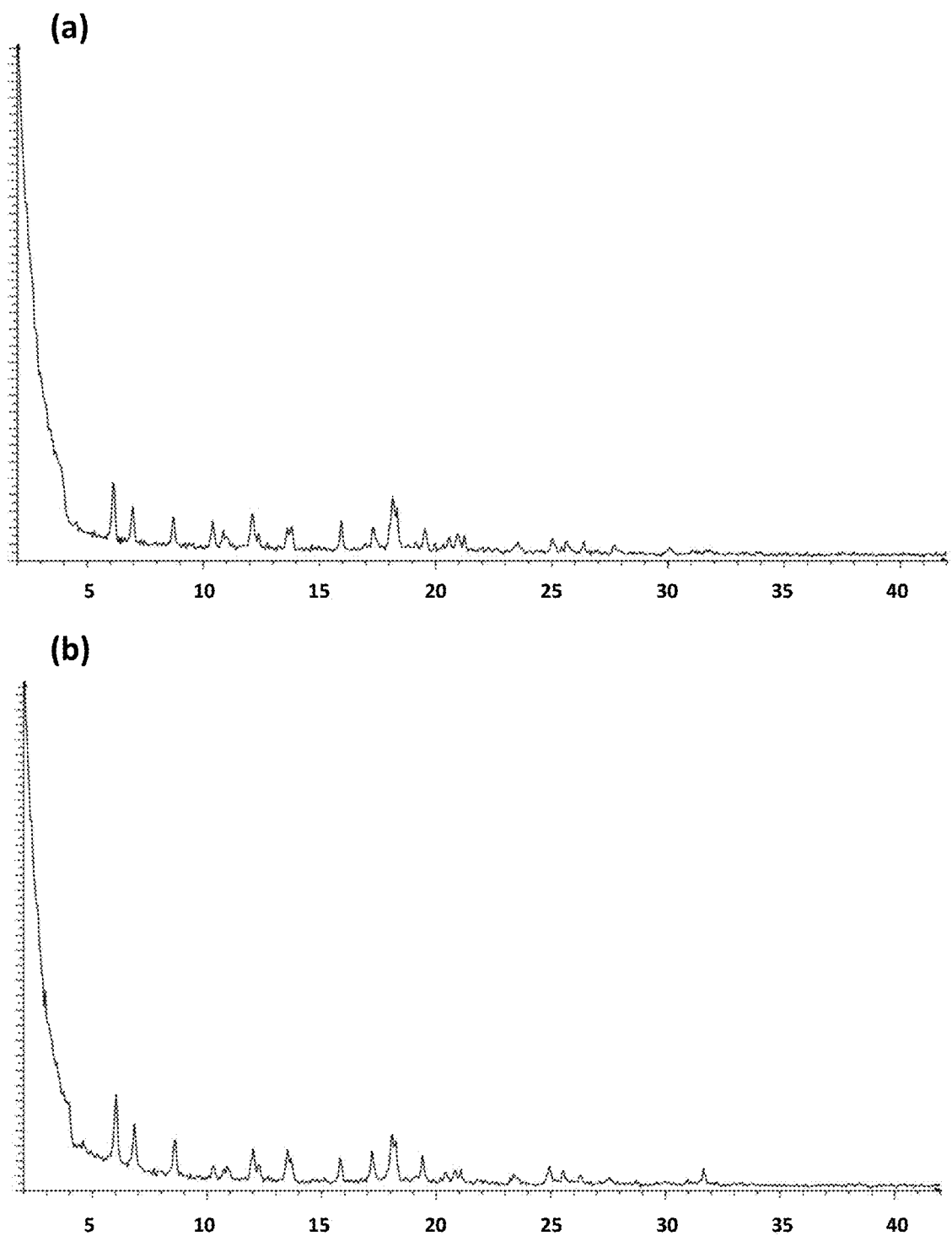
FIG. 15 shows PXRD characterization of freebase pattern 2 obtained from (a) H$_2$O and (b) PBS.

FIG. 15 shows PXRD characterization of freebase pattern 2 obtained from (a) $H_2O$ and (b) PBS.

TABLE 14

Characterization of scaleup products.

| Starting material | acetate pattern 1 | acetate pattern 1 | acetate pattern 1 | Cethromycin |
|---|---|---|---|---|
| Treatment | Heat to 150° C., followed by cooling to RT. Storage at 40° C./75% RH for 7 days. | Heat to 150° C., followed by cooling to RT | Heat to 150° C., followed by cooling to RT | Slurry in 25 vol water or PBS for 24 hrs. |
| PXRD | freebase pattern 1 | freebase pattern 1 | freebase pattern 1 | freebase pattern 2 |
| $^1$H NMR | N/A | Consistent with previously observed structure | N/A | Consistent with previously observed structure |
| TGA | No mass loss observed between ambient and 230° C. where degradation onset occurs. | N/A | Ongoing | 6.0% mass loss from ambient to 150° C. (2.7 eq. water); degradation onset 250° C. |
| DSC | Endotherm onset 227° C. (likely associated with the melt). | N/A | Ongoing | Broad endotherm onset at ambient (120 J/g); endotherm at 227° C. (5 J/g). |
| HPLC Purity | 96.6% | N/A | 95.8% | 98.6% |

Example 8: Scaleup Investigation of Chloride Pattern 1

Cethromycin (2498.8 mg) was treated with 10 vol (25 ml) of EtOAc and warmed in a Polar Bear at 40° C., forming a very pale brown solution. HCl (1M THF stock solution, 3590 µl, 1.1 eq.) was added. After acid addition a yellow gum was observed. The sample was kept at 40° C. for 5 min and then slowly cooled at 0.1° C. per min to 5° C. The sample was kept at 5° C. for 3 days. This gave a white suspension that was filtered on a Büchner funnel. This yielded a white powder (2177 mg). $^1$H NMR and PXRD for chloride pattern 1 scaleup (not shown) is substantially the same as that for the Example 4 chloride pattern 1 material.

Example 9: Investigation of Amorphous Cethromycin Chloride

Three portions of cethromycin chloride pattern 1 (Example 8, 25 mg) were dissolved in ACN:H$_2$O (1:1 v/v), THF:H$_2$O (7:3 v/v) and t-butanol:H$_2$O (1:1 v/v), (0.5 ml) respectively. Attempts to dissolve the same material in t-butanol (30 vol, 0.75 ml) were unsuccessful. The solutions obtained were then filtered to remove any remaining solid particles. The solutions were then frozen in a dry ice-acetone bath, and the solvents were removed by lyophilization. The residual solids were analyzed by PXRD and NMR. HPLC purity was also performed on the sample obtained from ACN:H$_2$O (1:1).

Preparation of amorphous cethromycin chloride was attempted in four different solvents (Table 24). Preparation was successful in ACN:H$_2$O (1:1 v/v), THF:H$_2$O (7:3 v/v) and t-butanol:H$_2$O (1:1 v/v). The sample prepared from ACN:H$_2$O (1:1 v/v) contained no residual solvent by NMR; thus, this solvent system was selected for further preparation of amorphous material. HPLC analysis of the compound from this solvent system showed that its purity was >98.9%.

TABLE 15

Summary of amorphous cethromycin chloride preparation.

| Solvent | ACN:H$_2$O (1:1) | THF:H$_2$O (7:3) | t-butanol | t-butanol:H$_2$O (1:1) |
| --- | --- | --- | --- | --- |
| Observation on solvent addition | Solution | Solution | Suspension | Solution |
| Observations after freeze drying | Low density white solid | Low density white solid | N/A | Low density white solid |
| PXRD | amorphous | amorphous | N/A | amorphous |
| NMR | Consistent with HCl salt; no residual ACN | Consistent with HCl salt; trace residual THF (<0.1 eq) | N/A | Consistent with HCl salt; trace residual t-butanol (<0.1 eq) |
| HPLC | 0.989 | N/A | N/A | N/A |

Example 10: Scaleup of Amorphous Cethromycin Chloride

Cethromycin chloride pattern 1 (1 g,) was dissolved in 20 ml (20 vol) ACN:H$_2$O (1:1 v/v) and was filtered through a nylon filter to remove any residual seed particles. The resulting solution was pipetted into 40 HPLC vials in 500 µl portions (ca. 25 mg of HCl salt per vial). Samples were frozen in an acetone/dry ice bath and then placed in a freeze dryer at −80° C., 1 mbar pressure for 16 hours. Samples formed white low-density solids.

PXRD analysis was performed on 4 of the vials and further characterisation was also performed on some of the samples. The first batch (Batch "A") was amorphous, consistent with cethromycin chloride by $^1$H NMR with trace residual solvent. A significant mass loss was observed in the TGA most likely attributable to water. A glass transition was observed in the DSC at ca. 161° C. There was ca. 0.9 eq. of HCl in the sample and it was noted that there had been a significant decrease in purity (98.7 to 89.0%). This reduction in purity was due to a low retention peak, ca. 10% auc, RRT=0.18, which is around the point of the solvent front. This analysis could not be repeated due to insufficient material.

Two further batches (Batches "B" and "C") were analysed by PXRD and $^1$H NMR and were consistent with cethromycin chloride. A final batch (Batch "D") was analysed by PXRD, $^1$H NMR, IC, HPLC and post storage at 40° C./75% RH for 9 days. PXRD showed that the material was amorphous. $^1$H NMR for amorphous cethromycin chloride (not shown) is substantially the same as that for the Example 4 chloride pattern 1 material. IC analysis showed that the material contained 1 eq chloride by IC. The material did not crystallise during storage at elevated temperature and humidity. No reduction in purity was observed in this batch.

Of the 40 samples prepared, 18 were subsequently used in the solubility assessment of amorphous cethromycin chloride.

TABLE 16

Characterization of amorphous cethromycin chloride scaleup products.

| Batch | A | B | C | D |
| --- | --- | --- | --- | --- |
| Counterion | chloride | chloride | chloride | chloride |
| HR PXRD | amorphous | amorphous | amorphous | amorphous |
| $^1$H NMR | Structure as expected for cethromycin chloride; trace ACN. | Structure as expected for cethromycin chloride; trace ACN. | Structure as expected for cethromycin chloride; trace ACN | N/A |
| IC | 0.90 eq. chloride | N/A | N/A | 1.05 eq. chloride |
| TGA | 6.4% mass loss from ambient to 100° C. (3 eq. water). Degradation onset 212° C. | N/A | N/A | N/A |
| DSC | Broad endotherm, onset from ambient (123 J/g), Noisy event from around 160° C. likely due to glass transition. mDSC shows Tg around 161.3° C. | N/A | N/A | N/A |
| HPLC Purity | 89.0% | N/A | N/A | 98.7% |
| Storage at 40° C./75% RH for 9 days | N/A | N/A | N/A | amorphous |

Example 11: Solubility Assessment of Amorphous Cethromycin Chloride

Amorphous cethromycin (18 individual vials of the Example 10 material, ca. 25 mg per vial) was treated with selected individual solvents at 25° C. The study was carried out with up to 5 vols of the respective solvents. The amorphous cethromycin chloride was found to be soluble in 10 of the 18 solvents investigated (Table 17). Slurries were obtained in heptane, EtOAc, isopropyl acetate (iPrOAc), methyl isobutyl ketone (MIBK), methyl ethyl ketone (MEK), methyl t-butyl ether (MTBE), cyclohexane (cHex), and toluene.

TABLE 17

Solubility of amorphous cethromycin chloride salts at 25° C. in various solvents.

| Solvent | Dilution by solvent | | | | | |
|---|---|---|---|---|---|---|
| | 1 vol | 2 vol | 3 vol | 4 vol | 5 vol | 10 vol |
| Hept | x | x | x | x | x | ✓o |
| EtOAc | x | x | x | x | ✓o | |
| iPrOAc | x | x | x | x | x | ✓o |
| MIBK | x | x | x | x | ✓o | |
| iPrOH | ✓ | | | | | |
| MEK | x | x | x | x | ✓o | |
| Acetone | ✓ | | | | | |
| Ethanol | ✓ | | | | | |
| MTBE | x | x | x | x | | ✓o |
| iBuOH | ✓ | | | | | |
| cHex | x | x | x | x | x | ✓o |
| MeOH | ✓ | | | | | |
| Toluene | x | x | x | x | x | ✓o |
| THF | x | x | x | x | ✓ | |
| MeCN | ✓ | | | | | |
| EtOH/H$_2$O (10%) | ✓ | | | | | |
| iPrOH/H$_2$O (10%) | ✓ | | | | | |
| THF/H$_2$O (10%) | ✓ | | | | | |

✓ dissolved
✓o slurry
x not dissolved/too dry to slurry

Procedure 1: Cooling and Maturation of Chloride Pattern 1

Formation of polymorphs from chloride pattern 1 was examined using the procedure described below. In a first step, solubility of the material in selected individual solvents at 50° C. was investigated. Solvent amounts of up to 60 vol were used. Results of this extended study are presented in Table 18.

TABLE 18

Extended assessment of cethromycin chloride solubility.

| Solvent | Dilution by solvent | | | | | | |
|---|---|---|---|---|---|---|---|
| | 5 vol | 10 vol | 20 vol | 30 vol | 40 vol | 50 vol | 60 vol |
| Hept | x | x | x | x | x | x | x |
| EtOAc | x | x | x | x | x | x | x |
| iPrOAc | x | x | x | x | x | x | x |
| MIBK | x | x | x | x | x | x | x |
| iPrOH | o | ✓ | | | | | |
| MEK | x | x | x | x | x | o | o |
| Acetone | x | o* | o* | o* | o* | o* | o* |
| Ethanol | ✓ | | | | | | |
| MTBE | x | x | x | x | x | x | x |
| iBuOH | ✓ | | | | | | |
| cHex | x | x | x | x | x | x | x |
| MeOH | ✓ | | | | | | |
| Toluene | x | x | x | x | x | x | x |
| THF | x | x | x | x | x | o | o |
| MeCN | o* | o* | o* | o* | o* | o* | o* |
| EtOH/H$_2$O (10%) | ✓ | | | | | | |
| IPA/H$_2$O (10%) | ✓ | | | | | | |
| THF/H$_2$O (10%) | ✓ | | | | | | |

✓ dissolved
o turbid
o* mostly dissolved; slightly turbid
x not dissolved/too dry to slurry Example 12. Polymorph Experiments on Cethromycin Chloride Polymorph experiments for cethromycin chloride were carried out using a variety of techniques to maximise the chances of discovering new forms.

The procedure for examination of polymorph formation was chosen for each sample based on the outcome of the solubility experiment for that sample. The following samples, which were fully dissolved at 50° C., were allowed to cool. Samples that remained in solution after 1 week were allowed to evaporate under ambient conditions.

TABLE 19

Polymorph formation from solutions of chloride pattern 1.

| Expt | Solvent | Outcome on Cooling | Post-Cooling Treatment | Outcome | PXRD |
|---|---|---|---|---|---|
| (v) | iPrOH | solution | evaporation | white solid | chloride pattern 1 |
| (vii) | Acetone | solution | evaporation | white solid | chloride pattern 1 |
| (viii) | Ethanol | solution | evaporation | glassy solid | chloride pattern 1 |
| (x) | iBuOH | solution | evaporation | glassy solid | chloride pattern 1 |
| (xii) | MeOH | solution | evaporation | glassy solid | chloride pattern 1 |
| (xv) | MeCN | solution | evaporation | white solid | chloride pattern 1 |
| (xvi) | EtOH/H$_2$O (10%) | solution | evaporation | glassy solid | amorphous |
| (xvii) | IPA/H$_2$O (10%) | precipitate | none | solid | chloride pattern 1 |
| (xviii) | THF/H$_2$O (10%) | solution | evaporation | glassy solid | amorphous |

The following samples, which did not fully dissolve at 50° C., were matured in a shaker incubator cycling from 25° C. to 50° C. every 4 hours for 1 week. Saturated solutions were cooled to 5° C. at 0.1° C. per minute and then kept in the fridge at 5° C. for 1 week.

TABLE 20

Polymorph formation from incompletely dissolved chloride pattern 1.

| Expt | Solvent | Outcome | PXRD |
|---|---|---|---|
| (i) | Hept | Solid | chloride pattern 1 |
| (ii) | EtOAc | Solid | amorphous |
| (iii) | iPrOAc | Solid | chloride pattern 1 |
| (iv) | MIBK | Solid | chloride pattern 1 |
| (vi) | MEK | Solid | N/A |
| (ix) | MTBE | Solid | chloride pattern 1 |
| (xi) | cHex | Solid | chloride pattern 1 |
| (xiii) | Toluene | Solid | chloride pattern 1 |
| (xiv) | THF | Solid | N/A |

Figure 16:
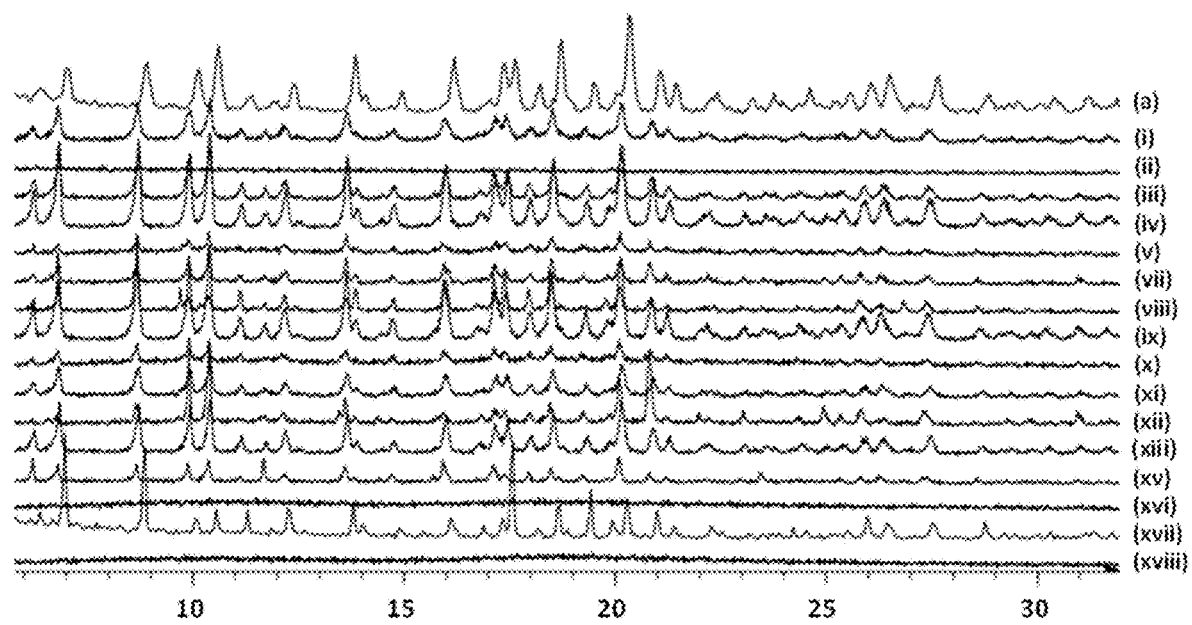
FIG. 16 shows PXRD characterization of polymorph experiments for cethromycin chloride using Procedure 1.

FIG. 16 shows PXRD characterization of polymorph experiments for cethromycin chloride using Procedure 1. Trace (a) is chloride pattern 1 from Example 8; labels for the remainder of the traces correspond to the experiment number in Table 19. PXRD diffractograms were not obtained for Experiments (vi) and (xiv).

Procedure 2: Maturing Amorphous Cethromycin Chloride (5-25° C.)

The procedure for examination of polymorph formation was chosen for each sample based on the outcome of the solubility experiment for that sample as described in Example 11. The following samples, which formed suspensions at 25° C. in Example 11, were matured in a Polar Bear cycling from 5° C. to 25° C. every 4 hours for 4 days. Samples were observed after 1 day of treatment. Following maturation, samples that formed pastes were dried on a spatula tip.

TABLE 21

Outcome of Polymorph Procedure 2.

| Expt | Solvent | Observation (1 day) | Treatment 1 | Outcome | Drying | PXRD |
|---|---|---|---|---|---|---|
| (i) | Hept | white paste | (a) | white paste | (c) | amorphous |
| (ii) | EtOAc | pale yellow-grey gum | (a) | pale yellow-grey gum | N/A | N/A |
| (iii) | iPrOAc | white paste | (a) | white paste | (c) | amorphous |
| (iv) | MIBK | pale yellow-grey gum | (a) | pale grey gum | N/A | N/A |
| (vi) | MEK | white paste | (a) | white paste | (c) | chloride pattern 1 |
| (ix) | MTBE | off-white paste | (a) | white paste | (c) | amorphous |
| (xi) | cHex | white suspension | (b) | white paste | (c) | amorphous |
| (xiii) | Toluene | white gel | (b) | off-white paste | (c) | chloride pattern 1 |

(a) 4 days further maturation.
(b) 3 days further maturation.
(c) Dried on a spatula tip.

The following samples, which formed solutions at 25° C. in Example 11, were matured in a Polar Bear for 1 day. Samples that formed solid precipitates after this period were dried. Samples remaining in solution were seeded with additional amorphous cethromycin chloride (an extra 25-50 mg), and matured under the same conditions for a further 3-4 days.

| Expt | Solvent | Outcome after Treatment 1 | Treatment 2 | Outcome after Treatment 2 | Treatment 3 | PXRD |
|---|---|---|---|---|---|---|
| (v) | iPrOH | solution | (a) | gummy solution | N/A | N/A |
| (vii) | Acetone | off-white paste | (d) | N/A | N/A | chloride pattern 1 |
| (viii) | Ethanol | solution | (b) | pale yellow-grey gum | (e) | chloride pattern 1 |
| (x) | iBuOH | solution | (a) | off-white paste | (e) | chloride pattern 1 |
| (xii) | MeOH | white suspension | (e) | white suspension | N/A | chloride pattern 2 |
| (xiv) | THF | solution | (c) | white paste | (e) | chloride pattern 1 |
| (xv) | MeCN | white suspension | (e) | N/A | N/A | chloride pattern 1 |

-continued

| Expt | Solvent | Outcome after Treatment 1 | Treatment 2 | Outcome after Treatment 2 | Treatment 3 | PXRD |
|---|---|---|---|---|---|---|
| (xvi) | EtOH/H$_2$O (10%) | white suspension | (e) | N/A | N/A | chloride pattern 1 |
| (xvii) | IPA/H$_2$O (10%) | white paste | (e) | N/A | N/A | chloride pattern 1 |
| (xviii) | THF/H$_2$O (10%) | white paste | (e) | N/A | N/A | chloride pattern 1 |

(a) Added 25 mg amorphous cethromycin chloride; 3 days further maturation.
(b) Added 25 mg amorphous cethromycin chloride; 4 days further maturation.
(c) Added 50 mg amorphous cethromycin chloride; 3 days further maturation.
(d) Dried on a microscope slide.
(e) Dried on a spatula tip.
(f) Evaporation under ambient conditions.

Experiment (xii) performed in MeOH, provided a new polymorph, labelled chloride pattern 2. Full characterization of this material is below, in Example 13.

Figure 17:
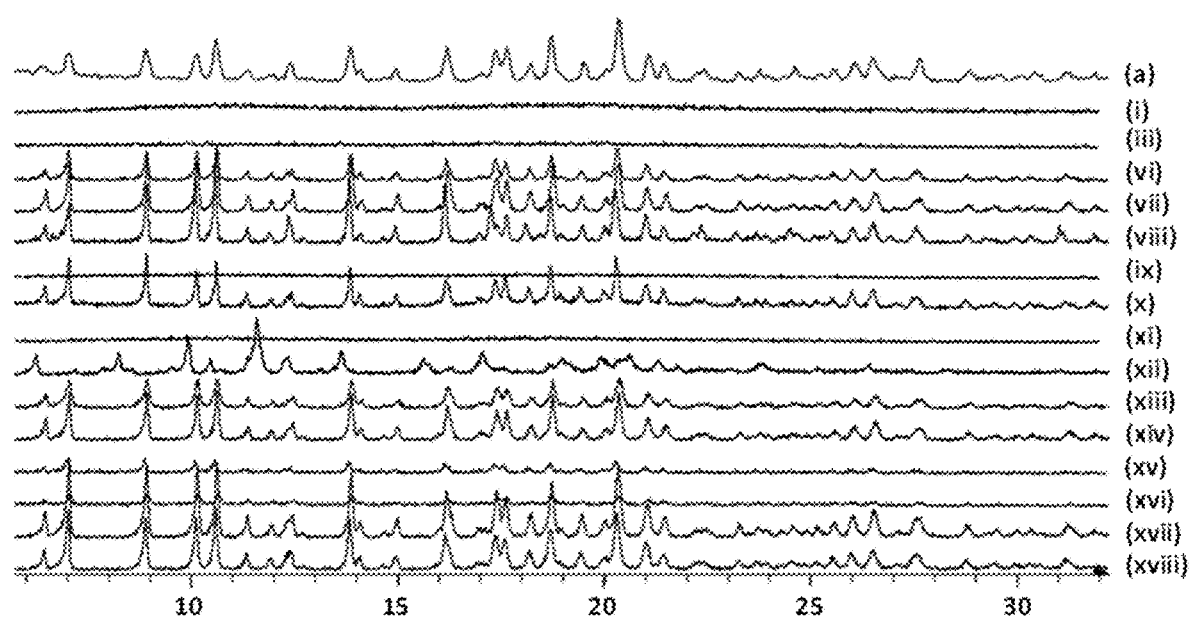
FIG. 17 shows PXRD characterization of polymorph experiments for cethromycin chloride using Procedure 2.

FIG. 17 shows PXRD characterization of polymorph experiments for cethromycin chloride using Procedure 2. Trace (a) is the Example 8 material; labels for the remainder of the traces correspond to the experiment number in Table 21. PXRD diffractograms were not obtained for Experiments (ii), (iv), and (v).

Procedure 3: Maturing Amorphous Cethromycin Chloride (25-50° C.)

Amorphous cethromycin chloride (25 mg) was treated with 10 volumes of solvent (250 µl). Samples were matured in a shaker-incubator cycling from 25° C. to 50° C. every 4 hours. The samples that formed pastes were isolated by drying on a spatula tip.

TABLE 22

Outcome of Polymorph Procedure 3.

| Expt | Solvent | After solvent add'n | After maturation | Drying | PXRD |
|---|---|---|---|---|---|
| (i) | Hept | white paste | white paste | (a) | amorphous |
| (ii) | EtOAc | translucent white gel | white paste | (a) | Poorly crystalline chloride pattern 1 |
| (iii) | iPrOAc | white paste | white paste | (a) | chloride pattern 1 |
| (iv) | MIBK | translucent white gel | translucent white gel | (a) | chloride pattern 1 |
| (vi) | MEK | complete dissolution | white paste | (a) | chloride pattern 1 |

TABLE 22-continued

Outcome of Polymorph Procedure 3.

| Expt | Solvent | After solvent add'n | After maturation | Drying | PXRD |
|---|---|---|---|---|---|
| (vi) | MTBE | white paste | white paste | (a) | chloride pattern 1 |
| (vii) | cHex | white paste | white paste | (a) | amorphous |
| (viii) | Toluene | translucent white gel | grey-yellow gum | N/A | N/A |

(a) Dried on a spatula tip.

Figure 18:
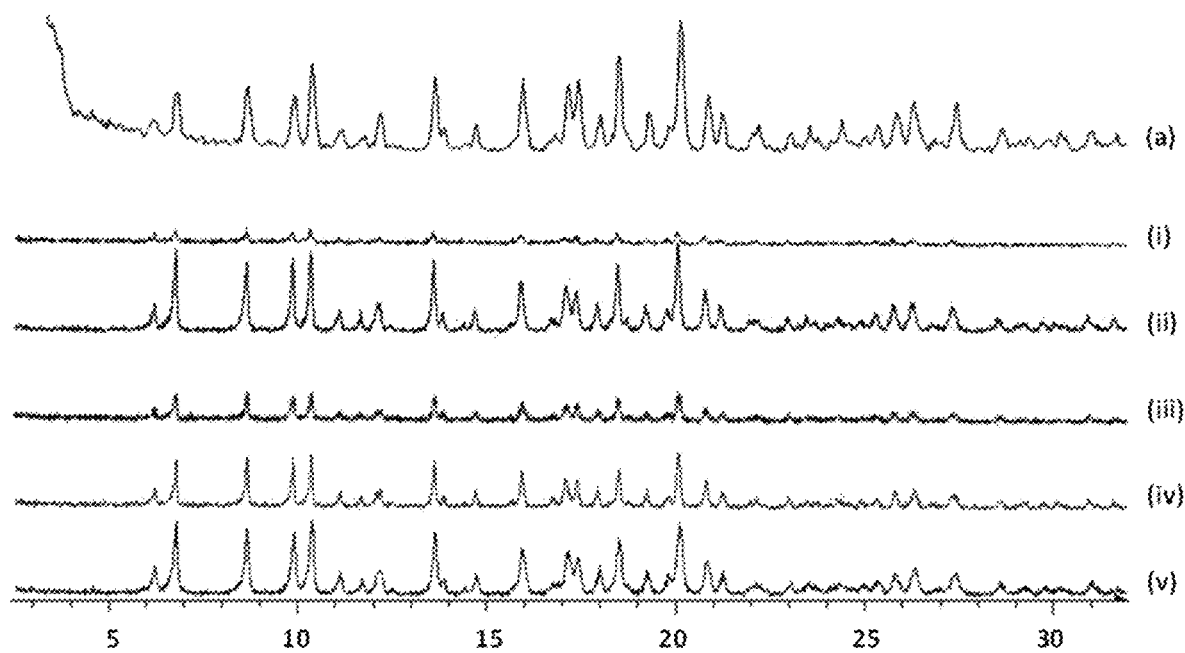
FIG. 18 shows PXRD characterization of polymorph experiments for cethromycin chloride using Procedure 3.

FIG. 18 shows PXRD characterization of polymorph experiments for cethromycin chloride using Procedure 3. Trace (a) is the Example 8 material; labels for the remainder of the traces correspond to the experiment number in Table 22. PXRD diffractograms were not obtained for Experiment (vii). The diffractograms for Experiments (i) and (viii), corresponding to amorphous material, are not shown.

Procedure 4: Antisolvent Addition

Cethromycin chloride pattern 1 (25 mg, Example 8) was treated with minimum solvent until a solution was formed at 50° C. or a maximum of 100 volumes had been reached. The samples were initially treated with an equal volume of antisolvent (n-heptane) and this was increased up to a 1:3 ratio (solvent: antisolvent). Samples with large initial volumes of solvent (100 vol) were treated with 1 equal volume of heptane (1:1 ratio). All samples were cooled at 0.1° C./min to 5° C. Any resulting solids were isolated and analysed by PXRD. Any persisting solutions were evaporated under ambient conditions and analysed by PXRD.

Figure 19:
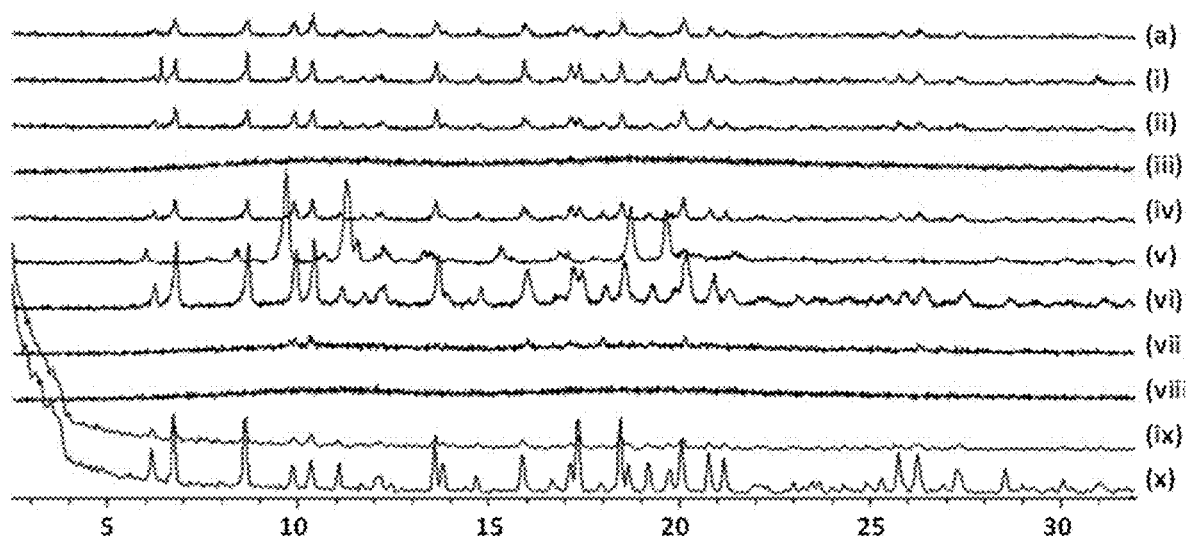
FIG. 19 shows PXRD characterization of polymorph experiments for cethromycin chloride using Procedure 4.

FIG. 19 shows PXRD characterization of polymorph experiments for cethromycin chloride using Procedure 4. Trace (a) is the Example 8 material; labels for the remainder of the traces correspond to the experiment number in Table 22. PXRD diffractograms were not obtained for Experiment (vii). The diffractograms for Experiments (i) and (viii), corresponding to amorphous material, are not shown.

TABLE 23

Outcome of Polymorph Procedure 4.

| Expt | Solvent; Vols added | Outcome | After add'n of 1/2/3 equal volumes | Treatment 1/ outcome | Treatment 2/ outcome | PXRD |
|---|---|---|---|---|---|---|
| (i) | iPrOH; 100 vol | (b) | (e)/N/A/N/A | (II)/(e) | (III)/(i) | chloride pattern 1 |
| (ii) | Acetone; 100 vol | (d) | (g)/N/A/N/A | (II)/(e) | (III)/(i) | chloride pattern 1 |
| (iii) | EtOH; 10 vol | (a) | (e)/(f)/N/A | (II)/(g) | (III)/(k) | amorphous |

TABLE 23-continued

Outcome of Polymorph Procedure 4.

| Expt | Solvent; Vols added | Outcome | After add'n of 1/2/3 equal volumes | Treatment 1/ outcome | Treatment 2/ outcome | PXRD |
|---|---|---|---|---|---|---|
| (iv) | iBuOH; 5 vol | (a) | (h)/N/A/N/A | (II)/(c) | (III)/(i) | chloride pattern 1 |
| (v) | MeOH; 5 vol | (a) | (e)/(e)/(e) | (II)/(e) | (III)/(i) | chloride pattern 2 |
| (vi) | THF; 100 vol | (d) | (h)/N/A/N/A | (II)/(j) | (III)/(i) | chloride pattern 1 |
| (vii) | MeCN; 100 vol | (c) | (l)/N/A/N/A | (II)/(e) | (III)/(k) | chloride pattern 1 |
| (viii) | EtOH/H$_2$O (10%); 5 vol | (a) | (e)/(e)/(e) | (II)/(e) | (III)/(k) | amorphous |
| (ix) | IPA/H$_2$O (10%); 5 vol | (a) | (e)/(e)/(e) | (II)/(i) | N/A | chloride pattern 1 |
| (x) | THF/H$_2$O (10%); 5 vol | (a) | (e)/(f)/N/A | (II)/(i) | N/A | chloride pattern 1 |

(a) dissolution
(b) turbid, then dissolution
(c) slightly turbid
(d) turbid
(e) no precipitate
(f) slightly cloudy
(g) thin white precipitate
(h) white precipitate
(i) white solid
(j) gummy white solid
(k) glassy solid
(l) antisolvent immiscible
(I) maturation in a Polar Bear
(II) cooled at 0.1° C. per min to 5° C.
(III) evaporated Example 13. Characterization of Chloride Pattern 2

Cethromycin chloride pattern 2 (Example 12, Procedure 2, experiment xii: MeOH) was characterized using a range of techniques. It is most likely a hydrated mono salt and was found to lose crystallinity on isolation. The TGA indicates a mass loss of 5.1%, attributed to water. This corresponds to 2.4 eq water but as the material is hygroscopic it is difficult to define the exact stoichiometry. A broad endotherm is observed in the DSC corresponding to this loss, followed by a second endotherm at 186.5° C. which is likely a melt. HPLC confirmed that the purity was consistent with the starting material.

TABLE 24

Characterization of chloride pattern 2.

| Counterion | chloride |
|---|---|
| PXRD | chloride pattern 2 but loss of crystallinity on isolation |
| $^1$H NMR | Consistent with previous analysis of chloride salt. No residual MeOH |
| IC | 0.97 eq. Cl |
| TGA | 5.1% mass loss between ambient and 100° C. (ca. 2.4 eq. water) degradation onset ca. 211° C. |
| DSC | Broad endotherm, onset from ambient (150 J/g), Endotherm, onset 186.5° C. (26 J/g). Noisy event above 200° C. likely due to degradation |
| HPLC Purity | 98.8% |

Figure 20:
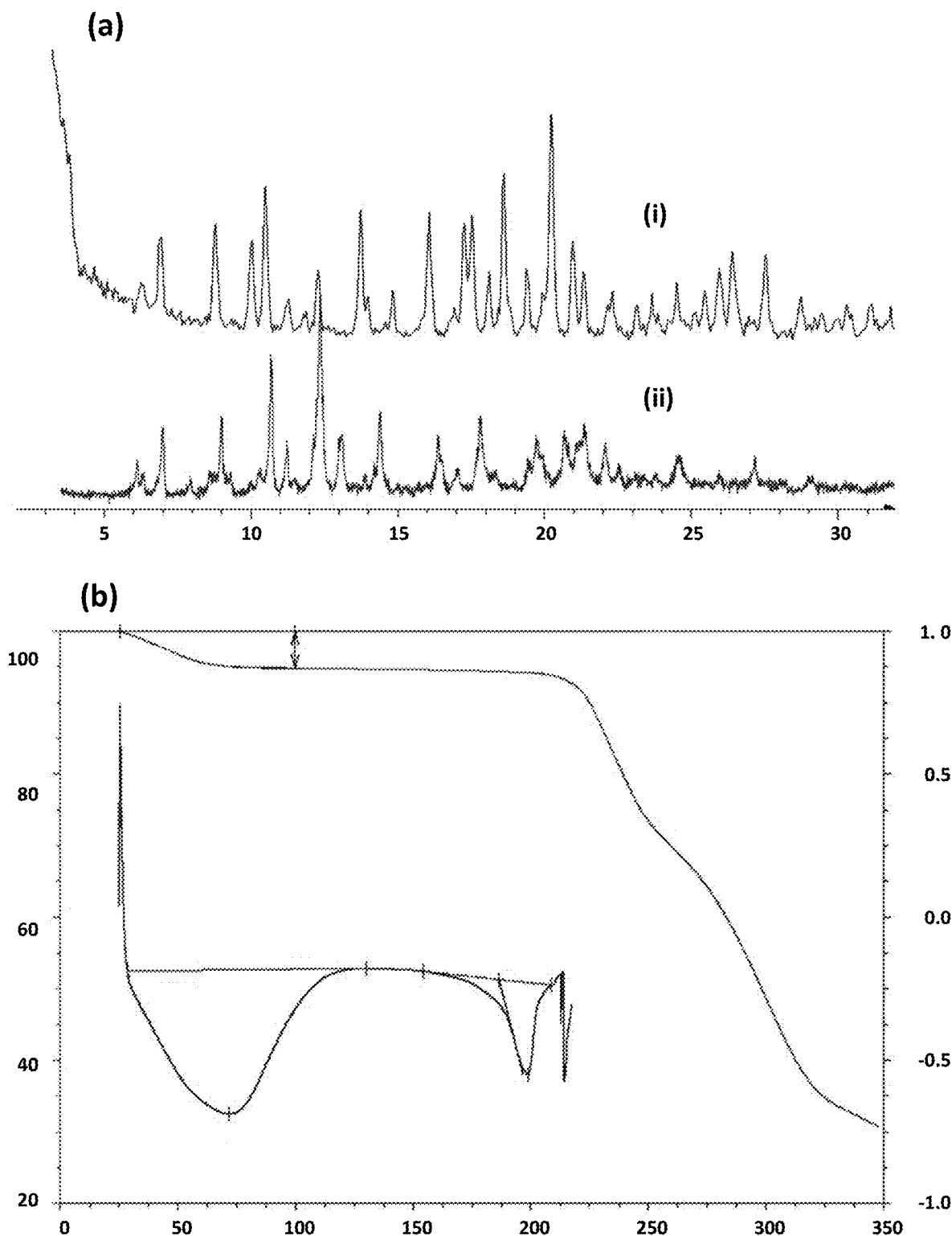
FIG. 20 shows (a) PXRD and (b)$^1$H NMR for chloride pattern 2.

FIG. 20 shows (a) PXRD for (i) chloride pattern 2 (Example 8) and (ii) chloride pattern 2. Peak information, from a related diffractogram, for the 18 most intense peaks is provided in Table 25. Also shown is (b) thermal analysis for chloride pattern 2. Further details are provided in Table 24.

TABLE 25

Peaks in the PXRD diffractogram for cethromycin chloride pattern 2.

| 2θ, ° | d-spacing, Å | Intensity |
|---|---|---|
| 5.3 | 16.5 | 94 |
| 6.1 | 14.5 | 77 |
| 7.7 | 11.5 | 57 |
| 8.4 | 10.5 | 68 |
| 9.8 | 9.1 | 82 |
| 10.7 | 8.3 | 75 |
| 11.4 | 7.8 | 100 |
| 11.6 | 7.6 | 62 |
| 12.3 | 7.2 | 51 |
| 13.4 | 6.6 | 58 |
| 15.4 | 5.7 | 56 |
| 17.0 | 5.2 | 72 |
| 17.8 | 5.0 | 38 |
| 18.8 | 4.7 | 66 |
| 19.3 | 4.6 | 40 |
| 19.7 | 4.5 | 58 |
| 20.6 | 4.3 | 54 |
| 21.4 | 4.1 | 73 |

Figure 21:
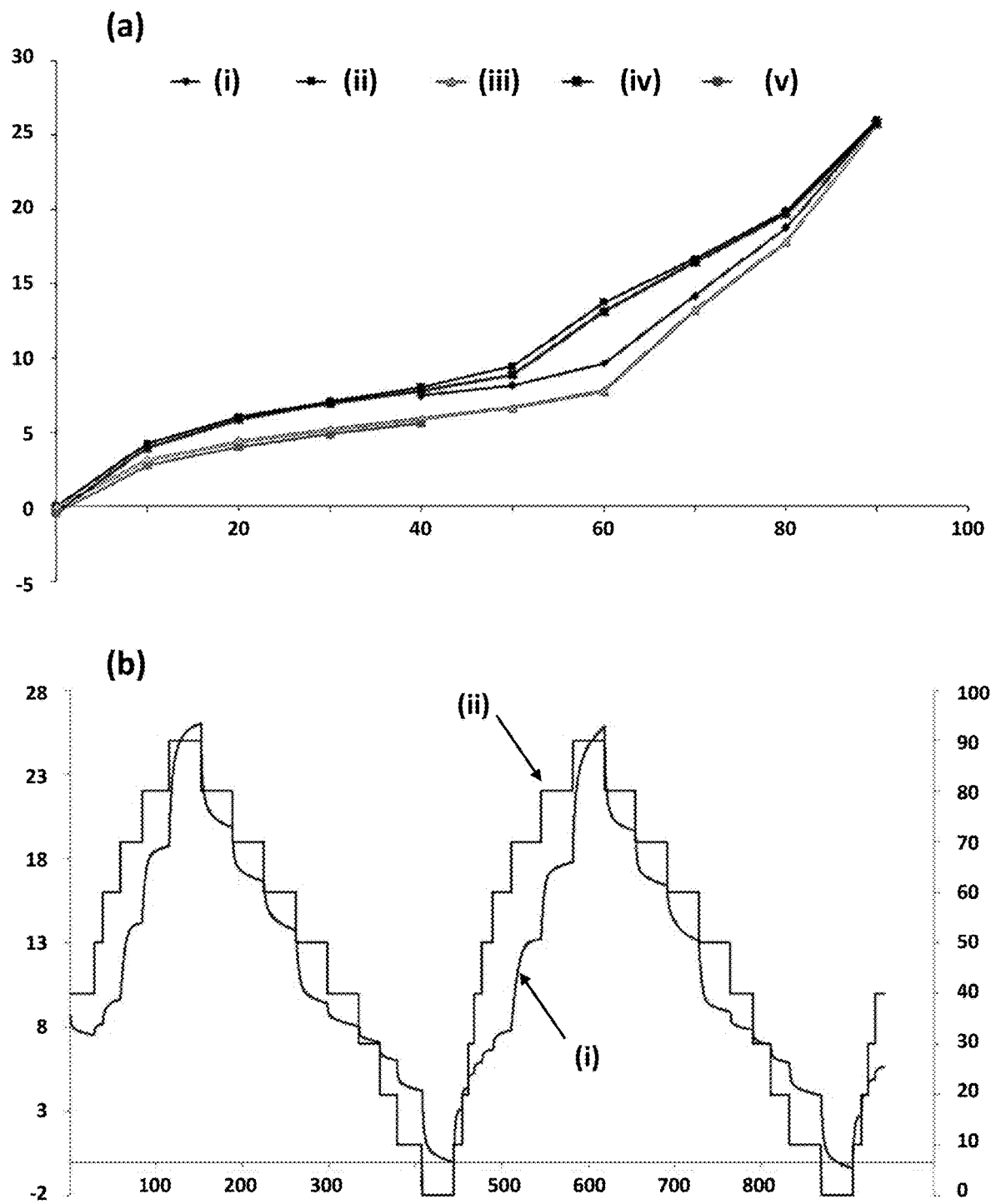
FIG. 21 shows GVS behavior for chloride pattern 2.

FIG. 21 shows GVS behavior for chloride pattern 2.

Polymorph formation experiments have been carried out using both amorphous (prepared by freeze drying) and crystalline cethromycin chloride input material using cooling, temperature cycling, anti-solvent addition and evaporation techniques. The majority of samples were either amorphous or chloride pattern 1. On two occasions from methanol an alternative crystalline solid was isolated, denoted chloride pattern 2. Initial characterisation of chloride pattern 2 shows that the material is crystalline with a significant mass loss by TGA attributed to water, no residual solvent by 1H NMR. The material is 98.8% pure and IC confirms chloride content of 0.97 eq. There was a reduction in crystallinity in the bulk sample after isolation compared to the initial analysis performed on a small aliquot.

Example 14. Preparation of Chloride Pattern 2

Cethromycin chloride pattern 1 (350 mg, Example 8) was dissolved in 5 volumes of MeCN:water (1:1) (v/v) (1.75 ml). The solution was passed through a nylon filter into a 25 ml round bottom flask. The sample was then frozen in an acetone/dry ice bath and then freeze-dried at −80° C., 1 mbar pressure, affording amorphous cethromycin chloride. The material was amorphous by PXRD, and 98.7% pure by HPLC. $^1$H NMR for amorphous cethromycin chloride (not shown) is substantially the same as that for the Example 4 chloride pattern 1 material.

The amorphous cethromycin chloride from the previous step was treated with 1 vol (290 µl) of methanol at 25° C., resulting in a light brown solution with small particles of solid remaining. The sample was then matured in a Polar Bear cycling from 25° C. to 5° C. every 4 h for 1 day, this resulted in the formation of a white suspension. The sample was cooled from 25° C. to 5° C. (maximum cooling rate) and kept at this temperature for 30 minutes in order to maximise precipitation. Filtration was attempted, however the suspension proved too viscous to filter. Therefore, the sample was dried under ambient conditions evaporatively for 2 days.

yielded an off-white powder, confirmed chloride pattern 1 by PXRD, yield=2316.3 mg (88.4%). $^1$H NMR for chloride pattern 1 scaleup (not shown) is substantially the same as that for the Example 4 chloride pattern 1 material.

Preparation of amorphous cethromycin chloride Cethromycin chloride pattern 1 (600 mg,) was dissolved in MeCN:H$_2$O (1:1, v/v) (3 ml, 5 vol). A further 1 ml of the aqueous MeCN solvent was added (as small particles remained undissolved). The solution was then filtered through a nylon filter into a 50 ml flask to remove any remaining seed particles. The solution was then frozen in an acetone/dry ice bath and then freeze-dried at −80° C., 1 mbar pressure for 24 hrs. This resulted in a low density white solid, confirmed amorphous by PXRD. $^1$H NMR for amorphous cethromycin chloride (not shown) is substantially the same as that for the Example 4 chloride pattern 1 material.

Preparation of chloride pattern 2 Amorphous cethromycin chloride (520 mg) was treated with MeOH (520 µl, 1 vol). The resulting light brown solution was matured in a Polar Bear switching from 25° C. to 5° C. every 4 hours for 1 day. The resulting white suspension was cooled to 5° C. (from 25° C.) and kept at this temperature for 30 mins. The sample was then dried evaporatively under ambient conditions. This resulted in an off-white solid and was confirmed by PXRD as chloride pattern 2, yield=499.9 mg. PXRD and $^1$H NMR for amorphous cethromycin chloride (not shown) is substantially the same as that for the chloride pattern 2 from the Example 14 experiment.

TABLE 26

Characterization of chloride pattern 2.

| Counterion | chloride |
|---|---|
| HR PXRD | chloride pattern 2 |
| $^1$H NMR | Consistent with previous analysis of chloride salt. No residual MeOH |
| IC | 0.99 eq. Cl |
| PLM/SEM | Aggregates of irregularly shaped crystals between 20 and 350 µm in size. |
| TGA | 5.4% Mass loss (2.5 eq. water) from ambient to 100° C. Degradation onset 210° C. |
| DSC | Broad endotherm, onset from ambient (100 J/g), Endotherm, onset 189.6° C. (25 J/g). |
| KF | 8% water, (3.9 eq. water) |
| HPLC Purity | 98.9% |
| GVS | 25.8% mass uptake between 0% and 90% RH. Majority of uptake is between 50 and 90% RH with hysteresis between 50 and 80% RH. Material is very hygroscopic. PXRD: Material remains similar to chloride pattern 2 however it appears to have enhanced crystallinity. It does not match any crystalline freebase patterns. |
| Storage 25° C./97% RH, 9 days | PXRD: Converted to chloride pattern 1 HPLC: 98.7% |
| Storage 40° C./75% RH, 9 days | PXRD: Remained chloride pattern 2 HPLC: 97.9% |

Example 15. Competitive Slurry Experiments

Preparation of chloride pattern 1 Amorphous cethromycin (2500 mg) was treated with 10 volumes (25 ml) of EtOAc resulting in a light brown turbid solution. This was warmed to 40° C. and treated with 1.1 eq. of HCl (3590 µl of a 1 M THF stock solution). This resulted in the formation of a pale-yellow gum. The sample was cooled at 0.1° C./min to 5° C. and kept at this temperature with stirring for 2 days. The sample was seeded with chloride pattern 1 and was stirred at 5° C. for a further 3 days. After this period a white suspension was observed, and the sample was filtered on a Büchner funnel, then dried under suction for 20 mins. This

TABLE 27

Characterization of materials for competitive slurry experiments.

| Solvent | PXRD | NMR | HPLC |
|---|---|---|---|
| EtOAc | chloride pattern 1 | Consistent with HCl salt. <0.1 eq EtOAc, Trace THF | 98.4% |
| MeCN:H$_2$O (1:1, v/v) | amorphous | Consistent with HCl salt. No residual solvent. | 98.6% |
| MeOH | chloride pattern 1 | Consistent with HCl salt. Trace MeOH. | 98.5% |

Cethromycin chloride pattern 1 was used to prepare saturated solutions at 40° C. as shown in Table 28. All samples except for EtOAc were stirred for 12 hr at 40° C. The EtOAc suspension was stirred at this temperature for 1 hr (to reduce risk of evaporation). The saturated solutions were then filtered.

Figure 22:
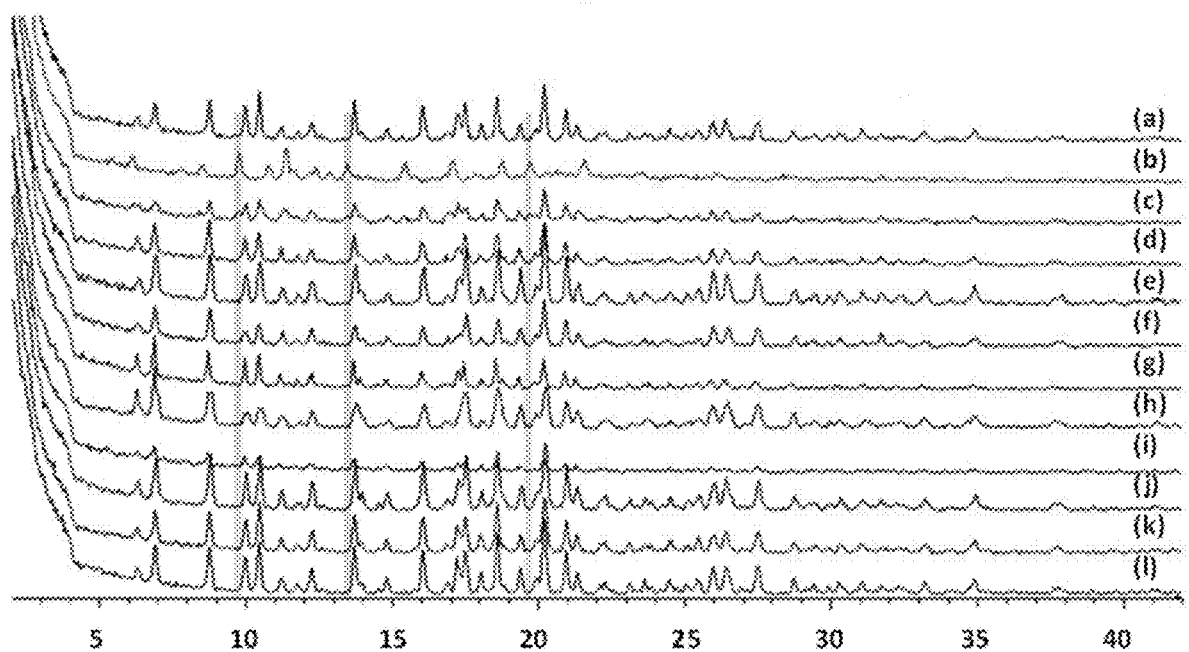
FIG. 22 shows PXRD analysis of the slurry experiments.

FIG. 22 shows PXRD analysis of the slurry experiments. Cethromycin chloride (a) pattern 1, (b) pattern 2, (c) mix of pattern 1+pattern 2; slurries with: THF at (d) 5° C., (e) 25° C., (f) 40° C.; H₂O at (g) 5° C., (h) 25° C., (i) 40° C.; EtOAc at (d) 5° C., (e) 25° C., (f) 40° C.

TABLE 29

Amounts of solvents for competitive slurry experiments.

| Solvent | Temp, ° C. | Initial observation | Observation after 3 days stirring | Observation on isolation | Isolation method | PXRD after 3 days |
|---|---|---|---|---|---|---|
| MeOH | 5 | (a) | (a) | N/A | N/A | N/A |
|  | 25 | (a) | (a) | N/A | N/A | N/A |
|  | 40 | (a) | (a) | N/A | N/A | N/A |
| THF | 5 | (b) | (b) | (b) | (I) | chloride pattern 1 |
|  | 25 | (b) | (b) | (b) | (I) | chloride pattern 1 |
|  | 40 | (b) | (b) | (b) | (I) | chloride pattern 1 |
| H₂O | 5 | (b) | (b) | (c) | (II) | chloride pattern 1 |
|  | 25 | (b) | (b) | (c) | (III) | chloride pattern 1 |
|  | 40 | (b) | (b) | (c) | (IV) | chloride pattern 1 |
| EtOAc | 5 | (b) | (b) | (b) | (I) | chloride pattern 1 |
|  | 25 | (b) | (b) | (d) | (IV) | chloride pattern 1 |
|  | 40 | (b) | (d) | (d) | (IV) | chloride pattern 1 |

(a) pale brown solution
(b) white suspension
(c) very thin suspension
(d) white paste
(I) dried on filter paper
(II) centrifugation, remained very wet, some
(III) centrifugation yielded a tacky solid
(IV) Spread on filter paper and dried evaporation

TABLE 28

Amounts of solvents for competitive slurry experiments.

| Solvent | Mass chloride pattern 1 | Volume solvent | Saturated solution |
|---|---|---|---|
| MeOH | 950 mg | 2 ml | All dissolved |
| THF | 80 mg | 2 ml | Saturated |
| H₂O | 135 mg | 2 ml | Saturated |
| EtOAc | 60 mg | 3 ml | Saturated |

Figure 24:
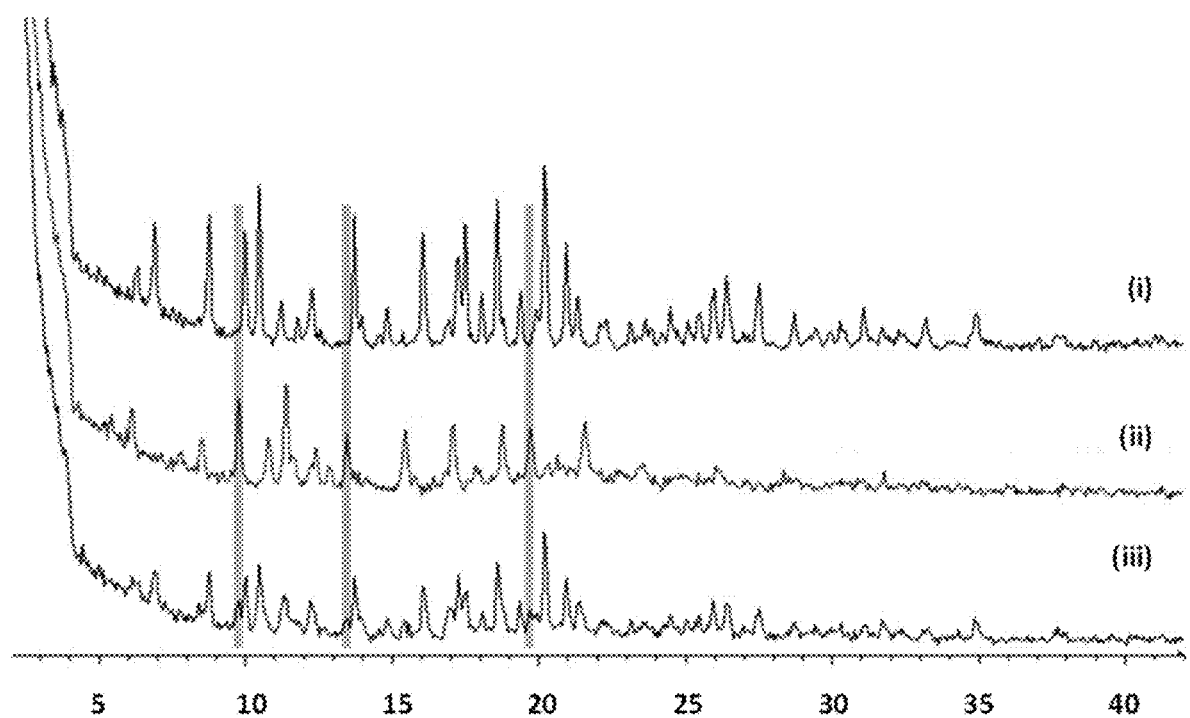
FIG. 24 shows PXRD for individual samples of cethromycin chloride patterns 1 and 2, and a mixture.

Approx. 350 mg portions of chloride pattern 1 and chloride pattern 2 were gently crushed (separately) in a pestle and mortar to yield particles of uniform size. A 1:1 mixture of ground chloride pattern 1 and ground chloride pattern 2 was prepared by mixing 300 mg of each material on a roller mixer for 24 hours. FIG. 24 shows PXRD for (i) cethromycin chloride pattern 1 (from Example 15), (b) cethromycin chloride pattern 2 (from Example 15), and (III) the mixture.

Portions of the above material were weighed out into twelve HPLC vials and were numbered as shown in Table 29. Each vial was treated with 0.3 ml of saturated solution, with the exception of samples performed in MeOH which was treated with 0.35 ml of the MeOH saturated solution. Before addition of saturated solution, each saturated solution was brought to the corresponding temperature and equilibrated for 30 mins. The resulting suspensions were allowed to settle and the saturated solution sampled from above. Note: it was not possible to saturate the MeOH solution due to the high solubility of the HCl salt in methanol (and limited material). The solid completely dissolved when treated with the partially saturated MeOH solution. Therefore, it was not possible to perform competitive slurries in MeOH. All other samples were slurried at 5° C., 25° C. and 40° C. for three days and then analysed by PXRD.

Example 16. Kinetic Solubility Studies on Cethromycin Chloride

Sufficient sample was suspended in 0.25 ml media for a maximum anticipated concentration of ca. 40 mg/ml of the free form of the compound. The resulting suspensions were then shaken at 25° C./750 rpm for 2 hours. After equilibration, the appearance was noted, and the pH of the saturated solution was measured. Samples were then filtered through a glass 'C' fibre filter (particle retention 1.2 μm). All the samples were diluted 100 times with SGF media. Quantitation was by HPLC with reference to a standard solution of approximately 0.15 mg/ml. Different volumes of the standard and diluted sample solutions were injected. The solubility was calculated using the peak areas determined by integration of the peak found at the same retention time as the principal peak in the standard injection.

TABLE 30

Kinetic solubility.

| Form | Media | Appearance at 24 hrs | pH at 2 hrs | Sol'y (mg/ml) | Avg Sol'y (mg/ml) |
|---|---|---|---|---|---|
| Cethromycin chloride pattern 2 | SGF | Thin suspension with some residual solid | 3.7 | 32.0 | 32.0 |
|  |  | Thin suspension with some residual solid | 3.7 | 32.0 |  |
| Cethromycin chloride pattern 1 |  | White, opaque suspension with some residual solid. | 3.4 | 26.0 | 26.0 |
|  |  | White, opaque suspension with some residual solid. | 3.4 | 26.0 |  |
| Cethromycin chloride pattern 1 |  | Suspension | 3.3 | 27.0 | 27.0 |
|  |  | Suspension | 3.3 | 26.0 |  |

Example 17. Thermodynamic Solubility Studies on Cethromycin Chloride

Sufficient sample was suspended in 0.25 ml media for a maximum anticipated concentration of ca. 40 mg/ml of the free form of the compound. The resulting suspensions were then shaken at 25° C./750 rpm for 24 hours. The pH of samples suspended in PBS pH 7.4 were checked and adjusted if necessary (>0.05 change in pH) after 2 hours. After equilibration, the appearance was noted and the pH of the saturated solution was measured. Samples were then filtered through a glass 'C' fibre filter (Particle retention 1.2 μm). Samples suspended in PBS pH 7.4 buffer was diluted 10 times with PBS buffer and samples suspended in DI water diluted 100 times with DI water.

TABLE 31

Thermodynamic solubility.

| Form | Media | Appearance at 24 hrs | pH at 24 hrs | Sol'y (mg/ml) | Avg Sol'y (mg/ml) |
|---|---|---|---|---|---|
| Cethromycin chloride pattern 2 | PBS | White, opaque suspension with some residual solid. | 7.1 | 1.00 | 1.2 |
| | | White, opaque suspension with some residual solid. | 7.0 | 1.40 | |
| | | White, opaque suspension with some residual solid. | 7.2 | 0.84 | 0.8 |
| Cethromycin chloride pattern 1 | | White, opaque suspension with some residual solid. | 7.2 | 0.74 | |
| Cethromycin chloride pattern 2 | DI Water | Slightly hazy suspension with some residual solid as floating particulates. | 5.3 | 31.00 | 31.0 |
| | | Slightly hazy suspension with some residual solid as floating particulates. | 5.3 | 31.00 | |
| Cethromycin chloride pattern 1 | | White, opaque suspension with some residual solid. | 5.0 | 26.00 | 27.0 |
| | | White, opaque suspension with some residual solid. | 5.0 | 27.00 | |
| Cethromycin chloride pattern 1 | PBS | Suspension, solid on side of vial | 7.0 | 1.1 | 1.2 |
| | | Suspension, solid on side of vial | 7.0 | 1.4 | |
| | DI Water | Suspension | 4.7 | 25.0 | 25.0 |
| | | Suspension | 4.8 | 25.0 | |

The solubility results from analyses performed on chloride pattern 1 are generally consistent across both batches analysed. Cethromycin pattern 2 shows increased solubility compared to pattern 1 although this is only a difference of ca. 6 mg/ml in DI water and SGF and 0.4 mg/ml in PBS.

The solubility of cethromycin chloride is of comparable solubility to the amorphous freebase in both PBS and SGF media however results show that in DI water the cethromycin chloride (both pattern 1 and pattern 2) is significantly more soluble than amorphous freebase. This may be due to the slight change in pH, equilibrating to between pH 4.5 and 5.2 for the chloride salts but remaining at pH 7.0 for the freebase, which follows the general trend is that cethromycin is more soluble under more acidic conditions.

PXRD analysis was performed on residues that remained undissolved after the solubility analysis to check for changes in solid form. In PBS both chloride pattern 1 and pattern 2 converted to the freebase pattern 2, previously observed by slurrying freebase pattern 1 in PBS or water for 24 hours. As clear solutions were also obtained for chloride pattern 2 in SGF and deionised water no solubility values can be reported for this form. Chloride pattern 1 remained unchanged in SGF and deionised water.

Example 18. Solubility Studies on Cethromycin Chloride

TABLE 32

Solubility of cethromycin freebase and salts at 2 hr.

| Form | Media | Appearance at 2 hrs | pH at 2 hrs | Sol'y (mg/ml) | Avg Sol'y (mg/ml) | PXRD of Residues |
|---|---|---|---|---|---|---|
| Free form | SGF media | Suspension, solid on side of vial | 7.5 | 24 | 25 | amorphous |

TABLE 32-continued

Solubility of cethromycin freebase and salts at 2 hr.

| Form | Media | Appearance at 2 hrs | pH at 2 hrs | Sol'y (mg/ml) | Avg Sol'y (mg/ml) | PXRD of Residues |
|---|---|---|---|---|---|---|
| Free form | | Suspension, solid on side of vial | 7.6 | | 25 | amorphous |
| PHOA | | Clear solution | 2.1 | >35 | >35 | N/A sample in solution |
| HCl | | Suspension | 3.3 | 27 | 27 | N/A |
| HCl | | Suspension | 3.3 | 26 | | N/A |
| AcOH | | Clear solution | 4.8 | >35 | >35 | N/A sample in solution |
| AcOH | | Clear solution | 4.7 | >35 | | N/A sample in solution |

TABLE 33

Solubility of cethromycin freebase and salts at 24 hr.

| Form | Media | Appearance at 24 hrs | pH at 24 hrs | Sol'y (mg/ml) | Avg Sol'y (mg/ml) | PXRD of Residues |
|---|---|---|---|---|---|---|
| Free form | PBS pH 7.4 | Suspension, thick solid layer at side walls | 6.8 | 2.0 | 2.0 | freebase pattern 2 |
| Free form | | Suspension, thick solid layer at side walls | 6.8 | 1.9 | | freebase pattern 2 |
| PHOA | | Suspension, solid on side of vial | 7.0 | 1.4 | 1.4 | freebase pattern 2 |
| HCl | | Suspension, solid on side of vial | 7.0 | 1.1 | 1.2 | chloride pattern 1 with reduced crystallinity |
| HCl | | Suspension, solid on side of vial | 7.0 | 1.4 | | N/A |
| AcOH | | Suspension, solid on side of vial | 6.8 | 2.5 | 2.4 | N/A |
| AcOH | | Suspension, solid on side of vial | 6.7 | 2.3 | | N/A |

TABLE 34

Solubility of cethromycin freebase and salts at 24 hr.

| Form | Media | Appearance at 24 hrs | pH at 24 hrs | Sol'y (mg/ml) | Avg Sol'y (mg/ml) | PXRD of Residues |
|---|---|---|---|---|---|---|
| Free form | DI Water | Suspension, solid on side of centrifuge tube | 8.1 | 0.35 | 0.41 | freebase pattern 2 |
| Free form | | Suspension, solid on side of centrifuge tube | 8.1 | 0.47 | | freebase pattern 2 |
| PHOA | | Clear solution | 2.4 | >35 | >35 | N/A sample in solution |
| HCl | | Suspension | 4.7 | 25 | 25 | N/A |
| HCl | | Suspension | 4.8 | 25 | | N/A |
| AcOH | | Clear solution | 7.0 | >35 | >35 | N/A sample in solution |
| AcOH | | Clear solution | 7.0 | >35 | | N/A sample in solution |

Figure 25:
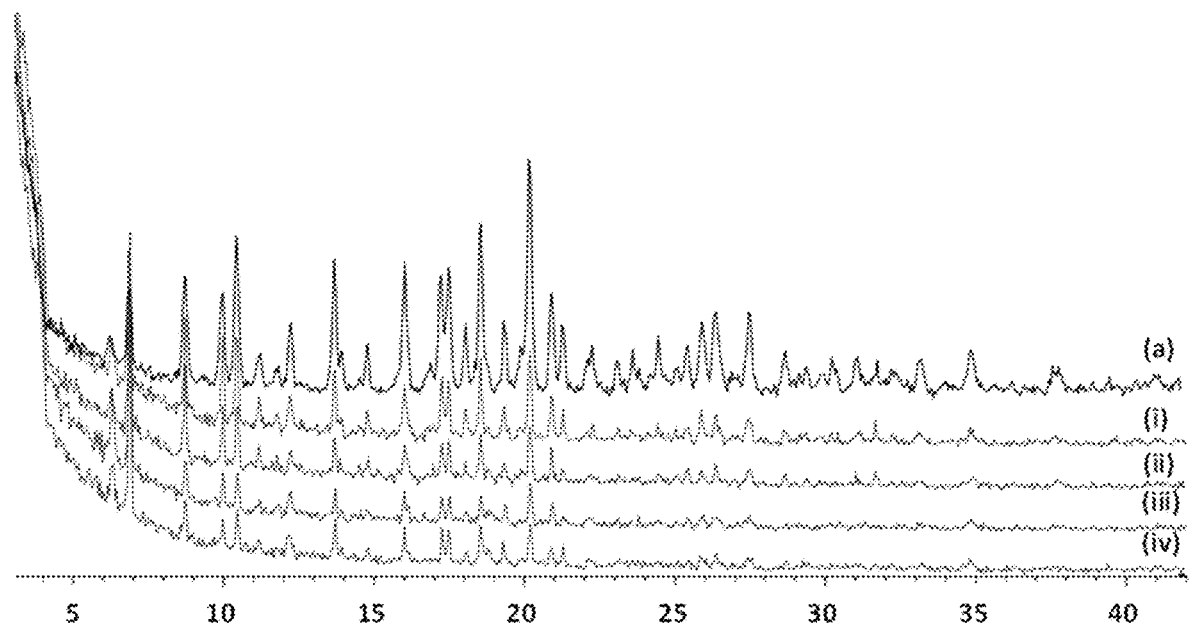
FIG. 25 shows an overlay of the solids obtained post solubility.

The following samples from the solubility experiments provided material characterized as cethromycin chloride pattern 1. FIG. 25 shows the diffractograms for the four samples, with the diffractogram for (a) cethromycin chloride pattern 1 from Example 8 included for comparison.

TABLE 35

Cethromycin chloride pattern 1 material from solubility experiments.

| Input material | Media | Observations post solubility | PXRD |
|---|---|---|---|
| Chloride Pattern 1 | SGF | Thin white suspension | (i) |
| | SGF | Thin white residue | (ii) |
| | DI H$_2$O | Thin white residue | (iii) |
| | DI H$_2$O | White residue | (iv) |

Figure 26:
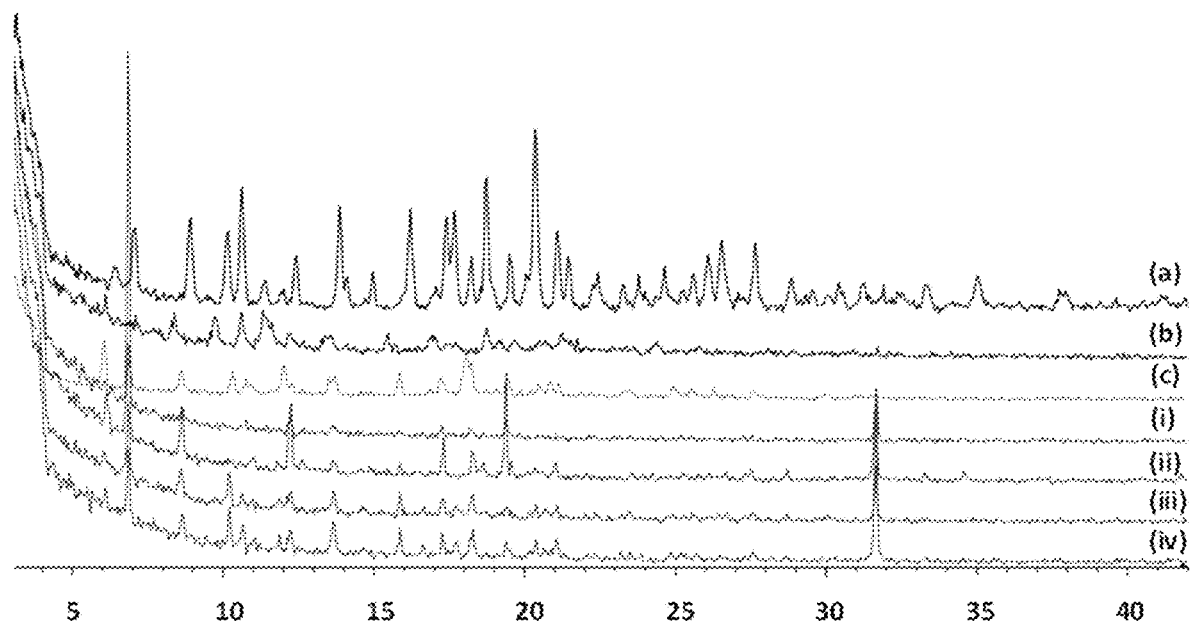
FIG. 26 shows an overlay of the solids obtained post solubility.

The following samples from the solubility experiments provided material characterized as cethromycin freebase pattern 2. FIG. 26 shows the diffractograms for the four samples, with the diffractograms for (a) cethromycin chloride pattern 1 from Example 8, (b) cethromycin chloride pattern 2 from Example 14, and (c) cethromycin freebase pattern 2 from Example 7 included for comparison.

TABLE 36

Cethromycin chloride pattern 2 material from solubility experiments.

| Input material | Media | Observations post solubility | PXRD |
|---|---|---|---|
| Chloride Pattern 1 | PBS | Thin white suspension | (i) |
| Chloride Pattern 2 | PBS | Thin white suspension | (ii) |
| | PBS | Small amount of thin white suspension | (iii) |
| | PBS | Small amount of thin white suspension | (iv) |

Example 19. Stability Studies on Cethromycin Chloride

Studies were performed on various cethromycin forms in order to determine stability for storage.

Figure 23:
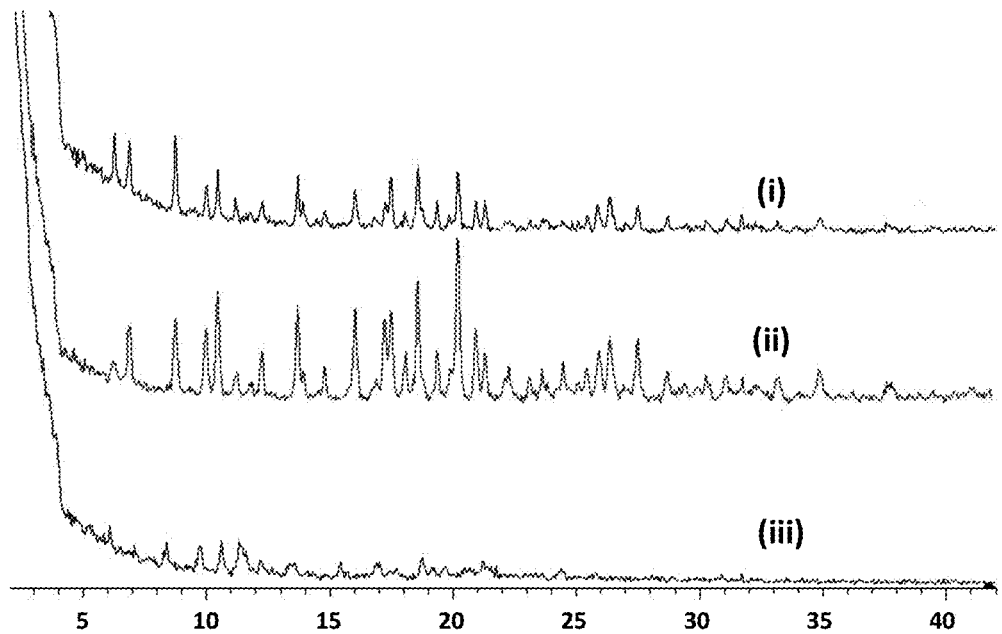
FIG. 23 shows PXRD studies on storage of cethromycin chloride Pattern 2.
Figure 23:
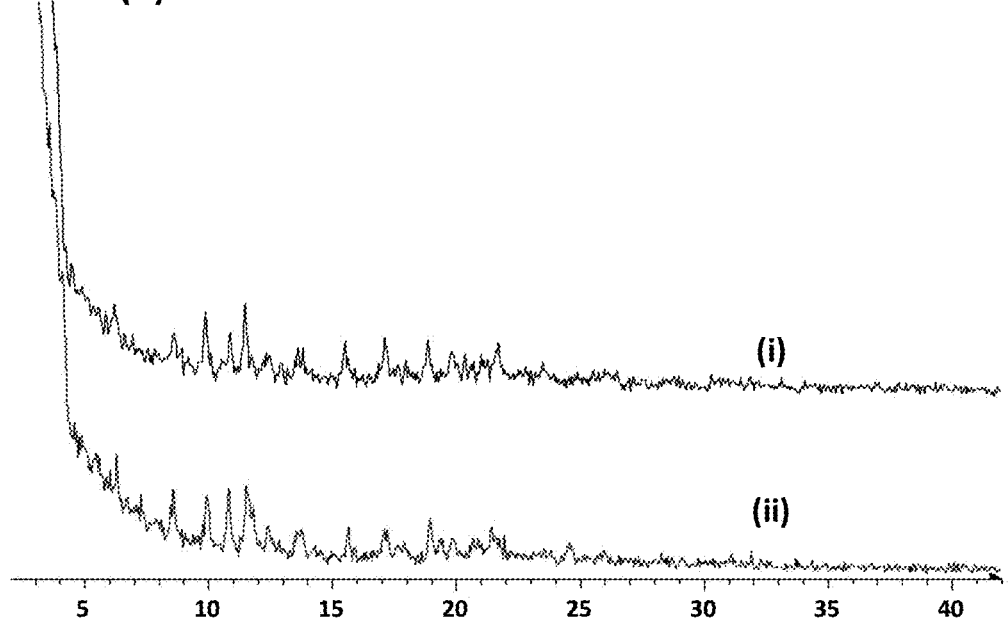

FIG. 23 shows PXRD studies on storage of Chloride Pattern 2. (a) PXRD of (i) chloride pattern 2 post storage (25° C., 97% RH, 9 days), (ii) chloride pattern 1 from Example 8, and (iii) chloride pattern 2 from Example 14. (b) PXRD of (i) chloride pattern 2 post storage (40° C., 75% RH, 9 days), and (ii) chloride pattern 2 from Example 14.

Example 20. Comparison of In Vivo Activity of Cethromycin Chloride and Base

Figure 27:
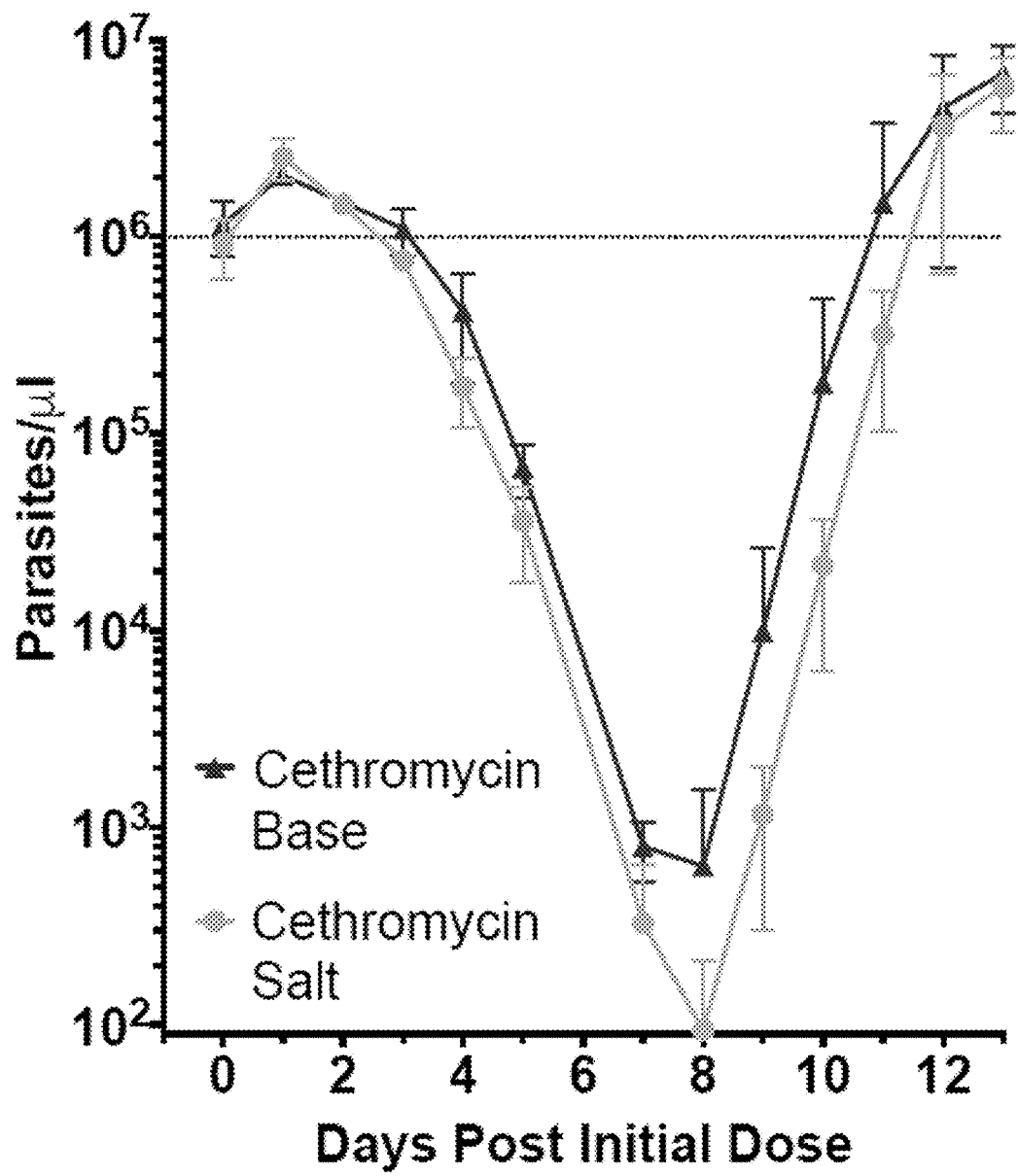
FIG. 27 shows the results of testing of cethromycin chloride against the cethromycin free base against *P. berghei*; cethromycin salt (4 days oral) kills twice as fast as the free base with a day delay in return to initial parasitemia.

An assay comparing cethromycin chloride to cethromycin free base blood stage anti-malarial activity was performed. Balbc mice (n=3/dose) were given 500,000 infected *P. berghei* (a *Plasmodium* species that infects rodents) erythrocytes i.p., then 60 mg/kg daily dose of cethromycin chloride or cethromycin free base was administered once daily for 4 days via oral gavage. Blood was drawn daily to follow course of infection, and quantified by luciferase assay. As shown in FIG. 27, cethromycin salt was superior to base, killing twice as fast as the free base and resulting in a one-day delay in return to initial parasitemia. Accordingly, cethromycin salt is expected to be superior to free base in the treatment of malaria in humans (which are infected by other *Plasmodium* species) and other mammals as well.

Example 21. In Vitro Human Hepatocyte Toxicity Studies

Anti-malarial activity and hepatocyte toxicity may be evaluated for comparing cethromycin chloride, its M1 metabolite N-desmethyl cethromycin, and/or cethromycin free base against *P. falciparum* (or other *Plasmodium* species) in vitro using chloroquine sensitive and resistant isolates, according to methods known in the art.

In one embodiment, a HIAT Assay with an additional 48-hr cytotoxicity plate, cryopreserved human hepatocytes are plated on 384-well collagen coated tissue culture plates (black-walled, clear bottom) and treated with test compound or control using a 10-point dose response range of concentrations and then incubated for two time points: 24 and 48 hours. At the end of the incubation period, the cells are loaded with relevant dye/antibody for each cell health marker. The plates are then scanned using an automated, high content imager (ArrayScan™ VTI HCS Reader). Nuclear intensity, GSH depletion, mitochondrial potential (TMRE), and ROS (reactive oxygen species) may be assessed at, e.g., 24 hours and $AC_{50}$ values reported; cell loss and nuclear size may be assessed at, e.g., 48 hours. Positive control for each of these readouts may also be included. For readouts other than cell viability, a statistical approach to data analysis is used. The vehicle controls are used to determine the definitions of "normal" for each parameter. The vehicle control wells are then used to determine significance limits for wells that have a greater than expected fraction of low or high responders.

In certain embodiments, cethromycin chloride is expected to be superior to the free base and to the M1 metabolite in avoidance of liver toxicity.

Example 22. Comparison of In Vivo Activity of Cethromycin Chloride and Base

An assay comparing cethromycin chloride, its M1 metabolite N-desmethyl cethromycin, and/or cethromycin free base in killing *P. falciparum* or other malaria-causing *Plasmodium* species in vivo may be performed according to methods disclosed herein and known in the art. Each compound may be dosed at one or more dose levels over a period of time; parasite levels, malarial illness, shortening of time to cure, prolonging survival, toxicity (in particular, liver toxicity) and other measures may be assessed during the study and after it, using both in-life and postmortem methods. In certain embodiments, cethromycin chloride is expected to be superior to the free base in reducing parasite levels, treating malarial illness, shortening the time to cure, prolonging survival, and avoiding toxicity (in particular, liver toxicity).

Example 23. Additional In Vivo Murine Activity Assays

Liver stage activity of cethromycin chloride and/or its M1 metabolite, N-desmethyl cethromycin, may be tested in a murine malaria model (n=5 mice/dose) following mosquito bite or the injection of infective sporozoites, according to methods known in the art. Quantifiable endpoints may include measured activity against malaria. The activity of the cethromycin chloride salt is expected to be superior to that of the M1 metabolite and the free base. In certain embodiments, the activity of the M1 metabolite is expected to be less than 30% of the activity of cethromycin chloride.

Additionally or alternatively, mouse malaria blood stage activity may be tested in a high parasitemia parasite killing model (n=5 mice/dose) to assess rate of killing and minimal dose and duration for cure as disclosed above and/or according to methods known in the art. Quantifiable endpoints may include measured activity against malaria. The activity of the cethromycin chloride salt is expected to be superior to that of the M1 metabolite and the free base, e.g., in increasing the rate of killing and decreasing the minimal dose and duration for cure. In certain embodiments, the activity of the M1 metabolite is expected to be less than 30% of the activity of cethromycin chloride.

Example 24. In Vitro Human Hepatocyte Toxicity Studies

Human 3 dimensional primary hepatocyte toxicity studies comparing cethromycin chloride, cethromycin free base, and the cethromycin M1 metabolite N-desmethyl cethromycin to other macrolides, such as clarithromycin, azithromycin and/or telithromycin may be performed according to methods known in the art. In vitro assays may be performed to assess drug-induced liver injury may be determined by measuring the cell health markers glutathione, ROS formation, mitochondrial dysfunction and cellular ATP in human liver cells following, e.g., 14 day repeat dose compound exposure. Quantifiable endpoints may include measured toxicity compared to other macrolides as determined by methods known in the art. It is expected that the cethromycin chloride will have acceptably low levels of liver toxicity, and in certain embodiments, no greater liver toxicity effects than other macrolides generall or cethromycin free base.

SUMMARY

Cethromycin Phosphate Pattern 1 displayed reduced crystallinity on scale up and deliquesced under accelerated storage at 25° C./97% RH. Acetate pattern 1 exhibited complex thermal behaviour and loses acetic acid at 150° C. and at high humidity. Based on its solid-state characteristics, Cethromycin Chloride Pattern 1 was chosen from among the salts examined in this study to be carried forward to polymorphism studies.

Competitive slurry experiments between Cethromycin Chloride Pattern 1 and Cethromycin Chloride Pattern 2 (1:1 physical mixture) were performed in THF, $H_2O$ and EtOAc at three different temperatures (5° C., RT and 40° C.). In all experiments conversion to Chloride Pattern 1 was observed within three days in suspension. Chloride Pattern 1 was determined to be the most stable chloride salt under the conditions investigated. Chloride Pattern 2 only shows slight increase in solubility compared to Chloride Pattern 1. The ability of a compound to form a workable solid form, provide adequate solubility in physiologically relevant conditions, and display sufficient stability, are each important considerations for development of the compound as a drug product. Often, the selection of a preferred compound form represents a balance between these factors. Thus, in certain embodiments, Cethromycin Chloride Pattern 1 is an appropriate candidate for development as a drug.

Cethromycin chloride also appeared to be superior to the free base in the treatment of malaria, as demonstrated by a murine model of the disease. It is further expected that the superiority of cethromycin chloride to the free base and the M1 metabolite in treatment of malaria and avoidance of toxicity will be demonstrated by assays disclosed herein and known in the art.

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this disclosure, and without departing from the spirit and scope thereof, can make various changes and modifications of the disclosure to adapt it to various usages and conditions.

What is claimed is:

1. A compound of structural Formula I

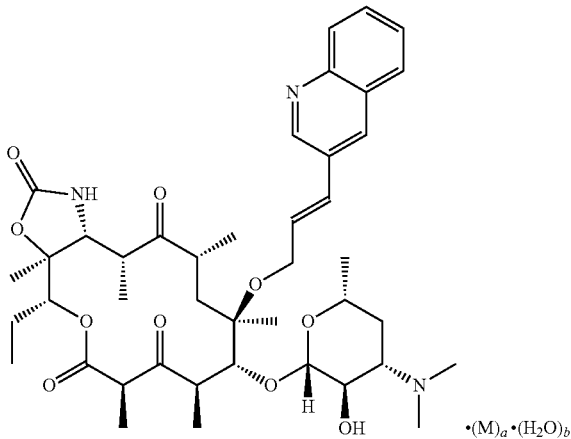

(I)

•(M)$_a$•(H$_2$O)$_b$ wherein:
a is a fractional or whole number between about 0.5 and 3.5, inclusive;
b is a fractional or whole number between about 0 and 10, inclusive; and
M is hydrochloric acid,
wherein the compound is characterized by the presence of four or more XRPD peaks with d-spacings chosen from about 14.1, about 12.9, about 10.1, about 8.8, about 8.5, about 6.5, about 5.5, about 5.1, about 4.8, and about 4.4 Å.

2. The compound as recited in claim 1, wherein a is about 1.0.

3. The compound of claim 1, characterized by the presence of six or more XRPD peaks with d-spacings chosen from about 14.1, about 12.9, about 10.1, about 8.8, about 8.5, about 6.5, about 5.5, about 5.1, about 4.8, and about 4.4 Å.

4. The compound of claim 3, characterized by the presence of eight or more XRPD peaks with d-spacings chosen from about about 14.1, about 12.9, about 10.1, about 8.8, about 8.5, about 6.5, about 5.5, about 5.1, about 4.8, and about 4.4 Å.

5. The compound of claim 1, characterized by the presence of four or more XRPD peaks with d-spacings chosen from about 16.5, about 14.5, about about 10.5, about 9.1, about 8.3, about 7.8, about 7.6, about 5.2, about 4.7, and about 4.1 Å.

6. The compound of claim 5, characterized by the presence of six or more XRPD peaks with d-spacings chosen from about 16.5, about 14.5, about 10.5, about 9.1, about 8.3, about 7.8, about 7.6, about 5.2, about 4.7, and about 4.1 Å.

7. The compound of claim 6, characterized by the presence of eight or more XRPD peaks with d-spacings chosen from about 16.5, about 14.5, about 10.5, about 9.1, about 8.3, about 7.8, about 7.6, about 5.2, about 4.7, and about 4.1 Å.

8. A pharmaceutical composition comprising a compound as recited in claim 1 together with a pharmaceutically acceptable carrier.

9. A method of inhibition of microbial protein synthesis comprising contacting a microbe with a compound as recited in claim 1.

10. The method as recited in claim 9, wherein the microbe is a bacterium.

11. The method as recited in claim 9, wherein the microbe is a protozoan.

12. A method of treatment of an infectious disease comprising the administration of a therapeutically effective amount of a compound as recited in claim 1 to a patient in need thereof.

13. A method of treatment of an infectious disease comprising the administration of:
a. a therapeutically effective amount of a compound as recited in claim 1; and
b. another therapeutic agent.

14. The method as recited in claim 12 wherein said infectious disease is malaria.

15. The method as recited in claim 12 wherein said infectious disease is caused by a protozoan.

16. A method for achieving an effect in a patient comprising the administration of a therapeutically effective amount of the compound as recited in claim 1 to a patient, wherein the effect is chosen from:
reducing microbial level(s);
increasing the rate of microbial killing;
decreasing the minimal dose of the compound as recited in claim 1 for reduction of the level of microbia to an undetectable level; and
decreasing the duration of time required for reduction of the level of microbia to an undetectable level.

17. The method as recited in claim 16, wherein the microbe is a protozoan.

18. The method as recited in claim 15, wherein the protozoan is chosen from *Cryptosporidium; Coccidia; Plasmodium; Toxoplasma; Babesia*; and *Neospora*.

19. The method as recited in claim 18, wherein the protozoan is a *Plasmodium* species.

20. The method as recited in claim 19, wherein the *Plasmodium* is chosen from *P. falciparum, P. vivax, P. ovale, P. malariae*, and *P. knowlesi*.

21. The method as recited in claim 20, wherein the *Plasmodium* is *P. falciparum*.

* * * * *